(12) United States Patent
Frysz et al.

(10) Patent No.: US 9,463,329 B2
(45) Date of Patent: Oct. 11, 2016

(54) SHIELDED THREE-TERMINAL FLAT-THROUGH EMI/ENERGY DISSIPATING FILTER WITH CO-FIRED HERMETICALLY SEALED FEEDTHROUGH

(71) Applicant: Greatbatch Ltd., Clarence, NY (US)

(72) Inventors: Christine A. Frysz, Orchard Park, NY (US); Robert A. Stevenson, Canyon Country, CA (US); Thomas Marzano, Eash Amherst, NY (US); Xiaohong Tang, Williamsville, NY (US); William C. Thiebolt, Tonawanda, NY (US); Keith W. Seitz, Clarence Center, NY (US)

(73) Assignee: Greatbatch Ltd., Clarence, NY (US)

( * ) Notice: Subject to any disclaimer, the term of this patent is extended or adjusted under 35 U.S.C. 154(b) by 129 days.

(21) Appl. No.: 14/556,239

(22) Filed: Dec. 1, 2014

(65) Prior Publication Data

US 2016/0151635 A1    Jun. 2, 2016

Related U.S. Application Data

(63) Continuation-in-part of application No. 14/187,295, filed on Feb. 23, 2014, which is a continuation-in-part of application No. 13/873,832, filed on Apr. 30, 2013, now Pat. No. 8,868,189, which is a continuation of (Continued)

(51) Int. Cl.
*A61N 1/00* (2006.01)
*A61N 1/39* (2006.01)
(Continued)

(52) U.S. Cl.
CPC .............. *A61N 1/3968* (2013.01); *A61N 1/08* (2013.01); *A61N 1/362* (2013.01)

(58) Field of Classification Search
CPC ... A61N 1/08; A61N 1/362; A61N 2001/086
USPC ........................................................ 607/119
See application file for complete search history.

(56) References Cited

U.S. PATENT DOCUMENTS

| | | | |
|---|---|---|---|
| 3,681,612 A | 8/1972 | Volg et al. | |
| 3,745,430 A | 7/1973 | Lunquist et al. | |

(Continued)

FOREIGN PATENT DOCUMENTS

| | | |
|---|---|---|
| JP | 6176962 | 6/1994 |
| JP | 7272975 | 10/1995 |

(Continued)

*Primary Examiner* — Amanda Patton
*Assistant Examiner* — Philip C Edwards
(74) *Attorney, Agent, or Firm* — Marc G. Martino; Michael F. Scalise

(57) ABSTRACT

A hermetic terminal assembly for an AIMD includes a shielded three-terminal flat-through EMI energy dissipating filter and a hermetically sealed feedthrough configured to be attachable to the ferrule or AIMD housing. The flat-through filter includes a first shield plate, an active electrode plate, and a second shield plate where the shield plates are electrically coupled to a metallization which in turn is coupled either to the ferrule or AIMD housing. The feedthrough includes an alumina substrate comprised of at least 96% alumina and a via hole with a substantially closed pore and substantially pure platinum fill. The platinum fill forms a tortuous and mutually conformal knitline or interface between the alumina substrate and the platinum fill, wherein the platinum fill is electrically coupled to at least one active electrode plate in non-conductive relationship to the at least one first and second shield plates.

32 Claims, 60 Drawing Sheets

Related U.S. Application Data application No. 13/528,052, filed on Jun. 20, 2012, now Pat. No. 8,433,410, which is a continuation of application No. 12/407,402, filed on Mar. 19, 2009, now Pat. No. 8,195,295, application No. 14/556,239, which is a continuation-in-part of application No. 13/743,276, filed on Jan. 16, 2013, now Pat. No. 9,233,253.

(60) Provisional application No. 61/150,061, filed on Feb. 5, 2009, provisional application No. 61/144,102, filed on Jan. 12, 2009, provisional application No. 61/116,094, filed on Nov. 19, 2008, provisional application No. 61/038,382, filed on Mar. 20, 2008, provisional application No. 61/587,029, filed on Jan. 16, 2012, provisional application No. 61/587,287, filed on Jan. 17, 2012, provisional application No. 61/587,373, filed on Jan. 17, 2012.

(51) Int. Cl.
  *A61N 1/362* (2006.01)
  *A61N 1/08* (2006.01)

(56) References Cited

U.S. PATENT DOCUMENTS

| | | |
|---|---|---|
| 3,961,294 A | 6/1976 | Hollyday |
| 4,424,551 A | 1/1984 | Stevenson |
| 4,858,064 A | 8/1989 | Segawa et al. |
| 5,039,965 A | 8/1991 | Higgins, Jr. |
| 5,268,810 A | 12/1993 | DiMarco et al. |
| 5,331,505 A | 7/1994 | Wilheim |
| 5,333,095 A | 7/1994 | Stevenson |
| 5,450,090 A | 9/1995 | Gels et al. |
| 5,491,300 A | 2/1996 | Huppenthal et al. |
| 5,493,259 A | 2/1996 | Blalock et al. |
| 5,620,476 A | 4/1997 | Truex et al. |
| 5,650,759 A | 7/1997 | Hittman et al. |
| 5,683,435 A | 11/1997 | Truex |
| 5,757,252 A | 5/1998 | Cho et al. |
| 5,765,779 A | 6/1998 | Hancock et al. |
| 5,782,891 A | 7/1998 | Hassler et al. |
| 5,822,174 A | 10/1998 | Yamate et al. |
| 5,905,627 A | 5/1999 | Brendel |
| 5,929,729 A | 7/1999 | Swarup |
| 5,959,336 A | 9/1999 | Barsan |
| 5,973,906 A | 10/1999 | Stevenson et al. |
| 5,973,907 A | 10/1999 | Reed |
| 5,978,204 A | 11/1999 | Stevenson |
| 6,137,161 A | 10/2000 | Gilliland et al. |
| 6,146,743 A | 11/2000 | Haq et al. |
| 6,373,673 B1 | 4/2002 | Anthony |
| 6,424,234 B1 | 7/2002 | Stevenson |
| 6,456,481 B1 | 9/2002 | Stevenson |
| 6,459,935 B1 | 10/2002 | Piersma |
| 6,473,314 B1 | 10/2002 | Custer |
| 6,512,666 B1 | 1/2003 | Duva |
| 6,529,103 B1 | 3/2003 | Brendel |
| 6,566,978 B2 | 5/2003 | Stevenson |
| 6,660,116 B2 | 12/2003 | Wolf et al. |
| 6,765,680 B2 | 7/2004 | Carr et al. |
| 6,765,779 B2 | 7/2004 | Stevenson |
| 6,765,780 B2 | 7/2004 | Brendel |
| 6,768,630 B2 | 7/2004 | Togashi |
| 6,806,806 B2 | 10/2004 | Anthony |
| 6,888,715 B2 | 5/2005 | Stevenson et al. |
| 7,038,900 B2 | 5/2006 | Stevenson |
| 7,046,499 B1 | 5/2006 | Imani et al. |
| 7,110,227 B2 | 9/2006 | Anthony et al. |
| 7,113,387 B2 | 9/2006 | Stevenson et al. |
| 7,199,995 B2 | 4/2007 | Stevenson |
| 7,236,834 B2 | 6/2007 | Christopherson et al. |
| 7,301,748 B2 | 11/2007 | Anthony et al. |
| 7,310,216 B2 | 12/2007 | Stevenson |
| 7,322,832 B2 | 1/2008 | Kronich et al. |
| 7,327,553 B2 | 2/2008 | Brendel |
| 7,363,090 B2 | 4/2008 | Halperin |
| 7,423,860 B2 | 9/2008 | Anthony et al. |
| 7,428,136 B2 | 9/2008 | Barnett |
| 7,433,168 B2 | 10/2008 | Anthony |
| 7,436,672 B2 | 10/2008 | Ushijima et al. |
| 7,439,449 B1 | 10/2008 | Kumar et al. |
| 7,446,996 B2 | 11/2008 | Togashi |
| 7,450,396 B2 | 11/2008 | Ye et al. |
| 7,495,884 B2 | 2/2009 | Togashi |
| 7,586,728 B2 | 9/2009 | Anthony |
| 7,593,208 B2 | 9/2009 | Anthony et al. |
| 7,675,729 B2 | 3/2010 | Anthony et al. |
| 7,679,926 B2 | 3/2010 | Hsu et al. |
| 7,702,387 B2 | 4/2010 | Stevenson |
| 7,719,854 B2 | 5/2010 | Youker et al. |
| 7,733,621 B2 | 6/2010 | Anthony et al. |
| 7,853,324 B2 | 12/2010 | Stevenson |
| 7,853,325 B2 | 12/2010 | Dabney |
| 7,899,551 B2 | 3/2011 | Westlund |
| 7,916,013 B2 | 3/2011 | Stevenson |
| 7,945,322 B2 | 5/2011 | Stevenson |
| 7,957,806 B2 | 6/2011 | Stevenson et al. |
| 8,219,208 B2 | 7/2012 | Stevenson et al. |
| 2005/0201039 A1 | 9/2005 | Stevenson et al. |
| 2006/0032665 A1 | 2/2006 | Ice |
| 2006/0085043 A1 | 4/2006 | Stevenson |
| 2006/0212096 A1 | 9/2006 | Stevenson |
| 2007/0123949 A1 | 5/2007 | Dabney et al. |
| 2007/0179554 A1 | 8/2007 | Iyer et al. |
| 2007/0203529 A1 | 8/2007 | Iyer et al. |
| 2007/0288058 A1 | 12/2007 | Halperin et al. |
| 2008/0049376 A1 | 2/2008 | Stevenson |
| 2008/0049410 A1 | 2/2008 | Kawaguchi et al. |
| 2008/0158746 A1 | 7/2008 | Anthony et al. |
| 2008/0195180 A1 | 8/2008 | Stevenson et al. |
| 2008/0239622 A1 | 10/2008 | Hsu et al. |
| 2008/0247111 A1 | 10/2008 | Anthony et al. |
| 2008/0247116 A1 | 10/2008 | Kawano et al. |
| 2008/0247117 A1 | 10/2008 | Elam et al. |
| 2008/0264685 A1 | 10/2008 | Park et al. |
| 2008/0277153 A1 | 11/2008 | Teshome et al. |
| 2009/0097219 A1 | 4/2009 | Cho et al. |
| 2009/0107717 A1 | 4/2009 | Hsu et al. |
| 2009/0116167 A1 | 5/2009 | Stevenson et al. |
| 2009/0128976 A1 | 5/2009 | Anthony |
| 2009/0139760 A1 | 6/2009 | Tanaka |
| 2009/0180237 A1 | 7/2009 | Hou et al. |
| 2009/0187229 A1 | 7/2009 | Lavie |
| 2009/0236141 A1 | 9/2009 | Kim et al. |
| 2009/0243756 A1 | 10/2009 | Stevenson et al. |
| 2010/0046135 A1 | 2/2010 | Niki et al. |
| 2010/0046137 A1 | 2/2010 | Adachi |
| 2010/0109958 A1 | 5/2010 | Haubrich et al. |
| 2010/0109966 A1 | 5/2010 | Mateychuk et al. |
| 2010/0149042 A1 | 6/2010 | Utsi et al. |
| 2010/0151113 A1 | 6/2010 | Shelton |

FOREIGN PATENT DOCUMENTS

| | | |
|---|---|---|
| JP | 2001068958 | 3/2001 |
| JP | 2004254257 | 9/2004 |
| JP | 2004289760 | 10/2004 |
| JP | 2005117606 | 4/2005 |
| JP | 2007129565 | 11/2005 |

BODY FLUID SIDE

FILTER PERFORMANCE

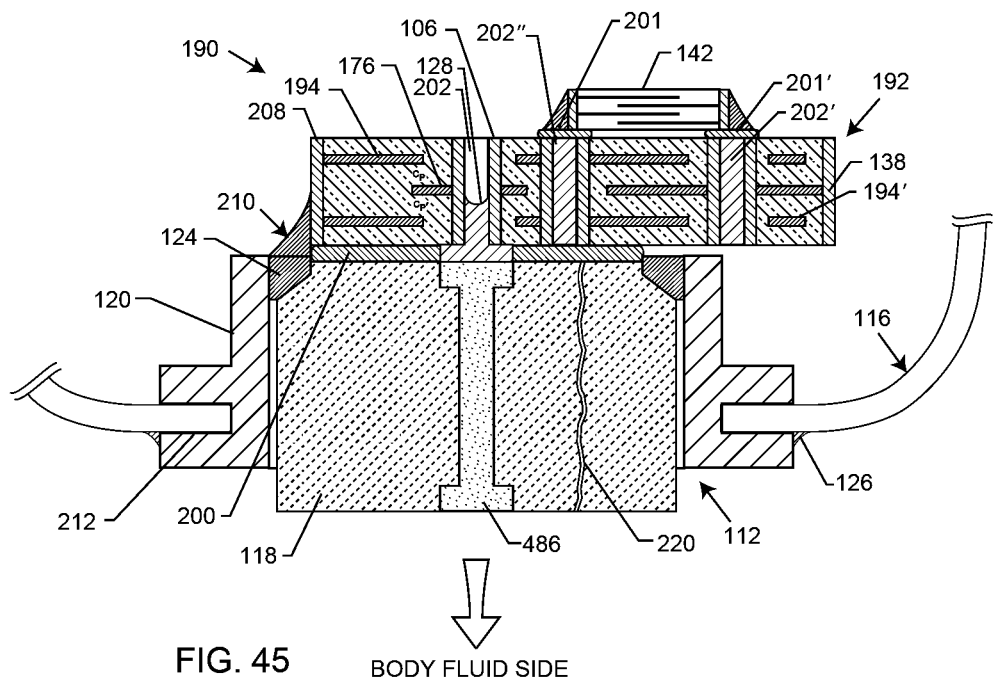
FIG. 45   BODY FLUID SIDE
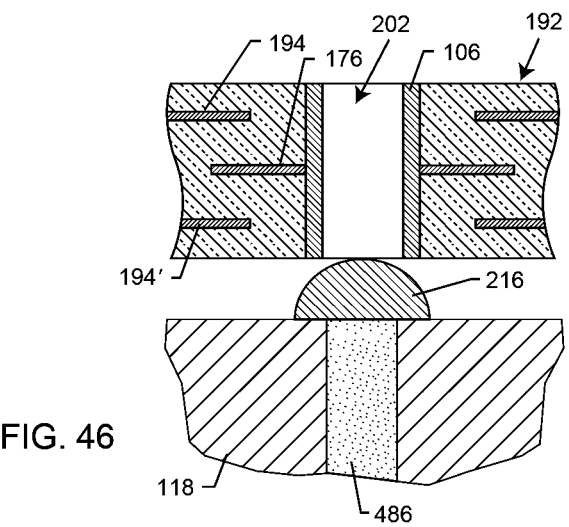
FIG. 46

SHIELDED THREE-TERMINAL FLAT-THROUGH EMI/ENERGY DISSIPATING FILTER WITH CO-FIRED HERMETICALLY SEALED FEEDTHROUGH

CROSS REFERENCE TO RELATED APPLICATIONS

This application is a continuation-in-part to application Ser. No. 14/187,295 filed on Feb. 23, 2014, which was a continuation-in-part application to application Ser. No. 13/873,832 filed on Apr. 30, 2013, now U.S. Pat. No. 8,868,189 issued on Oct. 21, 2014, which was a continuation to application Ser. No. 13/528,052 filed on Jun. 20, 2012, now U.S. Pat. No. 8,433,410 issued on Apr. 30, 2013, which was a continuation application of application Ser. No. 12/407,402 filed on Mar. 19, 2009, now U.S. Pat. No. 8,195,295 issued on Oct. 1, 2009, which itself claimed priority to provisional applications 61/150,061 filed on Feb. 5, 2009, 61/144,102 filed on Jan. 12, 2009, 61/116,094 filed on Nov. 19, 2008 and 61/038,382 filed on Mar. 20, 2008. This application is also a continuation-in-part to application Ser. No. 13/743,276 filed Jan. 16, 2013, which claimed priority to provisional application 61/587,287 filed Jan. 17, 2012 and provisional application 61/587,373 filed Jan. 17, 2012 and provisional application 61/587,029 filed Jan. 16, 2012. The contents of all of the above referenced applications are fully incorporated herein with these references.

DESCRIPTION

1. Field of the Invention

The present invention relates generally to implantable medical devices, hermetic terminals, and feedthrough filter capacitor EMI filters. More particularly, the present invention relates to a hybrid EMI filter substrate and/or flex cable assembly which embodies embedded shielded flat-through feedthrough filters and/or energy dissipating circuit elements, and wherein a hermetic terminal subassembly utilizing a co-fired essentially pure platinum filled via along with novel ways of making electrical connections on the body fluid side and on the device side of the active implantable medical device (AIMD) housing may be utilized. This invention is applicable to a wide range of circuits, connectors, terminals and/or hermetic seals that support lead wires as they ingress/egress into electronic modules or shielded housings, that support componentry to protect sensitive electronics in a device, and that improves patient safety. In particular, the present invention applies to a wide variety of active implantable medical devices (AIMDs).

2. Background of the Invention

The figures and disclosure within U.S. patent application Ser. Nos. 13/873,832 and 13/743,254 with certain select prior art figures provide background for better understanding the significance and novelty of the present invention and are incorporated in full with these references. In general, U.S. patent application Ser. Nos. 13/873,832 and 13/743,254 provide broad explanation of technologies relevant to the present invention including general description of medical devices, filtering technology regarding the attenuation of undesirable electromagnetic interference (EMI) as it relates to medical devices, sealing technology for sustainable hermeticity and long term performance, suitable subassembly joining, significance of materials selection, and appropriate processing and manufacturing methods to name a few. In depth discussion of prior art concepts are also provided, including how issues that are still present with current state technology remain unsolved or can be improved upon by the novel inventions within. Select prior art concepts are included here to provide further clarity to the novelty and benefits of the present invention. Throughout this description, functionally equivalent elements will be given the same reference number, irrespective of the embodiment being shown.

FIG. 1 illustrates various types of active implantable and external medical devices 100 (100A through 100M) that are currently in use. FIG. 1 is a wire formed diagram of a generic human body showing a number of implanted medical devices. A more detailed description of these devices and the issues upon which improvements can be made are given in U.S. patent application Ser. Nos. 13/873,832 and 13/743,254.

FIG. 2 is an exemplary prior art cardiac pacemaker 100C taken from FIG. 1. Like most of the AIMDs in FIG. 1, it has an electromagnetic shield housing 116 which is typically stainless steel, titanium, an electromagnetic shield ceramic housing and the like. It has a hermetic seal 112 which can be a gold braze hermetic seal between pure alumina ceramic and metal ferrules and conductors, or it may even be a glass or glass ceramic seal type structure. Cardiac pacemakers tend to have a header block 101 made from a polymer, such as Tecothane. In this case, a dual chamber bipolar pacemaker is shown meaning that the header block has two ports 103 and 103'. The two ports are configured to be contactable to lead connectors 105 and 105'. When implanted, the bipolar leads are routed into the right ventricle 109 and the right atrium 109' of the heart 314. Referring once again to FIG. 2, a prior art feedthrough capacitor 132 that is bonded directly to the prior art hermetic seal assembly 112 is shown. There is also an optional wire bond substrate 136 which has wire bond pads 138 for convenient connection of circuit board wires 111. These wires 111 may be either thermosonically, ultrasonically, soldered or otherwise joined to each one of the respective terminal pads 138, 138', 138", 138''' and the circuit ground pad 140. Wires 111 are routed between these bond pads and similar lands or bond pads on the cardiac pacemaker main circuit board 250 as shown.

FIG. 3 is a prior art quadpolar feedthrough capacitor 132 having four through holes.

FIG. 4 is a cross-section showing the internal electrodes 102, 104 of the capacitor 132 of FIG. 3.

FIG. 5 is a schematic diagram showing the four discrete feedthrough capacitors comprising the quadpolar feedthrough capacitor 132 of FIGS. 3 and 4.

FIG. 6 illustrates a prior art quadpolar feedthrough capacitor 132 mounted on top of a hermetic insulator 118 wherein a wire bond substrate 136 is attached to the top as shown. Wire bond pads 138, 138', 138", 138''' and 140 are shown for convenient connection to the internal circuitry of the AIMD. This is more thoroughly described in FIGS. 75 and 76 of U.S. Pat. Nos. 7,038,900 and 7,310,216, the contents of which are incorporated herein by reference.

FIG. 7 is a cross-section taken generally from section 11-11 from FIG. 6. In FIG. 7, the internal circuit traces $T_1$ through $T_4$ to the wire bond pads 138-138''' are shown. Note that there is an additional wire bond pad 140 shown on the left side of the wire bond substrate 136 of FIG. 6 that is also shown in FIG. 7. This is a ground connection to the outside diameter of the hermetic seal ferrule 120 and provides a convenient connection point for electronic circuits and the like that need a ground attachment point on the inside of the AIMD.

FIG. 8 is a schematic diagram of the prior art quadpolar hermetic feedthrough 132 wire bond pad 136 assembly of FIG. 6

FIG. 9 is a different type of prior art MLCC feedthrough capacitor that is built into a special configuration. It is known in the art by several trade names including some as a flat-through capacitor. It will be referred to herein as a flat-through capacitor 174. At low frequencies, the flat-through capacitor 174 exhibits ideal capacitance behavior versus frequency. That is, its attenuation curve versus frequency is nearly ideal. This is because it is truly a three-terminal device which acts as a transmission line in a manner similar to those of prior art discoidal feedthrough capacitors 132. This is better understood by referring to its internal electrode plate geometry as shown in FIG. 10. Shown is a through or active electrode plate 175 that is sandwiched between two ground electrode plates 178 and 178'. The through or active electrode plate 175 is connected at both ends by termination surfaces 180 and 182. When the capacitor is mounted between circuit trace lands 184 and 186 as shown in FIG. 9, the circuit trace is connected together between points 184 and 186. Referring to the active circuit trace 175 in FIG. 10, one can see that there is a current $i_1$ that enters. If this is a high frequency EMI current, it will be attenuated along its length by the capacitance of the flat-through capacitor and emerge as a much smaller in amplitude EMI signal at terminal 2 as $i_1'$. Similar to discoidal feedthrough capacitors, the flat-through capacitor 174 as illustrated in FIG. 9 is also a three-terminal capacitor. The point of current input $i_1$ is known as terminal 1, the point of circuit current egress $i_1'$ is known as terminal 2 and ground is known as terminal 3. In other words, any RF currents that are flowing through the circuit trace must pass through the electrodes 175 of the capacitor 174. This means that any RF signals are exposed for the full length of the electrode plate 175 between the ground electrodes 178 and the capacitance that is formed between them. This is an alternative shape (versus a discoidal shape) for a three-terminal feedthrough capacitor. This alternative shape for a feedthrough capacitor 174, however, is not conveniently mountable in such a way that it becomes an integral part of an overall EMI shield. There will be a frequency at which undesirable RF coupling 188 across the device can occur. This is particularly observable at 100 MHz or above. At very high frequencies, such as above 1 GHz, undesirable RF coupling can become quite serious. Furthermore, flat-through capacitor design dictates that circuit currents must flow through the electrodes of the flat-through capacitor itself. As a point of reference, for prior art discoidal feedthrough capacitors 132, the circuit current passes through a robust lead in a feedthrough hole. The only current that flows in the electrodes of prior art feedthrough capacitors is high frequency EMI current. Further complicating prior art flat-through capacitor capability for handling high currents is its electrode thickness manufacturing limitations. Prior art MLCC and flat-through electrodes must be kept relatively thin to promote ceramic grain growth through the electrodes in order to keep the capacitor layers from delaminating during manufacturing or worse yet, during subsequent mechanical or thermal shocks which can cause latent failures. These monolithic ceramic electrode thickness limitations directly impact the electrode conductivity. Since electrode thickness is limited due to manufacturing capability, the limitations to electrode thickness means that prior art flat-through capacitors 174 have relatively high series resistance and can only be rated to a few hundred milliamps or a few amps at best. Implantable defibrillators, however, therapeutically deliver a high voltage pulse of over 20 amps, and so these prior art flat-through capacitors are not capable of handling these high circuit currents.

FIG. 11 is the schematic diagram of the prior art flat-through capacitor 174 as illustrated in FIG. 9. Note that its schematic diagram is the same as that shown in FIG. 8. There are four circuit schematics shown in FIG. 8 one each representing the four terminals for the quadpolar feedthrough capacitor 132 given in FIGS. 5 and 6. The difference between the flat-through and the feedthrough capacitors is that feedthrough capacitors are inherently configured to be mounted as an integral part of an overall shield which precludes the problem of RF coupling (see FIGS. 3-5).

FIG. 12 illustrates the attenuation versus frequency response curve which is shown generically for the flat-through capacitor of FIG. 9. If it were not for cross-coupling of RF energy, it would perform as an ideal or nearly perfect capacitor would. As shown in FIG. 12, there is always a certain frequency at which the attenuation starts to parasitically drop off due to this cross-coupling. This drop off is unquestionably undesirable in active implantable medical device (AIMD) applications as there would be less protection against high frequency EMI emitters such as cellular phones and the like. Implantable medical applications, however, do not generally require filtering much above 3 GHz due to the effective reflection and absorption of human skin of RF energy at frequencies above 3 GHz. This parasitic drop off in attenuation due to cross-coupling is more particularly problematic in military and space applications where EMI filter attenuation requirements of up to 10 or even 18 GHz. Space and military circuits have to operate in the presence of extremely high frequency emitters, such as GHz radars and the like.

Accordingly, based on the collective consideration of the disclosures provided in U.S. patent application Ser. Nos. 13/873,832 and 13/743,254 and the prior art discussed above, there is further need for a flat-through type of capacitor that eliminates problems associated with parasitic attenuation degradation due to RF cross-coupling across (or outside or around) the capacitor, and that can handle much higher circuit currents through their "through" electrodes. Also, there is a need for a filtered structure like a hermetic terminal or feedthrough, any subassembly made using same and any feedthrough filter EMI capacitor assembly which minimizes intolerable stress levels, allows use of preferred materials for AIMDS and eliminates high-priced, platinum, platinum-iridium or equivalent noble metal hermetic terminal subassembly leadwires. What is additionally needed is an efficient, simple and robust subassembly comprising a flat-through type of capacitor and a filtered structure for use in medical devices. Correspondingly, it is also needed for this subassembly to make a similar efficient, simple and robust electrical connection between the electronics on the device side of the AIMD to the filter capacitor and hermetic terminal subassembly. The present invention fulfills these needs and provides other related advantages.

SUMMARY OF THE INVENTION

A primary objective of the present invention is to provide a novel shielded three-terminal flat-through EMI/energy dissipating filter to which a hermetically sealed feedthrough comprising an alumina substrate wherein a via hole is disposed. A substantially closed pore and substantially pure platinum fill is disposed within the via hole. The novel three-terminal flat-through EMI/energy dissipating filter embodies one or more flat-through capacitors whose internal electrodes are high frequency shielded, are much thicker (compared to prior art MLCC flat-through thick film electrode technology) and higher in both cross-sectional and surface area (robust and able to carry much higher through circuit currents), whose electrodes can be configured with integral co-planar inductor elements, and can be optionally configured to accept a variety of surface mounted electronic components (like additional discrete or embedded capacitors, inductors, diodes, RFID chips, and the like).

The hermetically sealed feedthrough comprising an alumina substrate is comprised of at least 96% alumina and has a thickness extending from a body fluid side (first substrate side) to a device side (second substrate side). The via hole is disposed through the alumina substrate from the body fluid side to the device side, and the substantially closed pore and substantially pure platinum fill disposed within the via hole extends between the body fluid side and the device side of the alumina substrate. A hermetic seal between the platinum fill and the alumina substrate exists, wherein the platinum fill forms a tortuous and mutually conformal knitline or interface between the alumina substrate and the platinum fill, and is configured to be attachable to the ferrule or the AIMD housing. The platinum fill may be electrically coupled to the at least one active electrode plate in non-conductive relationship to the at least one first and second shield plates.

The higher surface area of the novel shielded three-terminal flat-through EMI/energy dissipating filter of the present invention maximizes the value of the flat-through capacitance. The present invention resides in a shielded three-terminal flat-through EMI/energy dissipating filter which comprises an active electrode plate through which a circuit current passes between a first terminal and a second terminal, and a plurality of shield plates substantially enveloping the active electrode plate, wherein the shield plates are electrically coupled to a grounded third terminal. Preferably, the plurality of shield plates include a first shield plate on a first side of the active electrode plate, and a second shield plate on a second side of the active electrode plate opposite the first shield plate. The active electrode plate is insulated from the shield plates by a dielectric material such that the active electrode plate and the shield plates cooperatively form a flat-through capacitor. A conductor typically extends through at least one of the shield plates in non-conductive relation. The conductor is electrically coupled to the active electrode plate to form the first terminal. A shielded fixture may be provided through which the conductor extends in non-conductive relation. The fixture may comprise a hermetic seal for an active implantable medical device (AIMD). The surface area of the active electrode plate is maximized to increase parasitic capacitance and minimize resistance to current flow.

Various novel shielded three-terminal flat-through EMI/energy dissipating filters embodiments are disclosed in U.S. patent application Ser. No. 13/873,832. Various novel co-fired hermetically sealed feedthrough embodiments are disclosed in U.S. patent application Ser. No. 13/743,254. The novel embodiments of the present invention leverage the novel shielded three-terminal flat-through EMI/energy dissipating filters embodiments and the novel co-fired hermetically sealed feedthrough embodiments disclosed in the above U.S. patent applications creating a hermetic terminal assembly for an AIMD having a shielded three-terminal flat-through EMI energy dissipating filter and a hermetically sealed feedthrough configured to be attachable to the ferrule or AIMD housing.

BRIEF DESCRIPTION OF THE DRAWINGS

The accompanying drawings illustrate the invention. In such drawings:

FIG. 45 is a sectional view taken generally along the line 45-45 of FIG. 43;

FIG. 46 is an enlarged sectional view showing an alternative connection methodology wherein a via hole is filled and then attached to a solder bump;

DETAILED DESCRIPTION OF THE PREFERRED EMBODIMENTS

Figure 1:
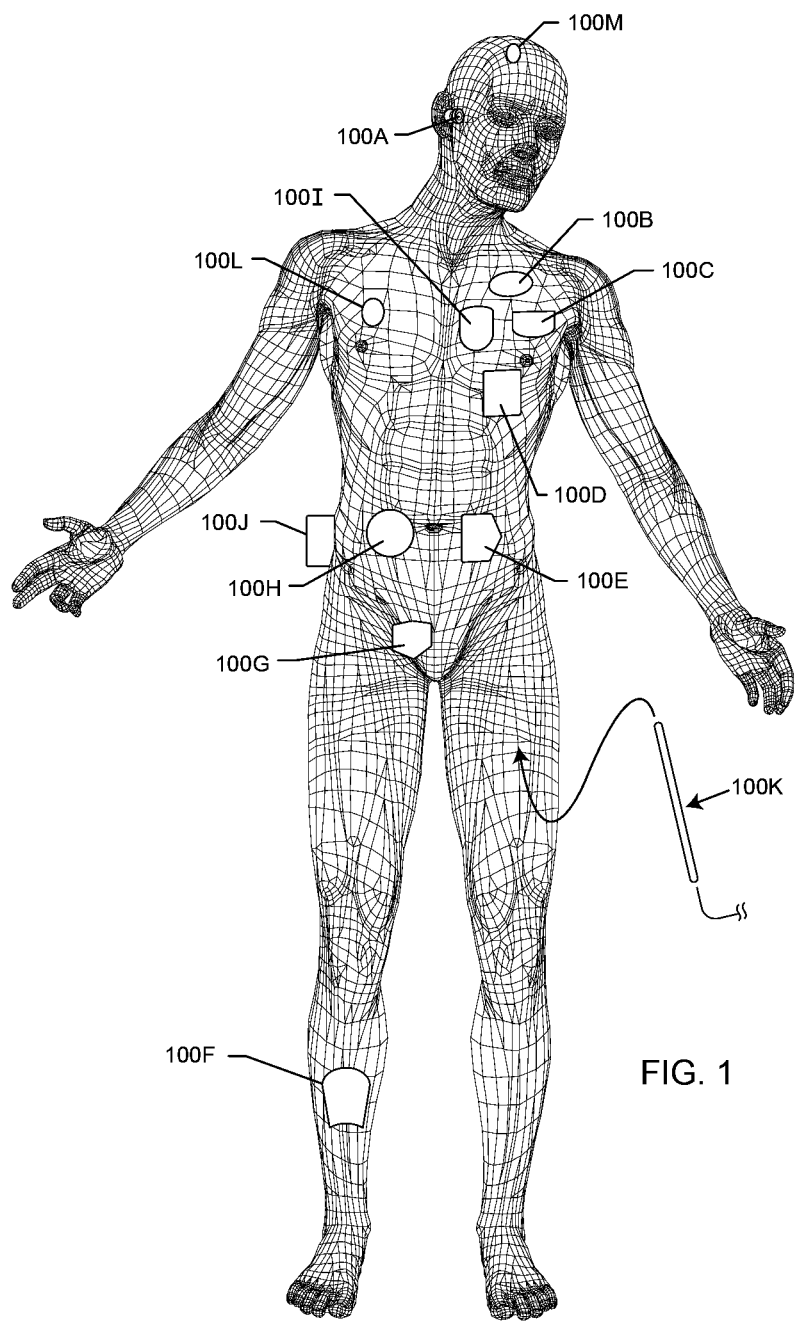
FIG. 1 is a wire formed diagram of a generic human body showing a number of implanted medical devices.
Figure 2:
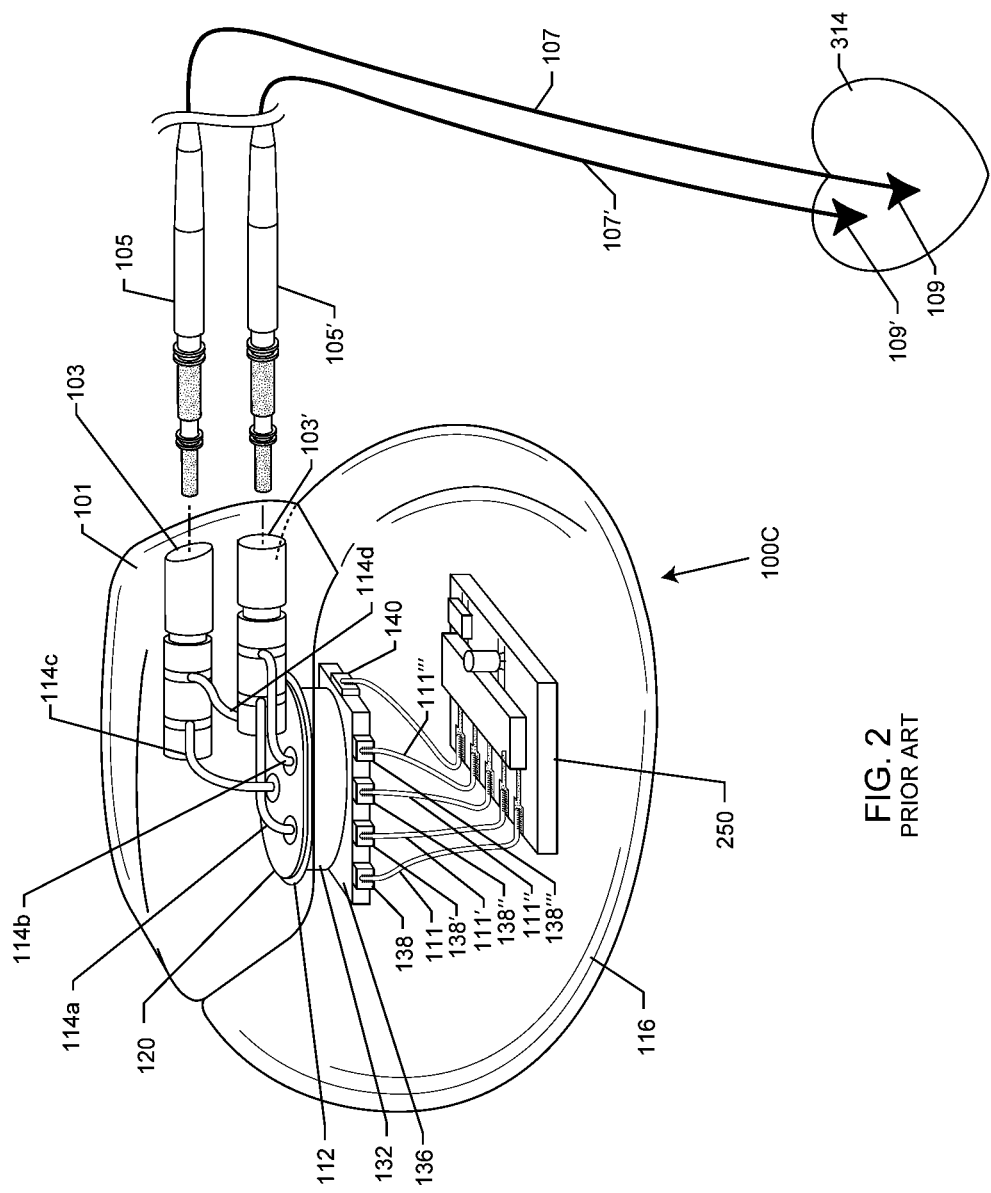
FIG. 2 is a oblique view of an active implantable medical device.
Figure 3:
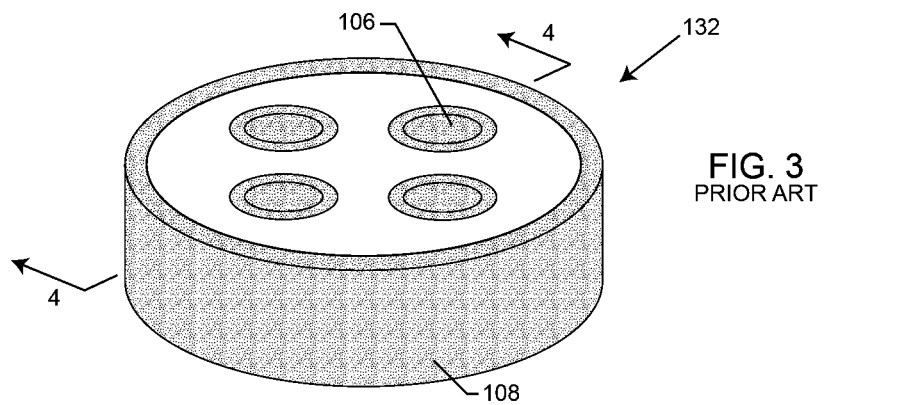
FIG. 3 is a isometric view of a quadpolar feedthrough capacitor.
Figure 4:
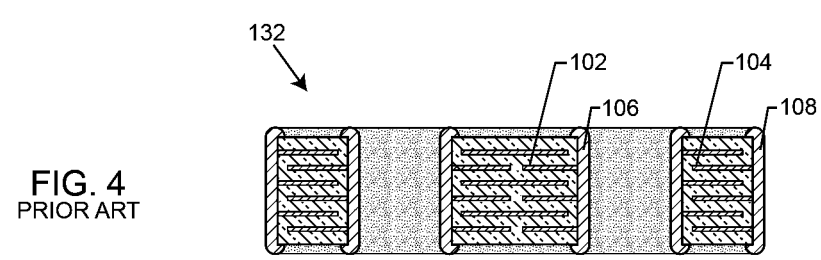
FIG. 4 is sectional view taken along the line 4-4 of FIG. 3.
Figure 5:
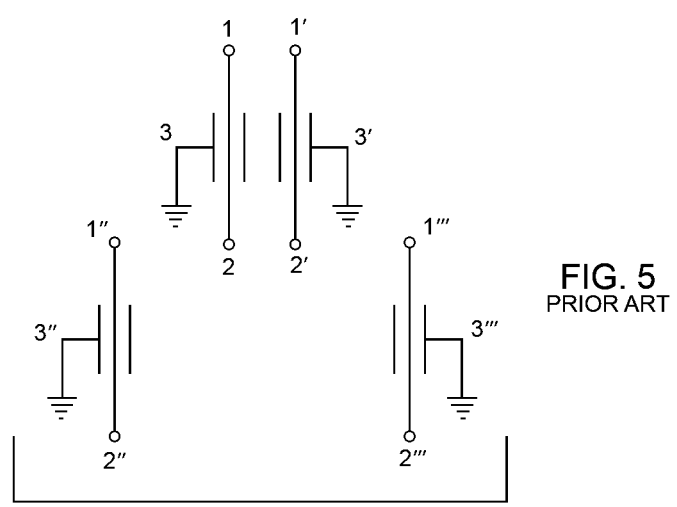
FIG. 5 is an electrical schematic diagram of the quadpolar feedthrough capacitor of FIGS. 3 and 4.
Figure 6:
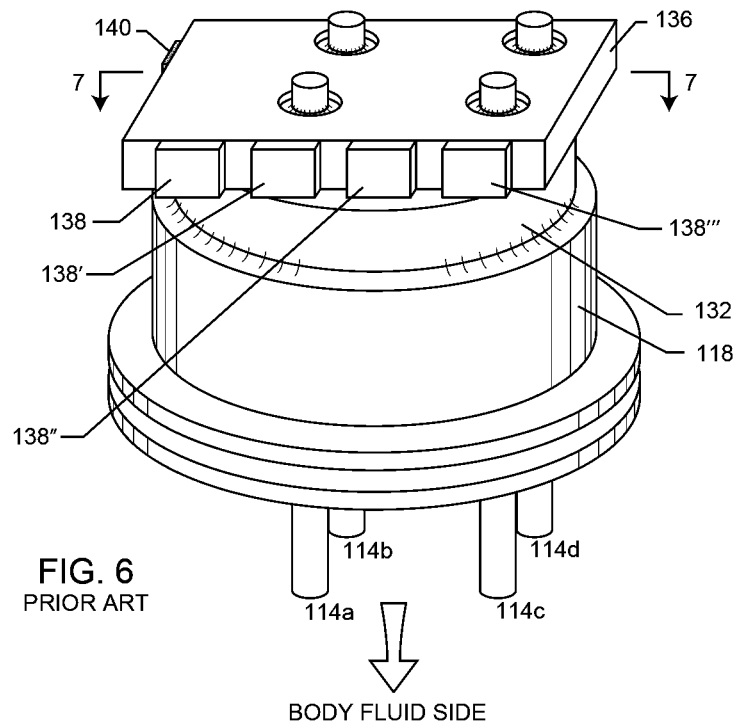
FIG. 6 is an oblique view of a quadpolar feedthrough capacitor mounted on top of a hermetic seal.
Figure 7:
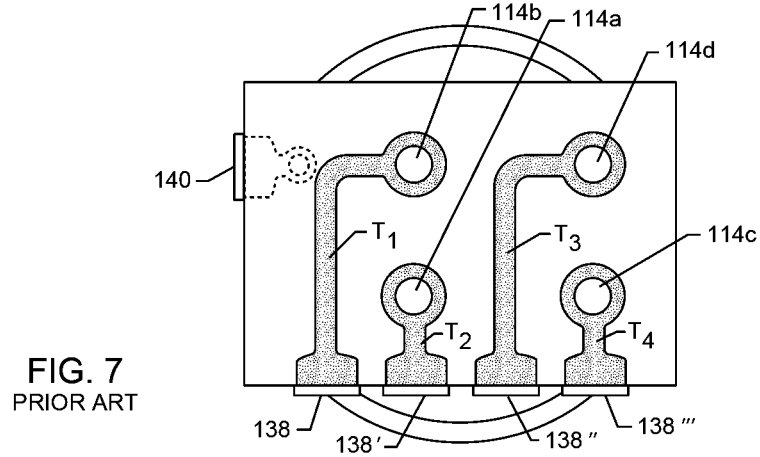
FIG. 7 is a sectional view taken generally along the line 7-7 of FIG. 6.
Figure 8:
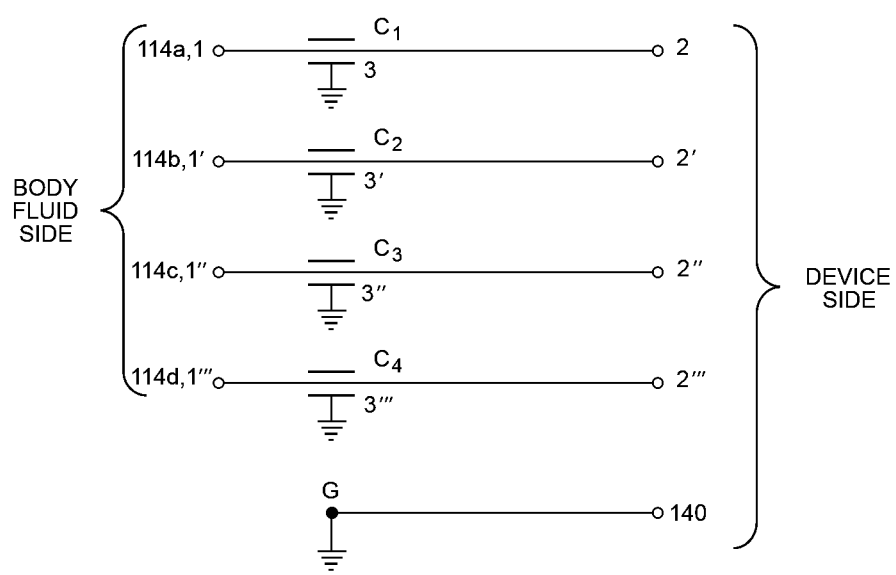
FIG. 8 is an electrical schematic diagram of the quadpolar hermetic feedthrough terminal shown in FIG. 6.
Figure 9:
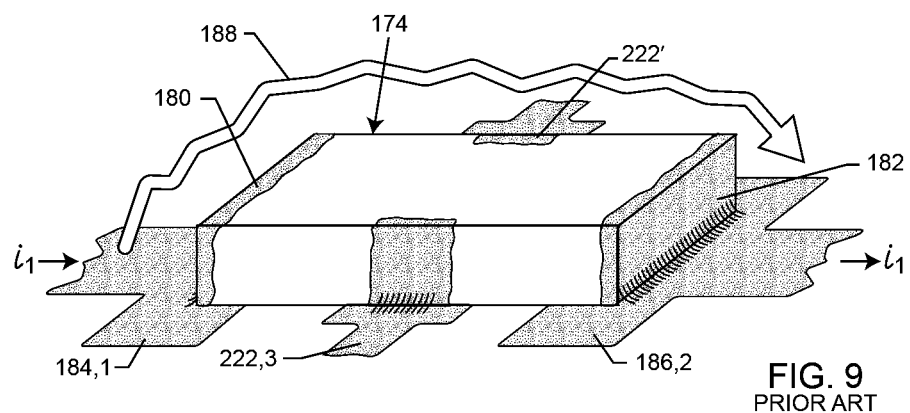
FIG. 9 is an oblique view of a prior art flat-through capacitor.
Figure 10:
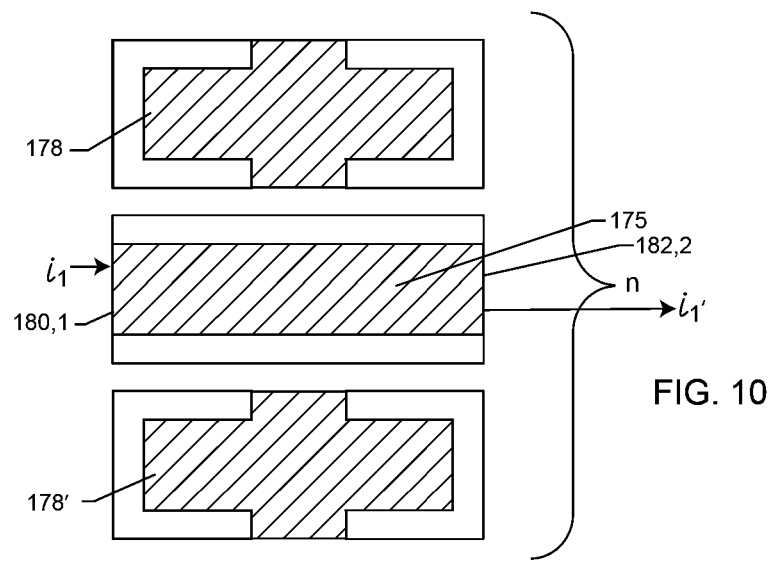
FIG. 10 is a sectional view showing the internal electrode arrays of the flat-through capacitor of FIG. 9.
Figure 11:
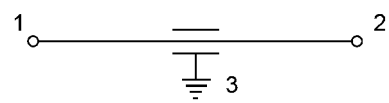
FIG. 11 is an electrical schematic diagram of the prior art flat-through capacitor of FIGS. 9 and 10.

As shown in the drawings for purposes of illustration, the present invention is concerned with shielded three-terminal flat-through EMI/energy dissipating filters 190 which can be embodied in substrates or flex cable assemblies. The novel concept resides in designing an embedded flat-through capacitor wherein optional surface mounted passive or active components can be attached while at the same time providing an interconnection circuit. The novel shielded three-terminal flat-through EMI/energy dissipating filters 190 of the present invention provides three-terminal capacitive filtering while simultaneously providing shielding of circuits and signals passing through the robust high current capability electrodes of the flat-through capacitor. In so doing, the flat-through EMI/energy dissipating filter 190 of the present invention preserves functionality expected of feedthrough capacitors, namely: a) its internal ground plates act as a continuous part of the overall electromagnetic shield housing of the electronic device or module which physically blocks direct entry of high frequency RF energy through the hermetic seal or equivalent opening for lead wire ingress and egress in the otherwise completely shielded housing (such RF energy, if it does penetrate inside the shielded housing, can couple to and interfere with sensitive electronic circuitry); and, b) like prior art feedthrough capacitors, the flat-through EMI/energy dissipating filter 190 of the present invention very effectively shunts undesired high frequency EMI signals away from the lead wire (electrodes) to the overall shield housing where such energy is dissipated in eddy currents resulting in a very small temperature rise. However, unlike prior art discoidal/feedthrough capacitors, in the present invention, the circuit currents (for example, pacemaker pacing pulses or ICD HV defibrillation high current shocks) must pass through the internal electrodes of the embedded flat-through capacitor. By incorporating flat-through technology into circuit board, substrate or flex cable technologies, the flat-through electrodes can be manufactured with much thicker electrodes (like copper sheet), thereby providing increased capability to safely carry relatively higher through-circuit currents (such as those delivered by external or internal cardiac defibrillation pulses).

Figure 13:
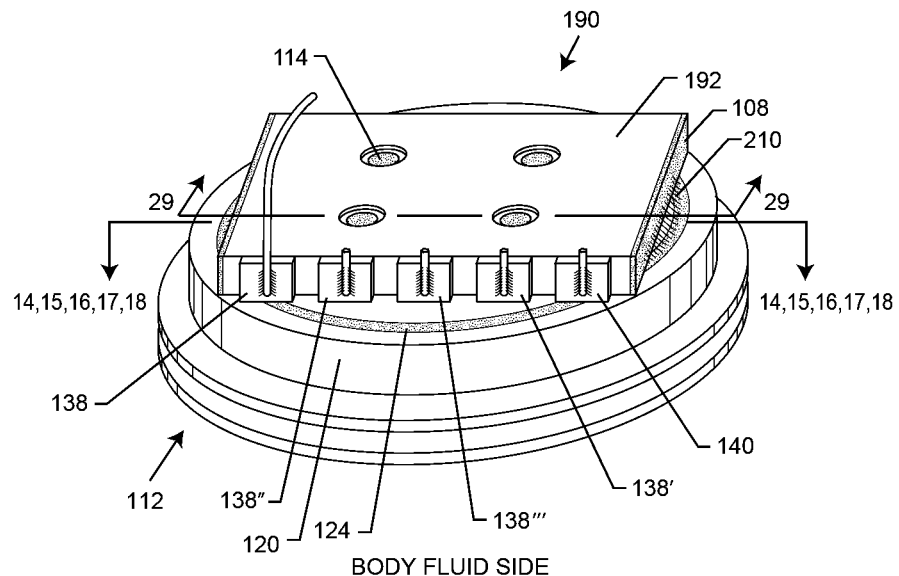
FIG. 13 is an oblique view of a quadpolar EMI filter hermetic seal embodying a shielded three-terminal flat-through EMI/energy dissipating filter of the present invention with a novel platinum filled via in a hermetically sealed feedthrough of the present invention with an external metallization connected to the ferrule.

FIG. 13 is a quadpolar EMI filtered hermetic seal in accordance with the present invention. The feedthrough capacitor element present in the prior art has been completely eliminated. Additionally, the feedthrough capacitor and any associated wire bond substrate that may be present have been replaced by a novel shielded three-terminal flat-through EMI/energy dissipating filter 190. In FIG. 13 pads 138, 138', 138", 138''' and 140 are wire bond pads that are attached to a relatively higher k ceramic or suitable hybrid substrate 192. Novel parasitic flat-through capacitors of the present invention are integrated into the substrate 192. This is better understood by referring to FIGS. 14 through 18.

Figure 14:
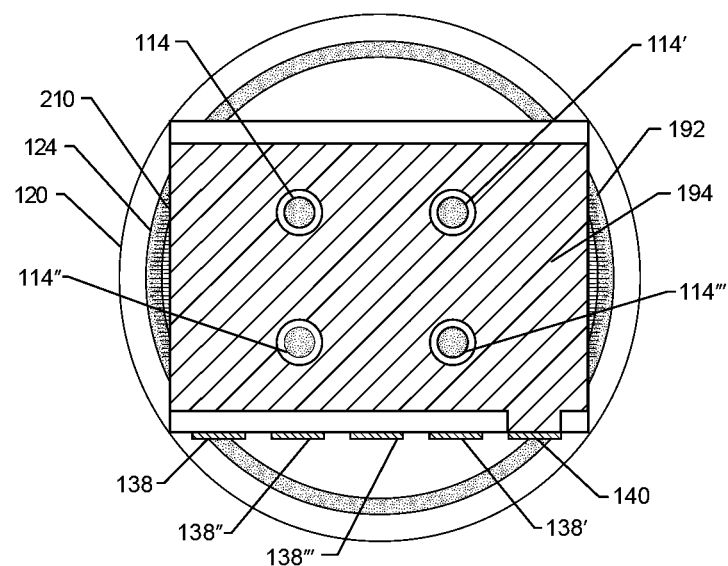
FIG. 14 is a sectional view taken generally along the line 14-14 of the structure of FIG. 13.

FIG. 14 illustrates a grounded shield plate 194. The flat-through electrodes, whether ground electrode plates or active electrode plates, can now be manufactured with much thicker electrodes, thereby providing increased capability to safely carry relatively higher through-circuit currents such as those delivered by external or internal cardiac defibrillation pulses. The grounded shield plate 194 is actually part of a set of grounded shield plates. These shield plates are electrically connected to metallization surface 108, as illustrated in FIG. 13 that are shown disposed on the two ends of the shielded flat-through capacitor of the present invention. It will be appreciated that this metallization 108 could wrap around the back of the shielded flat-through capacitor structure (not shown). The presence of this metallization 108 forms an effective edge shield or faraday cage, such that, EMI that would enter on pins 114 from the body fluid side, would be effectively decoupled by the capacitance of the shielded flat-through capacitor and not be able to re-radiate to sensitive circuits inside the AIMD housing. An effective ground connection is made from metallization surface 108 to the gold braze 124, which also forms the hermetic seal between the alumina ceramic 118 and the ferrule 120 of the hermetic insulator assembly 112. Electrical connection material 210 forms electrical connection between metallization 108 and gold braze material 124. Electrical connection material 210 can be a thermal-setting conductive adhesive, a thermal-setting conductive polyimide, a solder, braze, weld or the like. In any event, electrical connection material 210 forms a very low impedance and solid RF grounding path between ground electrodes 194 through metallization 108 and in turn, to the gold braze 124, which forms an oxide-free metallurgical bond to the hermetic seal ferrule 120. The hermetic seal ferrule 120 is typically laser welded to the housing 116 of an AIMD (not shown).

FIGS. 15 through 18 illustrate the internal active electrode plate layouts 176, 176', 176" and 176'''. The overlap area which is otherwise known as the effective capacitance area (ECA) of each of these active electrode plates has been maximized in order to maximize the flat-through capacitance. Maximizing the thickness and the area of the active electrode plates 176-176''' also has an added benefit in that their overall resistance is lowered (and its current rating is greatly increased). This is important because circuit currents of the novel shielded three-terminal flat-through EMI/energy dissipating filter 190 must pass through the respective electrode plates 176-176''' in order to accomplish the novel shielded flat-through capacitor characteristics.

The present invention differentiates itself from prior art capacitor technologies in that the electrode plates in both the flat-through and the feedthrough prior art capacitors have maximum thickness limitations due to manufacturing processing capabilities. Additionally the capacitor electrode thickness limitations of prior art capacitors results in relatively high series resistance, hence restricts rated amperage to a few milliamps, or at best, a few amps. In the case when a lead implanted in a patient is either exposed to an external (AED) defibrillation pulse or is coupled to an implantable defibrillator, the lead must sustain high voltage current pulses of over 20 amps. The novel shielded three-terminal flat-through EMI/energy dissipating filter 190 of the present invention overcomes the effects of the capacitor thickness limitation by incorporating grounded shield plates 194 surrounding, on at least the top and bottom sides, to provide a novel high surface area and high cross-sectional area with a relatively thick flat-through active electrode plate 176 through which currents of up to even 30 amps or greater can pass. The circuit traces and electrodes in a multilayer rigid or flexible substrate of the shielded three-terminal flat-through of the present invention can be much thicker as compared to the example prior art capacitor electrodes by leveraging circuit board or hybrid flex cable technology wherein the conductive circuit traces can be many orders of magnitude thicker. In fact, the electrode/circuit trace thickness of the present invention may be 4 to even 50 times that the thicknesses typical of prior art capacitors. Referring once again to FIGS. 15 through 18, it is important to note that the flat-through capacitor electrodes are not only capacitive electrodes, but also function as circuit current carriers, meaning biologic therapeutic pulses, biologic sensing signals and the like pass through the electrodes themselves as they traverse between the hermetic seal and internal AIMD circuit boards. Furthermore, as will be seen in subsequent drawings, the novel high surface area electrodes 176 of the shielded three-terminal flat-through EMI/energy dissipating filter 190 of the present invention may additionally include inductor sections which not only desirably add series inductance to the filter but also increase the flat-through capacitance by increasing the effective capacitance area (ECA). Another differentiator from the prior art capacitor technology involves conductor configuration. With prior art capacitors, circuit currents pass through leadwires that extend through the thickness of the capacitor. Moreover, for feedthrough capacitors, the capacitor electrodes are capacitive only, and circuit currents never pass through the electrode plates. The only currents that would flow in feedthrough capacitor electrode plates are capacitor charging and discharging currents as the voltage at the capacitor varies. The solid leadwire of the prior art is replaced with a solid platinum filled via hole in the present invention. The platinum filled via hole extends through the thickness of the alumina insulator 114 in hermetic relation. Circuit currents pass through the solid filled via hole.

Referring to the novel construction as illustrated in FIGS. 13 through 19 and FIG. 29, the flat-through capacitance is shown to be exceptionally shielded. In this novel design, ICD pulse current pass through the Pt filled vias and then through the electrode plates 176-176'''. As current passes through the electrode plates, it spreads out through the entire plate for a low DC resistance generally equal to or less than 20 mohms. Additional active plates 176 and ground plates 194 may be added to drive down ESR, or alternatively, double active electrode plates 176 can be placed between two ground plates as is taught in U.S. Pat. No. 5,978,204 which is incorporated in full herein with this reference.

As discussed in U.S. patent application Ser. No. 13/743, 254, parasitic RF cross-coupling is undesirable in active medical devices. Hence, the exceptional shielding in the present invention provides for the flat-through capacitance to act as an ideal capacitor without resonances and parasitic RF cross-coupling degradation.

Figure 20:
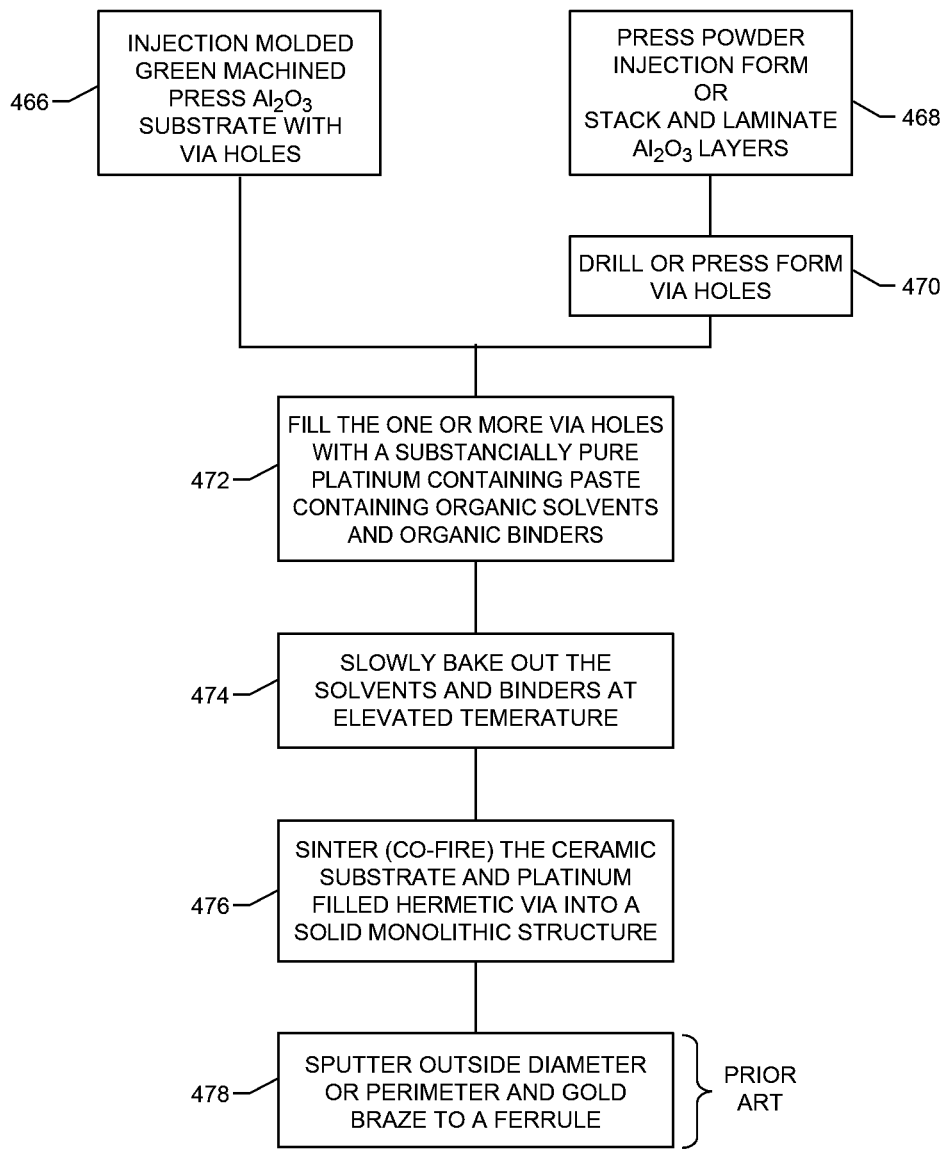
FIG. 20 is a flow chart illustrating the main steps of one embodiment of the process of the present invention.

FIG. 20 is a flow chart illustrating the main steps of the process of the present invention. First, an essentially high purity alumina substrate is formed either through injection molding, green machining, powder pressing 466, by pressing powder into an injection die, or by tape casting and then stacking and laminating individual layers into a bar 468. After formation of the bar in step 468, the via holes 470 are formed. All of the via holes would be filled in step 472 with an essentially pure platinum paste containing organic solvents and organic binders. As used herein, "essentially pure" means essentially pure post-sintering once the bulk of the binders and solvents have been baked out in step 474 and/or sintered in step 476. Once the binders and solvents have been driven out of the system and sintering 476 has occurred, the result is a solid monolithic high purity alumina substrate 488 with one or more pure platinum via holes 486 extending from an alumina substrate 488 outer surface to an inner surface. The outside diameter or the perimeter of the alumina substrate can now be prepared for attaching a ferrule 422. In the present invention, the ferrule 422 is attached using conventional prior art techniques. That is, the outside diameter or perimeter of the sintered alumina substrate 488 is metalized (sputtered). Then the ferrule is attached to these metalized ceramic layers through a gold brazing process 478 wherein, pure gold is reflowed such that it wets the titanium ferrule and also wets to the metallized surfaces that were previously sputtered onto the alumina ceramic. Refer to U.S. patent application Ser. No. 13/743, 254, FIG. 12 detailed description, for more specifics regarding the process steps used in the present invention.

Figure 21:
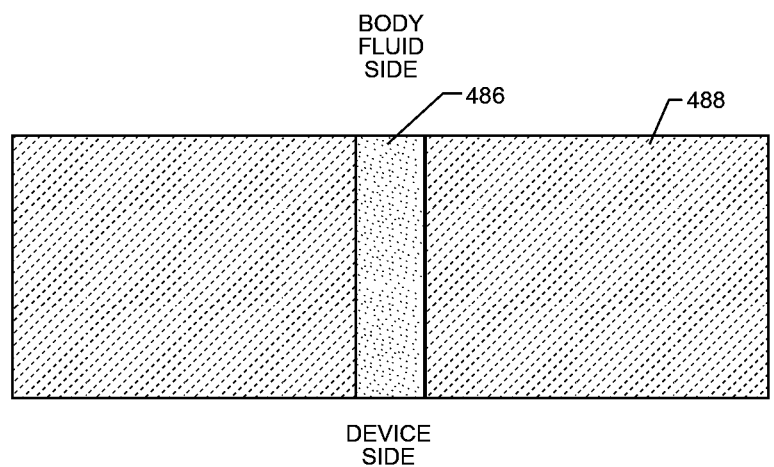
FIG. 21 is a sectional view of a hermetic terminal assembly of the present invention comprising a high purity alumina ceramic and a pure platinum filled via hole in a green state.
Figure 22:
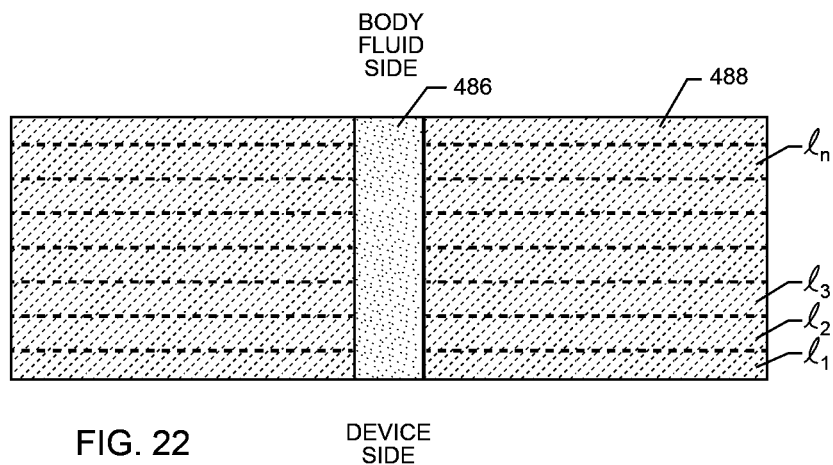
FIG. 22 is another sectional view of a hermetic terminal assembly of the present invention now showing stacking build up from individual tape layers in a green state.

FIGS. 21 and 22 are simplified unipolar sectional views (without ferrules) showing the essentially high purity alumina ceramic 488 of the present invention with a pure platinum via hole 486.

Figure 23:
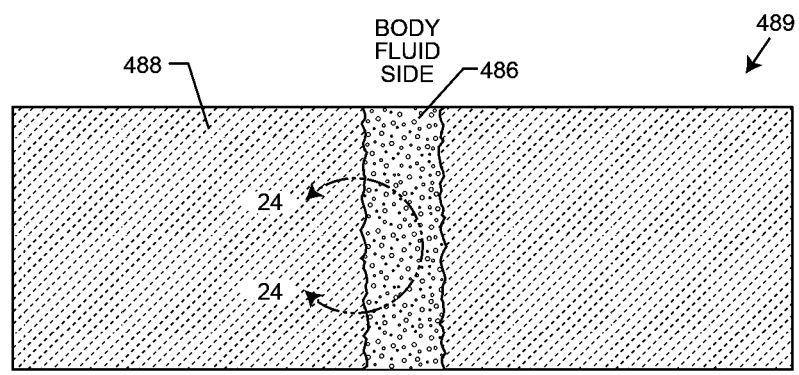
FIG. 23 is a sectional view of the hermetic terminal assembly of FIGS. 21-22 after a co-firing process.

FIG. 23 illustrates a co-fired high purity alumina hermetic terminal subassembly with pure platinum filled vias 486 of the present invention. The pure platinum fill 486 forms a tortuous, intimate and mutually conformal interface 491 between the alumina dielectric insulator substrate 488 and the platinum fill 486.

Figure 24:
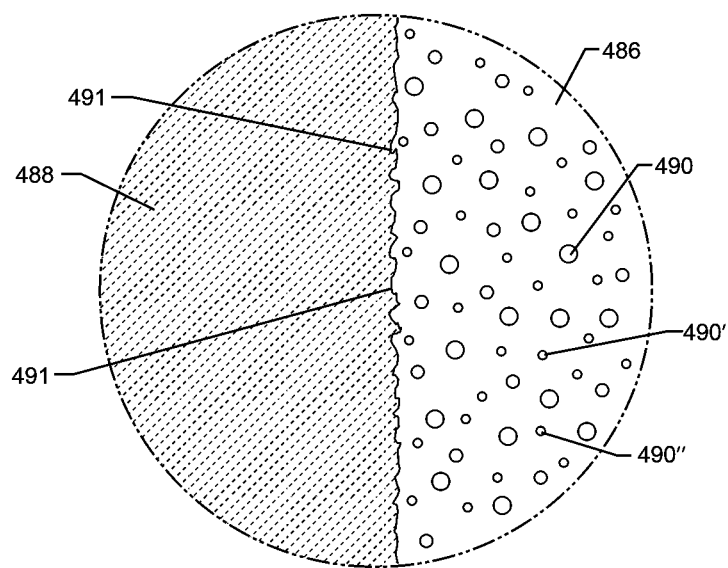
FIG. 24 is an enlarged view of the structure of FIG. 23 now showing a mutually conformal interface (or tortuous, intimate knitline)

FIG. 24 is taken from section 24-24 from FIG. 23 and shows the post-sintered condition wherein the platinum via 486 and the alumina ceramic 488 form a tortuous, intimate, mutually conformal interface 491. The ridges and valleys that exist between the two surfaces of the interface 491 form an intimate structure capable of withstanding compressive, tensile and sheer stresses. This is a result of a greatly increased contact surface area between the sintered alumina substrate material and the sintered pure platinum fill 486. This greatly increased contact surface area improves the overall strength and helps sustain hermeticity of the pure platinum-filled via hole. Helium leak rates of no greater than $1\times10^{-7}$ std cc He/sec are readily achieved using this novel process. In preferred embodiments, the helium leak rate would be no greater than $1\times10^{-8}$, $1\times10^{-9}$, $1\times10^{-10}$, $1\times10^{-11}$ or even $1\times10^{-12}$ std cc He/sec.

Another important feature of the present invention is closed cell porosity 490, 490', 490" in the pure platinum 486 as best illustrated in FIG. 24, which is a sectional view taken from section 24-24 from FIG. 23. When the present invention is sintered, a dense filled via with carefully controlled, well distributed, closed-cell pores 490 forms. The presence of these pores are not contiguous, and hence do not compromise the hermeticity of the overall via structure 486. Also, given that a dense filled via forms, these pores are relatively few in number so they have minimal, if any, effect on the overall resistivity of the via hole from one end to the other.

FIGS. 25 through 28 are embodiments of novel hermetic seals of the present invention. In each embodiment, the outside diameter of the alumina hermetic insulator 488 has metalized surfaces 452 and 450, which are adhesion (452) and wetting (450) surfaces so that gold braze 440 can be melted and hermetically bonded to the alumina hermetic insulator 488 and the ferrule 422 of the hermetic terminal assembly 489. The ferrule 422 may be installed into the AIMD housing 402 by laser welding 428, or the like. It is an important goal of the present invention to eliminate the highly expensive biocompatible and noble leadwires 418. It is apparent in FIGS. 2 through 28 that instead of a feedthrough leadwire, the present invention comprises via hole 486 that is filled to one degree or another with a pure platinum paste. It is a novel feature of the present invention that this via hole material 486 be of essentially pure platinum and is co-fired with the essentially high purity alumina ceramic substrate 488.

Figure 25:
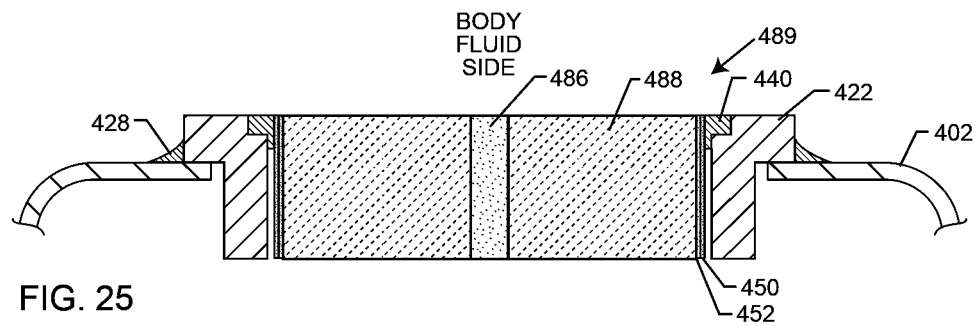
FIG. 25 is a sectional view of an embodiment of a novel hermetic terminal subassembly of the present invention installed in a housing of an AIMD.
Figure 26:
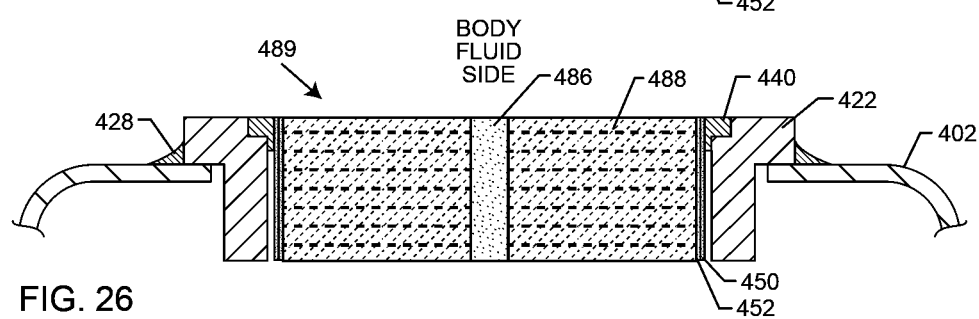
FIG. 26 is a sectional view similar to FIG. 25 showing individual tape layers comprising the insulator.

FIG. 26 is similar to FIG. 25 except that the ceramic body 488 has been laid down in individual tape layers. After sintering, these individual layers form a monolithic structure and are very difficult, if not impossible, to discern.

Figure 27:
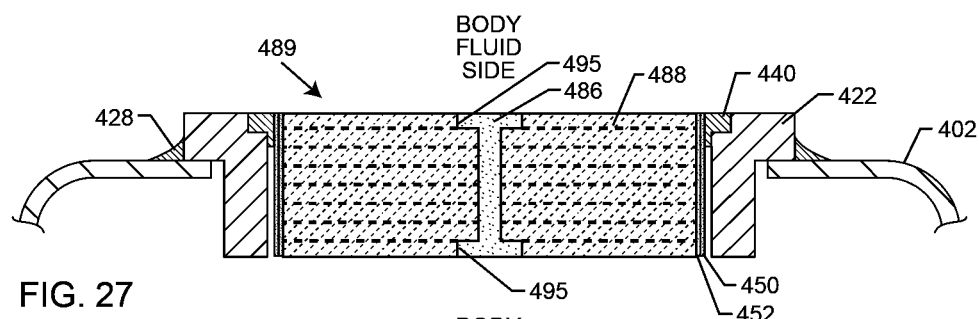
FIG. 27 is a sectional view similar to FIGS. 25 and 26 now showing the platinum filled via with a smaller diameter center section as compared to the ends of the platinum filled via.

FIG. 27 is very similar to FIGS. 25 and 26 except that the novel platinum filled via hole 486 has counter-bores 495 shown on both ends. It will be understood to those skilled in the art that these counter-bores 495 could be counter-sinks, counter-bores or any shape and they could be at both the top and the bottom of the substrate surfaces as shown. They could also be just on one side of the substrate (not shown). This permits use of a very thin diameter via hole which saves on the amount and expense of pure platinum while at the same time provides a large surface area for a ball grid array attachment, for example, of a feedthrough capacitor as will be described in subsequent drawings.

Figure 28:
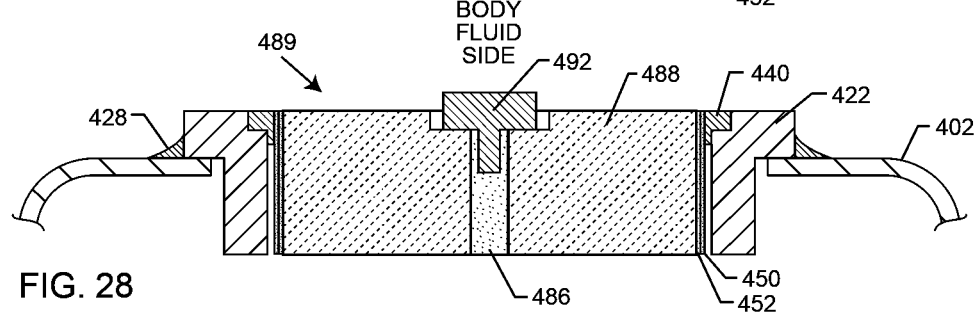
FIG. 28 is a sectional view similar to FIGS. 25, 26 and 27 now showing a wire bond cap co-fired into the platinum filled via.

FIG. 28 is very similar to FIGS. 25 and 27 except that a novel wire bond cap 492 has been placed on top of the via hole 486. In a preferred embodiment, this wire bond cap 492 could be of similar compatible metal, like pure platinum, such that it could be co-fired, to electrically and mechanically connect to the via hole fill material 486. This wire bond pad 492 can be placed on the top side as shown, or the bottom side, not shown, or both sides depending on the application and how wires, ribbons or other conductor material would be routed to an implanted lead, an AIMD connector-header block, or the like. The novel cap 492 of FIG. 28 can be set into a counter-bore hole as shown or it can be set flush or proud on the top surface of the alumina 488, or any variation thereof. Referring once again to FIG. 28, an implantable lead conductor could be connected to a wire bond pad 492 located on the body fluid side. In general, the implantable lead conductor or header block leadwire 418 would have a distal electrode in contact with biological cells.

U.S. patent application Ser. No. 13/743,254 provides detail surrounding hermetic terminal subassembly structures and constructions from which the novel invention within distinguishes itself. Essentially, U.S. patent application Ser. No. 13/743,254 discloses that the prior art does not teach the creation of mutually conformal interface or tortuous, intimate knitline between the alumina and the platinum wire nor the significance of the invention within this application for reliable and sustainable hermetic performance. Also taught by the invention within U.S. patent application Ser. No. 13/743,254 is the mechanism behind hermetic failures in device feedthrough terminals and the structure and methods for providing a hermetic terminal structure capable of reliably sustainable hermeticity. Thus, the invention discloses three enabling areas: (1) via packing with a high solids loading in the paste, (2) compression by the ceramic of the metal paste during binder bake out and sintering, and (3) a controlled cool down rate in combination with interfacial bonding sufficient to tolerate coefficient of thermal expansion (CTE) mismatch, all of which are of significance in the present invention.

Figure 29:
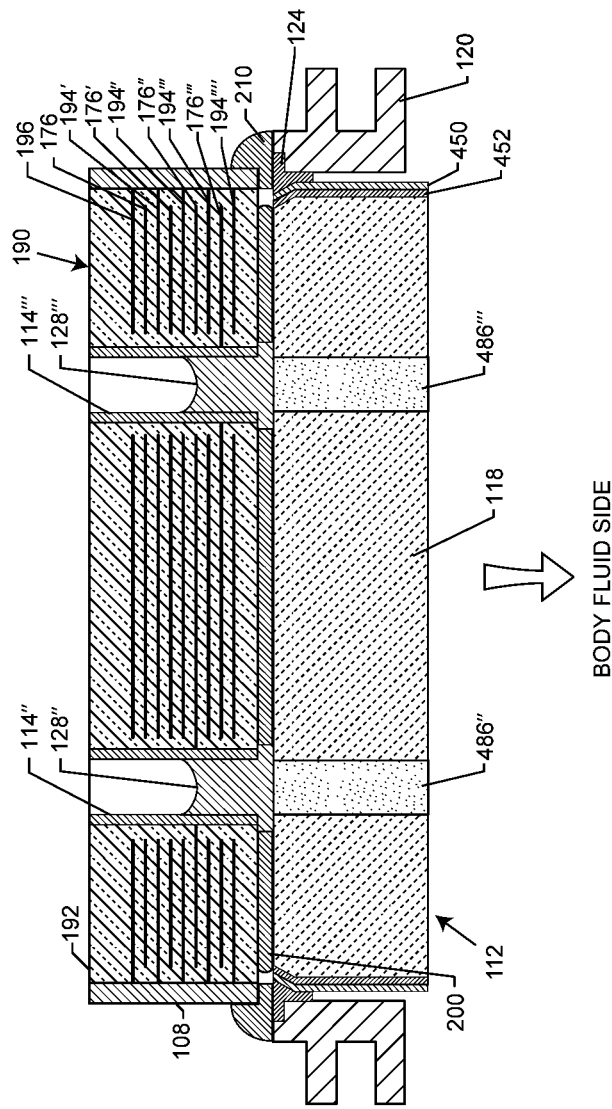
FIG. 29 is a sectional view of the structure of FIG. 13 taken along lines 29-29.

FIG. 29 is a sectional view 29-29 taken from FIG. 13. One can see the ferrule 120 and the gold braze 124 in cross-section along with electrical connection material 210. Electrical connection material 210 makes a high RF quality low impedance connection between the flat-through capacitor ground shield metallization 108 and the ferrule 120 of the hermetic seal for the AIMD. Referring once again to FIG. 29, one can see the internal ground electrode stack 194 through 194"" as well as the individual active electrodes. The feedthrough holes for active electrodes 176 and 176' are not revealed by the section line. However, the connection between these electrode plates and the center holes for leads 114" and 114'" cannot be discerned. The sectional line in FIG. 13 does reveal lead holes 114" and 114'". Accordingly, one can discern that their corresponding active electrodes 176" and 176'" have been connected respectively to the appropriate feedthrough holes for 114" and 114'". Referring once again to FIG. 29, one can see that this is indeed a flat-through capacitor, in that, the circuit currents that pass through the hermetic terminal via holes 486 must pass through the active electrode plates 176 of the shielded three terminal capacitor of the present invention. The key difference in the present invention over the prior art is in the presence of the novel shield plates 194. In the present invention, the design and placement of the novel shield plates 194 are intentionally established to specifically become an integral and, more importantly, a deliberate, functionally directed constituent of the overall AIMD electromagnetic shield housing. For example, with an intended construct of the novel shield plates of the present invention, when optionally combined with external metallization shields 108, the present invention, unlike prior art MLCC solutions, consistently prevents re-radiation of EMI or cross-coupling across the filter. As noted earlier, this undesirable cross-coupling is more comprehensively described in U.S. patent application Ser. No. 13/873,832.

Figure 15:
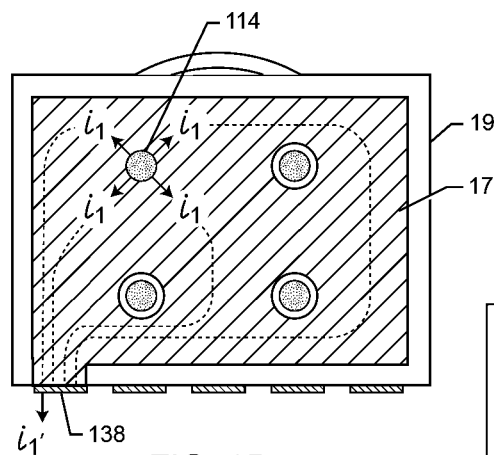
FIG. 15 is a sectional view taken generally along the line 15-15 of the structure of FIG. 13.
Figure 16:
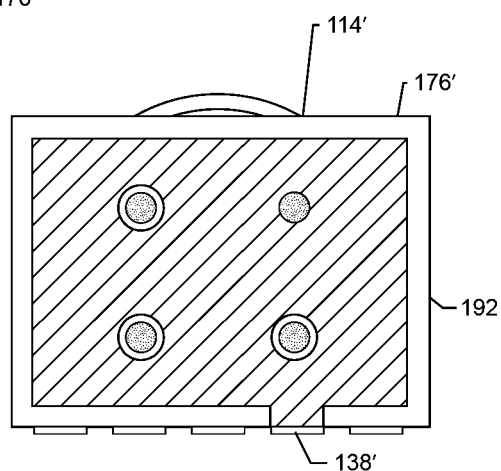
FIG. 16 is a sectional view taken generally along the line 16-16 of the structure of FIG. 13.
Figure 17:
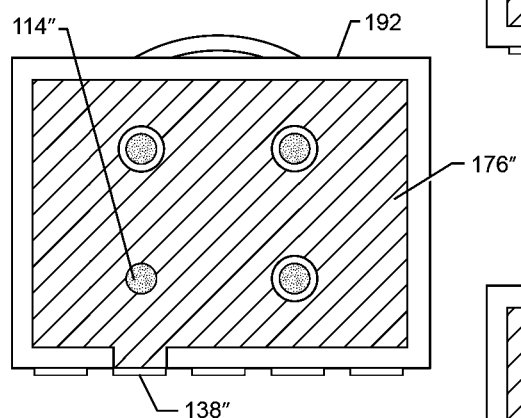
FIG. 17 is a sectional view taken generally along the line 17-17 of the structure of FIG. 13.
Figure 18:
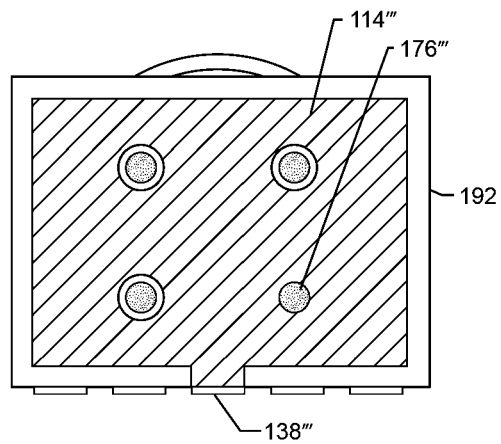
FIG. 18 is a sectional view taken generally along the line 18-18 of FIG. 13.

Referring once again to the shielded flat-through capacitor electrode plates 15 through 18, one can see that these electrode plates not only carry circuit current expected from flat-through capacitor technology but also, these circuit currents can consist of therapeutic pulses, such as pacemaker pulses or biologic sensing signals or the like. FIG. 15 illustrates a circuit current $I_1$ that is entering from the hermetic terminal via hole 114 from the body fluid side into the device housing side and then is connected to an electrode plate 176. One can see that the electrode plate is also conducting the circuit currents $I_1$. As shown, the electrode plate 176 is very wide, which allows the circuit currents to take their paths of least resistance. This means that they will spread broadly and extensively as shown thereby decreasing the overall resistance between point 114 and 138. This, combined with a high cross-sectional area of electrode 176, and unlike the prior art, allows the electrode to carry very high current and have very low voltage drops when it is used in series with the AIMD circuitry in this manner. For example, in designs for implantable cardioverter defibrillators, circuit currents of 30 amps or even greater can be safely handled. Circuit currents have been omitted from FIGS. 16, 17 and 18 for clarity. In prior art flat-through technology, the stack of flat-through, through-electrode plates are attached to circuit lands. The prior art flat-through is not shielded, so when exposed to EMI, the EMI can couple across from one side of the flat-through capacitor to the other. This is a major deficiency of all prior art flat-throughs. In the present invention, the flat-through electrode plates are disposed adjacent the hermetic terminal of an AIMD in such a way that EMI is shielded from coupling from the outside of the device to the inside of the device. This is not only accomplished by the grounded shield plates 194, but is also created by their strategic location which is placed over the hermetic terminals, thereby acting as an EMI shield, which both reflects and absorbs incident or radiated electromagnetic interference.

Figure 19:
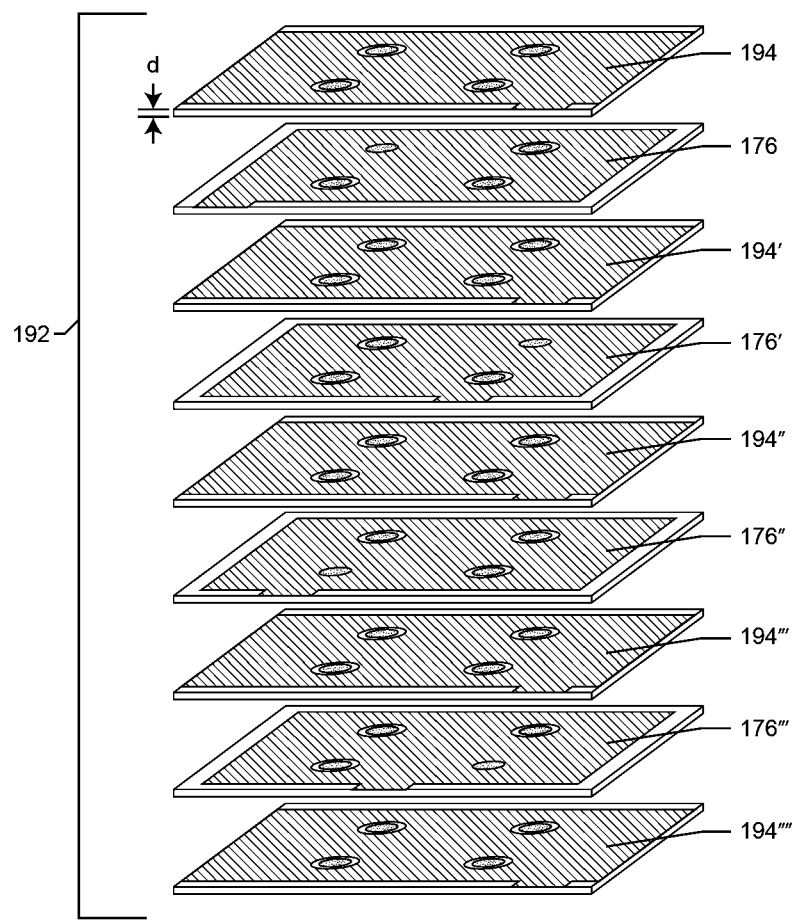
FIG. 19 is an explodedn oblique view of the plates forming the flat-through EMI/energy dissipating filter of FIGS. 13-18.

The overall internal construction of the novel hybrid substrate 192 is best understood by referring to the exploded view shown in FIG. 19. One can see that each one of the flat-through active electrodes 176 through 176''' are sandwiched between a plurality of grounded shield plates 194, 194', 194", 194''', 194'''' and 194''''' as shown. The resulting high ECA has the effect of creating a very high value of flat-through capacitance for EMI filtering (typically several tens or hundreds of picofarads). In contrast, the narrow (low surface area) circuit trace-type flat-through designs taught by U.S. Pat. Nos. 5,683,435 and 6,473,314 limit efficacy of the capacitor electrodes. This results in a flat-through capacitance that is nearly zero (only a stray picofarad which offers no effective EMI filter attenuation by itself).

In addition, by creating the flat-through capacitance between overlapping grounded shield plates 194, the problem that was previously described in connection with the prior art structure has been eliminated. It was shown in U.S. patent application Ser. No. 13/873,832 (FIG. 37) that for a typical prior art flat-through capacitor, there is a frequency at which coupling 188 will occur. This is where the RF signal can, through stray capacitance, antenna action or mutual inductance, avoid passing through electrode plate 175 and instead be coupled directly across the circuit traces or couple to adjacent circuit traces. This is best understood as the degradation in attenuation due to cross-coupling. By shielding the high surface area electrodes 176 of the novel shielded three-terminal flat-through EMI/energy dissipating filter 190 of the present invention with RF grounded shield plates 194 on both sides (and optionally co-planar sides as well), this stray coupling problem and associated high frequency attenuation degradation has been completely eliminated. Again, referring to U.S. patent application Ser. No. 13/873,832 (FIG. 37), one can see that there is really no shield barrier from end-to-end of a prior art flat-through capacitor 174. At some frequency, for example around 100 MHz to 1 GHz, EMI or RF will undesirably cross-couple across the prior art flat-through capacitor 174 or, potentially worse yet, couple to adjacent circuits.

Thus, the significance of the present invention is its novel deliberate construct that overcomes the limitations and resolves the negatives associated with the prior art MLCC solutions. The deliberate construct of the novel shield plates of the present invention may be specifically designed into componentry to address existing, compromising needs unsatisfied by current MLCC technology constructs. Further, the strategic positioning and functionally directed design of the present invention allows outcomes presently not possible with prior art MLCC options. In particular, the present invention, unlike the MLCC prior art solutions, is capable of sustaining high circuit currents that could otherwise damage sensitive device electronics and, in so doing, pose detriment to a patient (such as those to which pacemaker leads are exposed during an external defibrillation event) in addition to simultaneously retaining its ability to shunt EMI reliably. Concurrently, the present invention retains the performance expected of three terminal filtering solutions and also overcomes the manufacturability limitations of prior art MLCC solutions in that the present invention allows simple, convenient mountability. All of the above, independently and collectively, emphasize the uniqueness and nonobviousness of the present invention in its role as an integral constituent of the overall AIMD electromagnetic shield housing.

Figure 30:
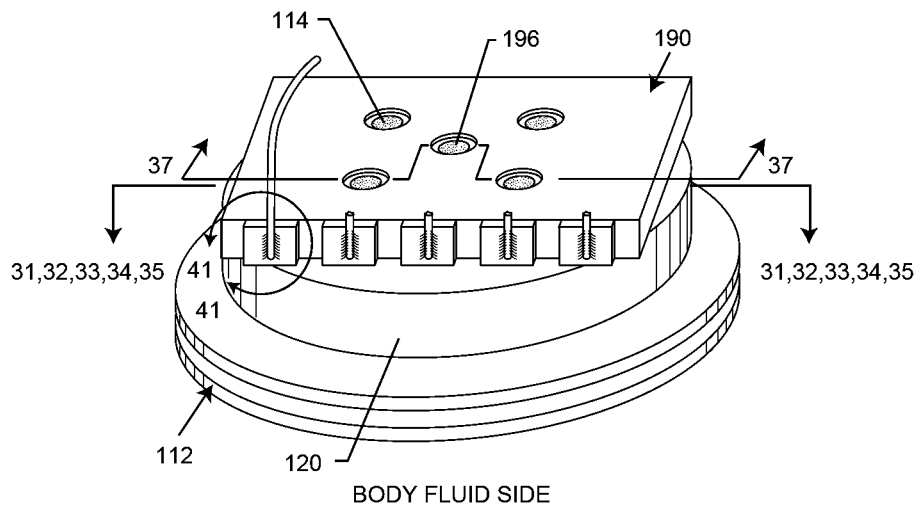
FIG. 30 is an oblique view of a quadpolar EMI filter hermetic seal similar to that shown in FIG. 6, but embodying a shielded three-terminal flat-through EMI/energy dissipating filter of the present invention with a novel platinum filled via in a hermetically sealed feedthrough of the present invention with an internally grounded platinum fill.

FIG. 30 is very similar to FIG. 13 illustrating a novel shielded flat-through capacitor 190 of the present invention, which in this case, is a rigid substrate. It will be shown later that it can also be a flex cable (or flexible substrate). In this case, there is no external ground connection between a metallization 108 and the gold braze or the ferrule of the hermetic terminal or the hermetic terminal ferrule 120. Instead, there is a centered grounded hole 196, which is connected to the internal ground electrode stack 194. This type of internal grounding was previously described for feedthrough capacitors in U.S. Pat. Nos. 5,905,627; 6,529,103 and 6,765,780, the contents all of which are incorporated herein by reference. There are various methods of providing a low impedance RF ground to the ground pin 196 that is illustrated in FIG. 30.

Figure 31:
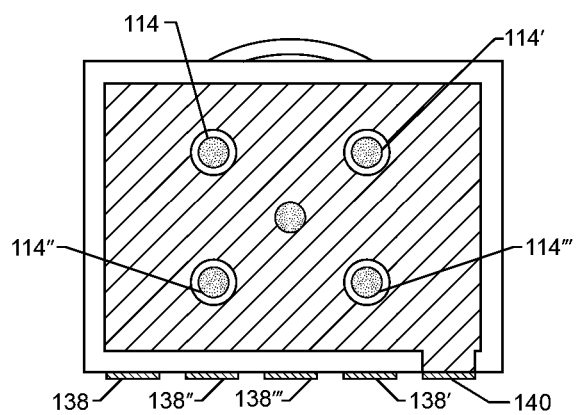
FIG. 31 is a sectional view taken generally along the line 31-31 of the structure of FIG. 30.

FIG. 31 is taken from section 31-31 from FIG. 30. One can see that the grounded center pin 196 has been electrically connected to ground electrode 194.

Figure 32:
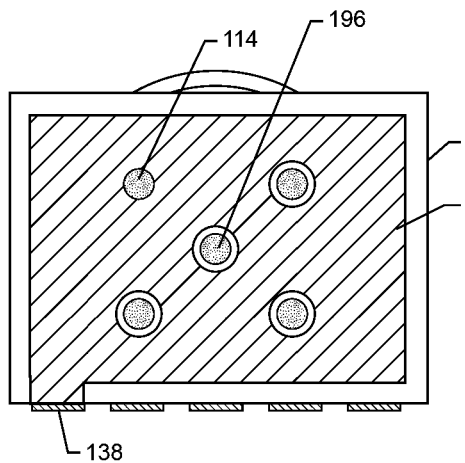
FIG. 32 is a sectional view taken generally along the line 32-32 of the structure of FIG. 30.
Figure 33:
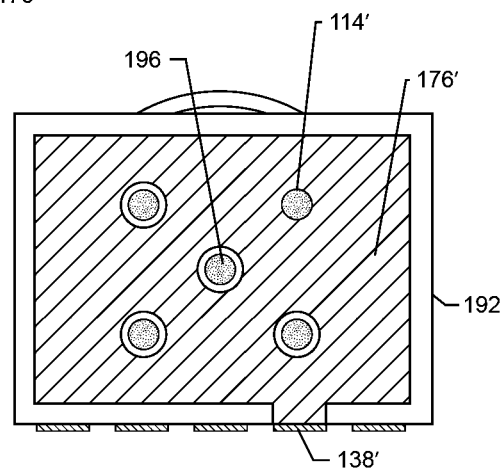
FIG. 33 is a sectional view taken generally along the line 33-33 of the structure of FIG. 30.
Figure 34:
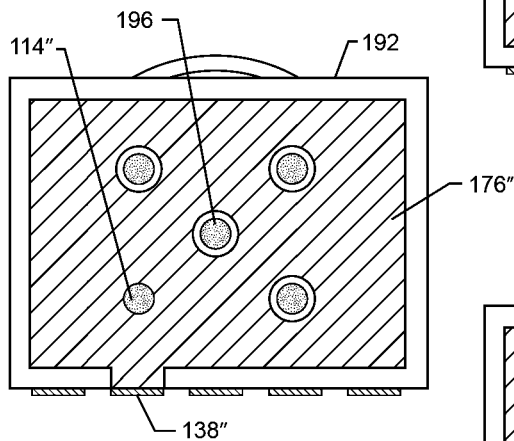
FIG. 34 is a sectional view taken generally along the line 34-34 of the structure of FIG. 30.
Figure 35:
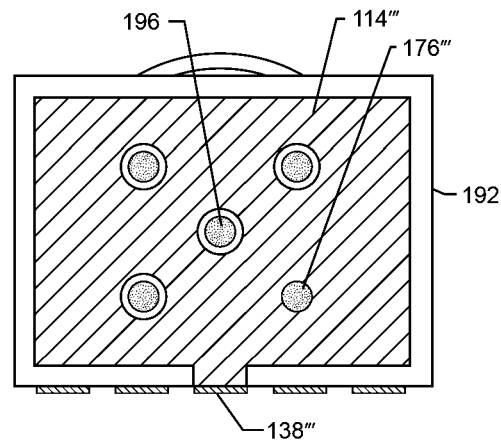
FIG. 35 is a sectional view taken generally along the line 35-35 of the structure of FIG. 30.

In FIG. 32, one can see that the active electrode plate 176 is isolated from the center ground pin 196 (so that it does not short out), but it is connected to active terminal 114 and bond pad 138. Ground bond pad 140 in FIG. 31 is provided for convenient connection to internal AIMD circuitry. In a similar manner, FIGS. 32, 33, 34 and 35 illustrate that each one of the active electrode plates is connected to a respective terminal pin, as illustrated in FIG. 30.

Figure 36:
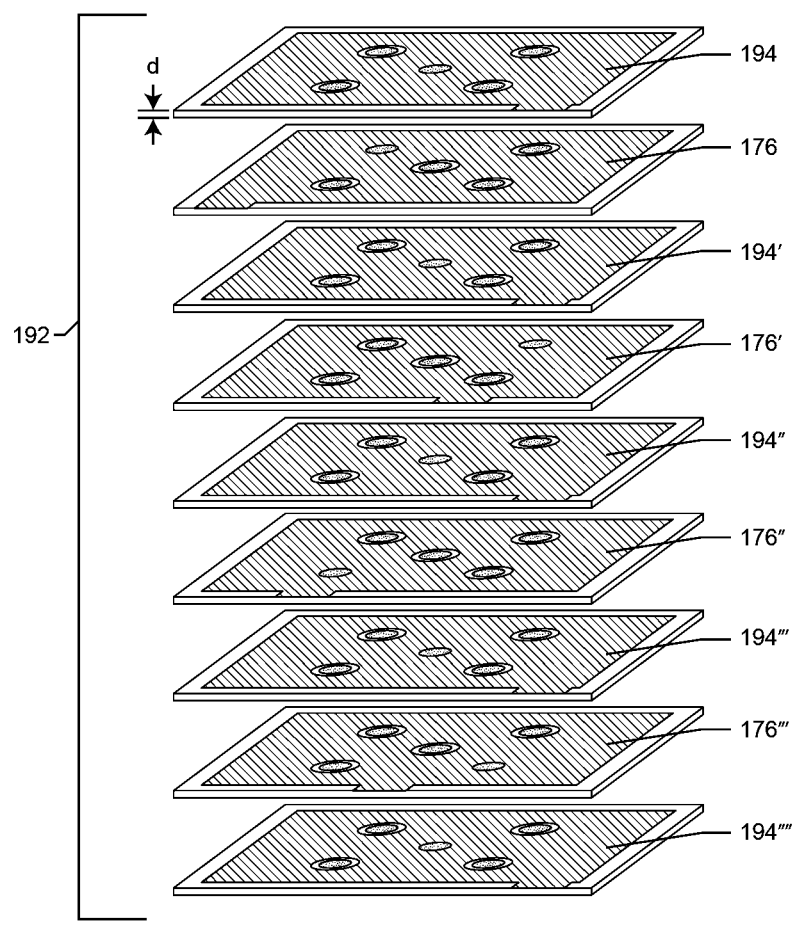
FIG. 36 is an exploded oblique view of the plates forming the flat-through EMI/energy dissipating filter of the structure of FIGS. 30-35.

FIG. 36 illustrates an embodiment of an electrode plate stack up of the novel shielded three terminal flat-through of the present invention. One can see that each one of the active electrodes 176 is sandwiched between ground electrodes 194 in accordance with the present invention. The primary difference between the electrode plate stack up illustrated in FIG. 36 and the electrode plate stack up previously illustrated in FIG. 19 is that in FIG. 36, the ground electrode plates 194 are all internally grounded to a centered ground via 196. In contrast, as shown in FIG. 19 the ground electrodes 194 are directly connected to an external metallization 108 and in turn, to a gold braze of the ferrule.

Figure 37:
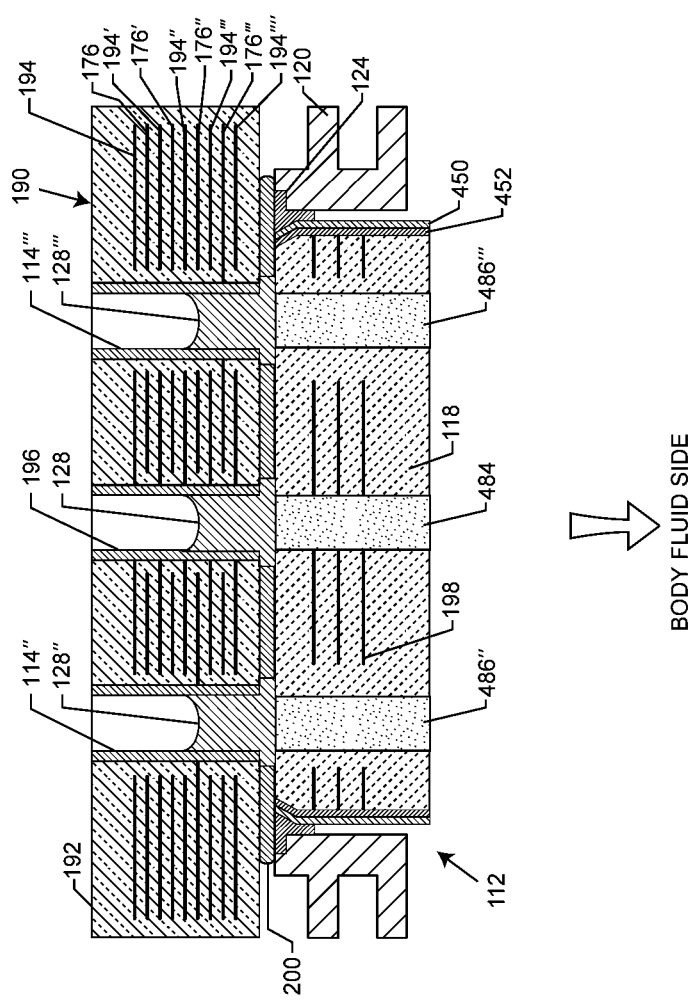
FIG. 37 is a sectional view of the structure of FIG. 30 taken along lines 37-37.

FIG. 37 is a sectional view taken along lines 37-37 from the structure of FIG. 30. FIG. 37 illustrates that the ground electrode plates 194 are internally grounded to the centered ground via 196 and not grounded through an external metallization as was shown and described in FIG. 29. In FIG. 37 the ground electrode plates 194 are grounded internally through the conductive via 128 in the capacitor 190 to then the conductive via 484 in the insulator 118. Electrode plates 198 embedded in the insulator 118 then electrically couple the ferrule 120 to the conductive via 484. It can be seen that the electrode plates 198 do not couple to the active vias 486-486'''. It will also be understood by those skilled in the art that the embodiments shown in FIG. 37 can be combined with those shown and described in FIG. 29.

Figure 38:
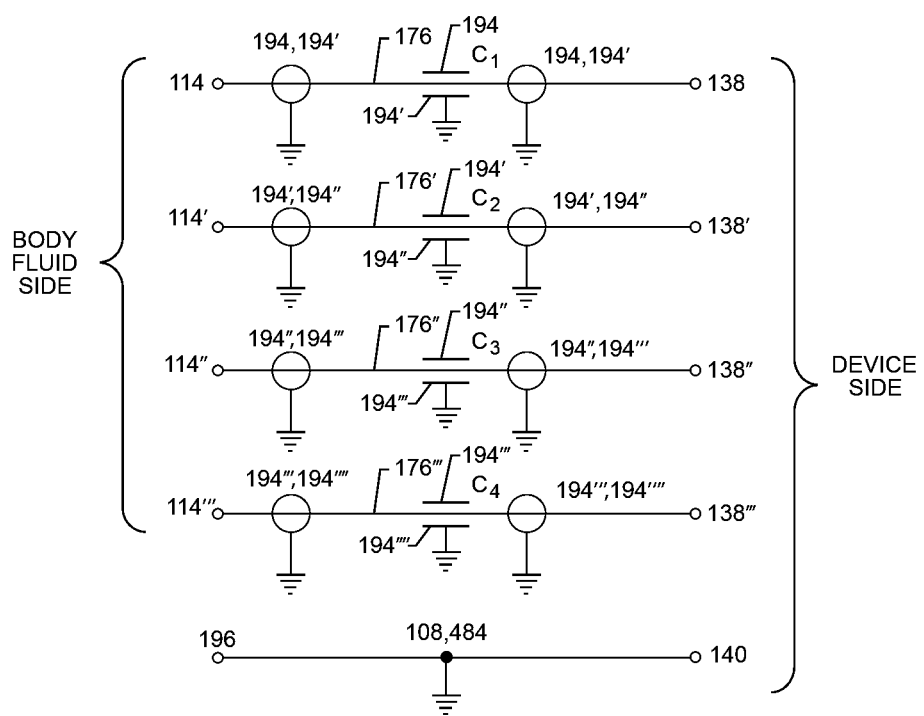
FIG. 38 is an electrical schematic drawing of the flat-through EMI/energy dissipating filter of FIG. 30.

FIG. 38 illustrates an embodiment of a schematic drawing of the novel shielded three-terminal flat-through EMI/energy dissipating filter 190 of FIGS. 13 and 30. Shields 194 through 194'''' illustrate the fact that the high surface area active electrode plates 176 are surrounded at least on top and bottom by grounded shield electrode plates 194 that form the flat-through effective capacitance overlap area and at the same time prevent undesirable RF coupling across the flat-through capacitive filter. The feedthrough capacitances $C_1$, $C_2$, $C_3$ and $C_4$ have been formed by the overlap area (ECA) between each of the active electrodes 176 and the corresponding shield plates 194 that surround the active electrodes on both top and bottom. For example, referring back to FIGS. 19 and 36, one can see that active electrode plate 176-176''' have been surrounded on top and bottom by grounded shield plates 194-194''''.

The grounded shield plates 194'' can be deposited by metal plating, thick film deposition (silk-screening), discrete metal sheets or similar processes on to a dielectric layer which has a specific dielectric thickness d. It is well known to capacitor designers that the formula for the total flat-through capacitance is given by the formula $C=kA(n^{-1})/d$. In this formula, k is the permittivity or dielectric constant of the insulative dielectric material itself; A is the effective capacitance area in $in^2$ or $mm^2$ (ECA) determined by the overlap of the grounded shield plates 194 and 194' and, for example, the active electrode 176; n is the number of total electrode areas; and, d is the dielectric thickness. Referring to FIGS. 19 and 36, an insulative dielectric cover sheets (not shown) may be added which can be the same or different insulating and/or dielectric material that forms the dielectric layer on each of the electrode layers (this is to add additional electrical and mechanical protection). It will be understood to those skilled in the art of designing capacitors that blank cover sheets (as many as needed) could also be inserted between the active electrode layers 176 and the associated or surrounding grounded shield plate layers 194. This would cause the dielectric thickness d to become greater which would have two effects. The first effect would be to increase the dielectric thickness and therefore the voltage rating of the flat-through capacitor. Thin dielectric layers tend to break down at relatively lower voltages. Therefore, for a high voltage application, such as that of an implantable cardioverter defibrillator (ICD), one would want a dielectric thickness that would be relatively greater than say, for example, a low voltage pacemaker. When one examines the equation for capacitance, the dielectric thickness d appears in the denominator. So as one increases the dielectric thickness then the total flat-through capacitance would drop. Accordingly, the first decision a designer makes is what is the required dielectric thickness for the voltage rating of the application and then adjust the ECA such that the desired flat-through capacitance is achieved. In some cases, not enough flat-through capacitance will be achieved to adequately filter all frequencies. As will be described in connection with subsequent drawings, it will be shown how to add, by surface mounting or embedding or thick film deposition, commercially available discrete capacitors, inductors, diodes and other components to enhance its overall performance of the present invention, and in particular, the low frequency (LF) performance of the novel shielded three-terminal flat-through EMI/energy dissipating filter 190.

Figure 39:
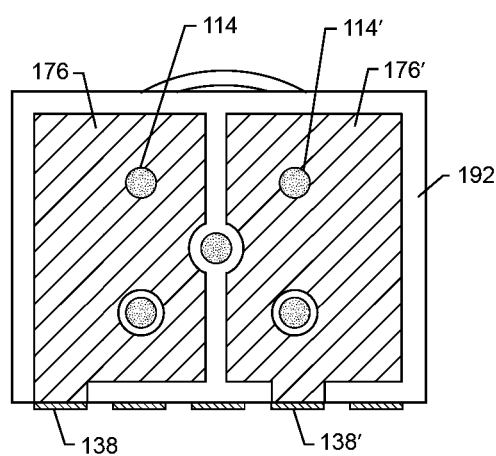
FIG. 39 is a sectional view similar to FIGS. 32-35, now illustrating incorporation of adjacent layers into a single co-planar layer.

Referring now to FIG. 39, illustrated is a way to produce the novel hybrid EMI filter substrate 192 of FIG. 30 with less layers and a correspondingly lower overall substrate thickness. This is accomplished by incorporating two (or more) active electrodes 176 and 176' onto a single co-planar layer. Putting multiple active electrode plates on co-planar layers has the desired effect of making the shielded three-terminal flat-through EMI/energy dissipating filter 190 thinner, easier to manufacture and less expensive. However, this has the undesirable effect of reducing the effective capacitance area (ECA) for each active electrode plate 176 unless high k materials are used. This feature in the present invention provides significant improvement over the prior art in that the effective capacitance area created is so large that efficacy in functionality in accordance with the need is achieved. Subsequent drawings will show methods of adding co-planar inductor-electrodes to boost the filter attenuation. It will be understood to those skilled in the art that in a similar manner, active electrodes 176'' and 176''' could be incorporated into a single combined layer. The novel shielded three-terminal flat-through EMI/energy dissipating filter 190, and particularly its hybrid substrate 192, can be constructed of traditional flex circuit techniques (like polyimide flex circuits), multilayer rigid substrates (like alumina or FR4 board), thick film deposition onto a substrate or carrier, or the like. For each of these manufacturing techniques, there is a practical limit to the number of layers that can be constructed.

As mentioned earlier, this limitation is resultant from limitations in the manufacturing process. In contrast with prior art processing, the construct of the present invention allows the shielded three-terminal flat-through EMI/energy dissipating filter technology to be used in completely flexible substrates, hybrid substrate designs that have both a flexible and a rigid layer, or in a completely rigid board.

Figure 40:
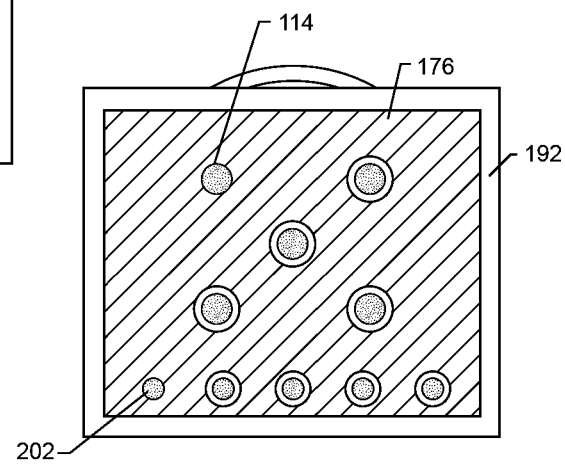
FIG. 40 is a sectional view similar to FIGS. 32-35, now showing modification of the active electrode plates for connection to a via hole.
Figure 41:
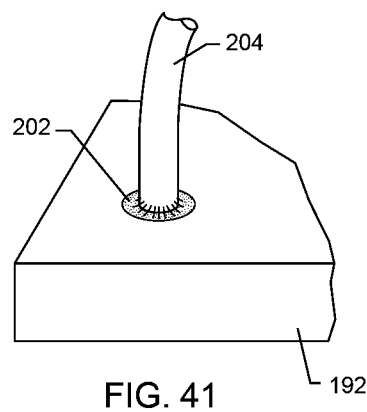
FIG. 41 is a partial oblique view illustrating a lead wire extending into one of the via holes of FIG. 40.
Figure 42:
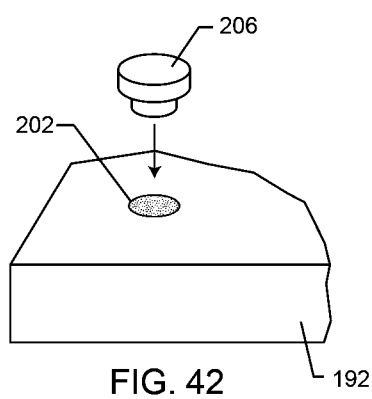
FIG. 42 is a view similar to FIG. 41, now showing an alternative bond pad in place of the wire.

Referring back to FIG. 30, one can see that there are wire bond pads 138 through 140 as shown. The addition of wire bond pads adds a circuit connection convenience. In comparison, FIG. 40, shows that, for example, the active electrode plate 176 shown in FIG. 32 could be modified such that it was connected to a via hole 202. This via hole 202 provides for a convenient connection of either a lead wire 204, as shown in FIG. 41, or a round (or rectangular, square or other not shown) wire bond pad 206 as illustrated in FIG. 42.

Figure 43:
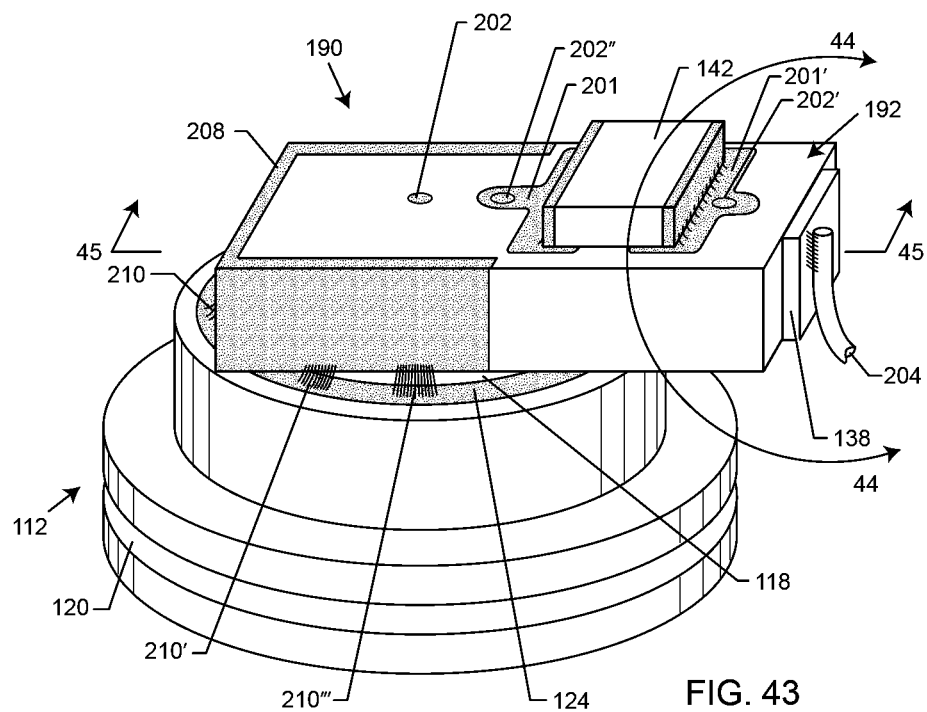
FIG. 43 is an oblique view of a unipolar hermetic seal with a shielded three-terminal flat-through EMI/energy dissipating filter of the present invention.

FIG. 43 is an oblique view of a unipolar pacemaker hermetic seal 112 wherein the prior art feedthrough capacitor is replaced with a novel shielded three-terminal flat-through EMI/energy dissipating filter 190 of the present invention (shown mounted on top of the insulator 118 and gold braze 124). The hybrid substrate 192 of the shielded three-terminal flat-through EMI/energy dissipating filter 190 can be manufactured from any number of the techniques previously described herein. The body of the hybrid substrate 192 could be a conventional substrate consisting of high dielectric constant ceramic, alumina, ceramic, fiberglass, FR4 or any other rigid type of multi-layer board technology. In addition, it could be made of a number of flexible or flex cable variances. These could include flex cables that are laminated together based on polyimide, Kapton and acrylic construction. Another embodiment would be polyimide flex cables with all polyimide connections which are laminated together at high temperature. All of these types of boards and/or substrates and/or flex cables are known in the art. What is described herein is a very novel adaptation of those boards and substrates to flat-through filter technology. Hereinafter, the novel substrates incorporating various forms of novel shielded flat-through EMI filter technologies will be referred to as the hybrid substrates 192.

In FIG. 43, one can see that there is a metalized area 208 on the hybrid substrate 192. This wrap-around metalized area 208 makes connection to internal ground shield plates 194 and 194' embedded within the hybrid substrate 192 as shown in FIG. 45. One can see in FIG. 43 a plurality of electrical connections 210, 210' and 210''' as shown (the equivalent electrical connections 210'' and 210'''' on the opposite side of substrate 192 are not shown). These electrical connections connect to gold braze 124 that is part of the hermetic seal and provides an "oxide-free" RF ground multi-point connection. This is better understood by referring to FIG. 45 which is taken from section 45-45 of FIG. 43. The importance of connecting to a gold braze instead of connecting directly to the titanium ferrule 120 can be better understood by referring to U.S. Pat. Nos. 6,765,779 and 6,765,780 the contents of which are incorporated herein. From FIG. 45, one can see that there is a prior art hermetic seal 112 which includes a metal ferrule 120 which is typically of titanium or the like. There is a flange area 212 shown which is convenient for laser welding to the titanium housing 116 of an AIMD, such as a cardiac pacemaker or the like. There is a hermetic insulator 118 which can be of alumina, ceramic materials, glass or equivalent. In this particular embodiment, there is a gold braze 124 which forms a mechanical and hermetic seal between the insulator 118 and the ferrule 120. In this example, the body fluid side would be towards the bottom of the cross-sectional illustration of FIG. 45. An electrical connection 128 is made between the solid platinum filled via 486 and the metalized 106 via hole 202 which is part of the novel hybrid substrate 192. The via hole 202 makes electrical connection to internal active electrode (otherwise known as the flat-through electrode) plate 176 as shown, which in turn is connected to via hole 202'. The grounded electrode shield plates 194 and 194' are connected to the outside metallization surface 208 of the hybrid substrate 192. In turn, this metallization 208 is electrically connected via material 210 to the gold braze 124 of the hermetic seal 112. As previously stated, this direct connection to gold makes a reliable oxide free low impedance ground connection, the importance of which is described thoroughly in U.S. Pat. Nos. 6,765,779 and 6,765,780. One can also see that by wrapping metallization surface 208 around the sides of the hybrid substrate 192, one prevents any chance that EMI being conducted on active electrode 176 could radiate or cross-couple into the interior of the AIMD. By keeping the EMI "bottled up" between the grounded shield plates 194 and 194', one forms a nearly complete faraday cage shield which is the ideal solution. Due to the thin geometry, substrate edge re-radiation of RF energy is a very minor concern which, if the dielectric thickness between layers 176 and 194, 194' becomes large, can be solved by co-planar edge shields which will be described in connection with FIG. 51. This novel method of shield containment is applicable to any of the embodiments described herein.

Referring once again to FIG. 43, one can see that a prior art monolithic ceramic chip capacitor (MLCC) 142 has been electrically connected to lands 201 and 201' which are in turn connected to via holes 202' and 202''. This is better understood by referring to the exploded view of FIG. 43 shown in FIG. 47. One can see that via hole 202' is connected to the active circuit electrode 176. The other side of the MLCC capacitor 142 is connected by via hole 202'' to both of the grounded shield electrode plates 194 and 194'. It is important that a very low impedance connection has been made to both sides of the MLCC capacitor 142. In this embodiment, any type of chip capacitor could be used. That is, monolithic ceramic, stacked film, tantalum, electrolytic or the like. It will also be understood to those skilled in the art that the ground (left) side of MLCC capacitor 142 need not be connected to RF ground by way of the via 202'' as shown. Instead, an enlarged land 201 on the left side of the MLCC 142 could be RF grounded directly to the external wrap-around metallization surfaces 208.

Figure 44:
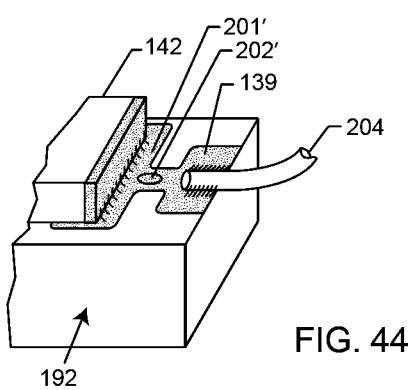
FIG. 44 is an enlarged view of the area indicated by line 44-44 of the structure of FIG. 43, now illustrating an alternative way of attaching a lead wire.

In FIG. 43, one can see that there is a wire bond pad 138 which is affixed to the hybrid substrate 192. This makes for a convenient mounting pad for attachment of lead wire 204. Lead wire 204 would be routed to the internal circuits of the general electronic device or an AIMD. Lead wire 204 can be affixed to wire bond pad 138 by thermal or ultrasonic welding, soldering ultrasonic bonding or the like. FIG. 44 shows an alternative arrangement wherein the wire bond pad 138 (which would typically be made of Kovar) has been eliminated. In FIG. 44, there is a different type of wire bond pad 139 of deposited metal 139 on substrate 192. In this case, there is no separate attachment of a Kovar block 138 is required as illustrated in FIG. 43. In this case, in FIG. 44, wire bond pad 139 can be an integral part of an external circuit trace and deposited by plating, thick film deposition technique and the like.

Referring to FIG. 45, active electrode plate 176 is sandwiched between the two grounded electrode shield plates 194 and 194'. Referring once again to FIG. 45, it will be appreciated that additional active electrode plates 176 can be added and sandwiched between additional ground electrode plates 194. In fact, any number of active and ground electrode plates "n" can be used. The prior art MLCC capacitor 142 is connected between via hole 202' (which is also connected to the active circuit plate 176) and via hole 202'' which is in electrically conductive relationship with both the ground shields 194 and 194'. Electrically speaking, this means that the MLCC capacitor 142 connects from the active circuit plate 176 to ground. Accordingly, it acts as an electrical bypass low-pass filter element to provide additional EMI filtering to complement the flat-through capacitance $C_P$ as previously described.

Referring once again to FIG. 45, one can see that there is an electrical connection material 128 that is disposed between the platinum filled via 486 and the via hole 202. This can be of a thermal setting conductive polymer, such as a conductive epoxy or a conductive polyimide or the like. Material 128 could also be of solder or braze, which is known in the art as solder bump construction or even ball grid array (BGA). It is shown in the reflowed position so it is not obvious that this started out as a round ball. In order to provide electrical isolation between this material 128, one or more adhesive backed insulative washers 200 are disposed between the hermetic seal 112 and the hybrid substrate 192. Typically this washer 200 would be an adhesive backed polyimide or the like to make sure that electrical conductive materials such as 128 stay in place and could not short and/or migrate to areas where they were not desired (like a short to ground). As described in U.S. Pat. No. 7,327,553, the contents of which are incorporated herein by reference, a laminar leak detection path can be provided between the washer 200 to facilitate helium leak testing of the hermetic seal.

There is a similar electrical connection material 210 disposed between metallization surface 208 and gold braze 124. Material 210 is also typically a thermal setting conductive adhesive, solder, low temperature braze, laser weld, or the like. A wire bond pad 138 is shown connected to the active electrode plate 176. At this point, any electrical noise (EMI) that was entering from the body fluid side of the filled via 486 has been decoupled by the filtering action of the flat-through capacitances shown in FIG. 47 as $C_P$ and $C_P'$ and the MLCC 142 working together. The flat-through capacitance is relatively lower in value than the MLCC 142; however, it is very effective for attenuating high frequencies. Lower frequencies are attenuated by the higher capacitance value MLCC capacitor 142. Wire bond pad 138 is convenient for connection of one or more lead wires 204 to internal circuit components inside of the general electronic shielded module or an AIMD.

In FIG. 45, one can see that via hole 202 is connected to the platinum filled via 486 by means of an electrical conducting material 128 which can be solder, a low temperature braze, a thermal-setting conductive adhesive or the like. An alternative methodology is shown in FIG. 46 wherein the via hole 202 is metalized 106 and then attached to a solder bump 216 as shown. The solder bump 216 makes contact to the metallization 106 of via hole 202. By raising the entire assembly to an elevated temperature, the solder bump 216 wets to the platinum filled via 486 forming a reliable electrical and mechanical connection.

Figure 47:
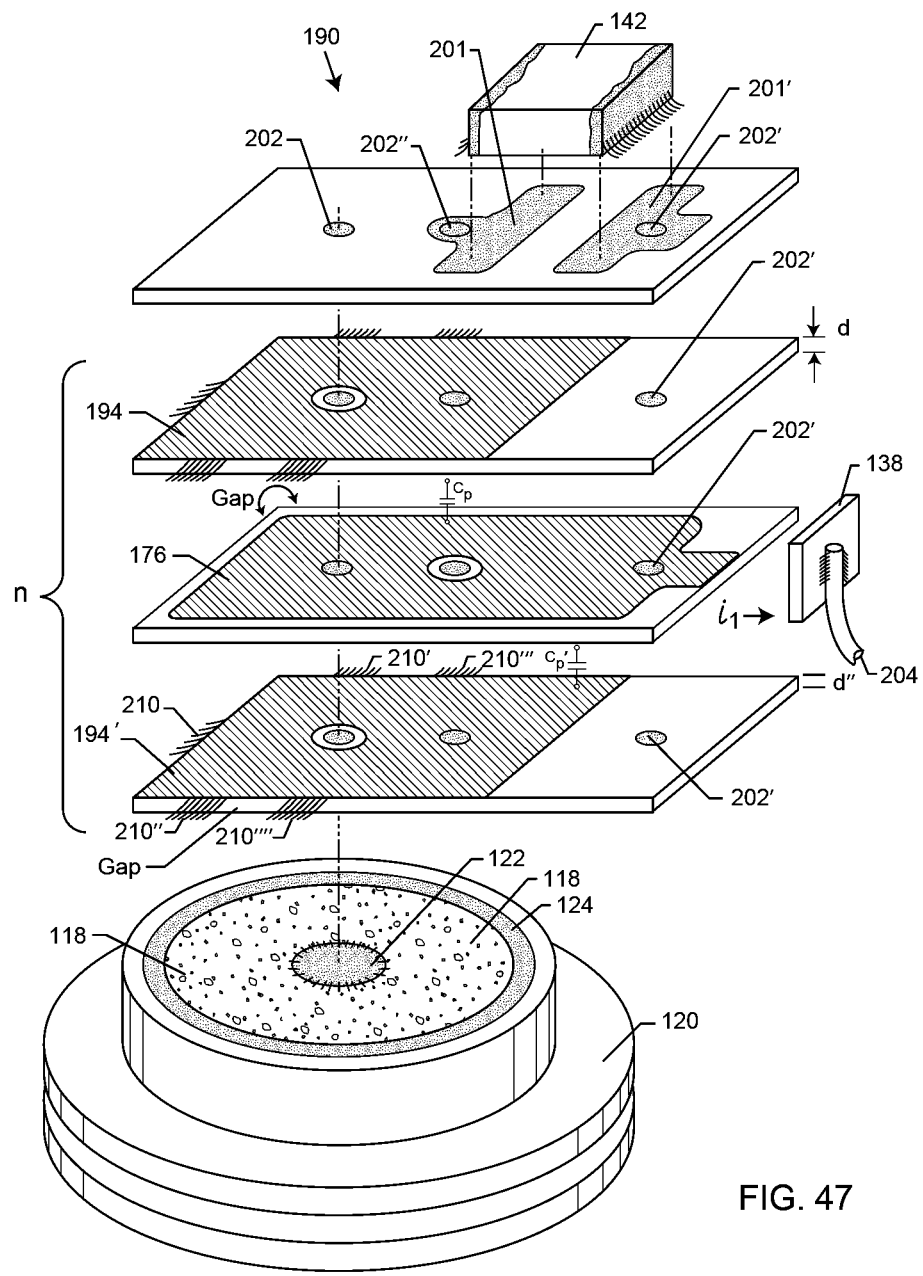
FIG. 47 is an exploded oblique view of various components forming the structure of FIGS. 43 and 45.

FIG. 47 is an exploded view of FIG. 43. A low impedance RF electrical connection to the ground shield plates 194 and 194' is very important. Accordingly, one can see that there are multiple electrical attachments 210 to 210''''. This, of course, could be one long continuous connection all around the ground metallization 208 to the gold braze 124. However, it is desirable to retain a clear path for helium leak testing. The integrity of these hermetic terminals is critical to preclude the entry of body fluid into the AIMD. Accordingly, in the preferred embodiment of the present invention, it is desirable to leave open gaps as shown in FIGS. 43 and 47 between areas of electrical attachment 210. As taught by U.S. Pat. No. 6,566,978, the contents of which are incorporated herein by reference, it will be understood to those skilled in the art that strategically placed open via holes through the hybrid substrate 192 could be provided in order to pass helium during hermetic seal testing.

Referring once again to FIG. 47, a novel aspect of the present invention is that flat-through capacitance develops between the circuit active electrode plate 176 and the surrounding grounded shield electrode plates 194 and 194'. This capacitance is shown as $C_P$ and $C_P'$. The capacitance value of this flat-through capacitance is dependent upon the typical capacitance equation, which is given by $C=kA(\eta-1)/d$, where k is the dielectric constant of the material. As previously mentioned, the novel hybrid substrate 192 shown in FIG. 45 could be constructed of a variety of different materials. For example, the dielectric constant of a polyimide material would be between 3 and 4 whereas an alumina ceramic material could be as high as 9 to 11. Barium and strontium titanate dielectric bodies can have dielectric constants in excess of 5000. In the equation, A stands for the area, which is the effective capacitance area (ECA). This is calculated by the sandwiched overlap between the area of circuit active electrode plate 176 and the corresponding ground electrode shield plates 194 and 194'. Ignoring fringe effects, a simplified way of calculating this area is simply the area of active electrode plate 176 that is bounded between the sandwiched grounded shields 194 and 194'. In the equation, $\eta$ is the total number of repetitive electrode plates. In this case, there are three plates consisting of 194, 176 and 194'. This gives us $\eta-1$ which yields two parasitic flat-through capacitances $C_P$ and $C_P'$. The dielectric thickness d is simply the thickness of the dielectric material that separates 194 and 176; and 176 and 194' as shown. The presence of the flat-through capacitances $C_P$ and $C_P'$ is extremely important to the overall broadband EMI filtering performance of the present invention. This can be understood by referring to the schematic diagram of FIG. 48. It will be understood to those skilled in the art that the higher the amount of the effective capacitance area that overlaps between the active electrode plate 176 and the adjoining ground shield plates 194 and 194', the higher the parasitic capacitance $C_P$ will be. In this case, the parasitic inductance is very small and really does not aide in filtering. It will also be understood to those skilled in the art that the parasitic inductance of the active electrode 176 will be proportional to both its length and its width. In other words, the longer the active electrode 176 is, the greater its inductance $L_P$ will be. The presence of series inductance is very important as this will improve the overall high frequency performance of the shielded three-terminal flat-through EMI/energy dissipating filter 190. There are ways of making this slight series parasitic inductance much higher as will be described below.

Figure 48:
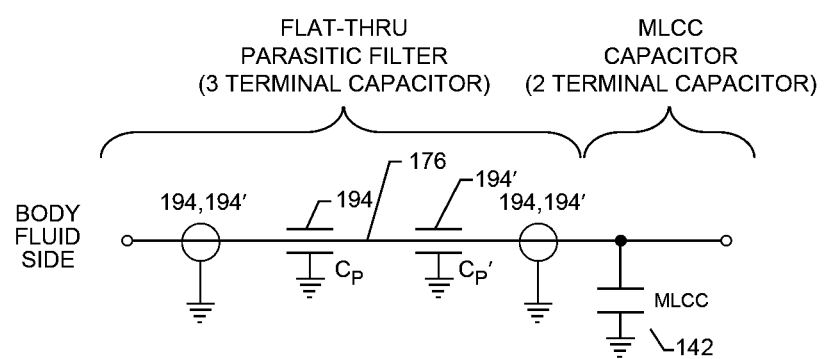
FIG. 48 is an electrical schematic for the structure of FIGS. 43, 45 and 47.

Referring to schematic FIG. 48, one can see that in a number of locations there is a shield symbol 194-194' (sometimes shown as "Sh"). This is an indication that the entire assembly consisting of the flat-through capacitance $C_P$ and $C_P'$ and the capacitance C contributed by the MLCC capacitor 142, in general, has its active electrode all contained (sandwiched between) within the shield plates 194. As previously mentioned, this is very important so that undesirable electromagnetic interference at high frequency cannot bypass or jump across from the body fluid side and thereby enter into the electronic device or AIMD housing and possibly interfere with sensitive electronic circuits. The importance of filtering for AIMDs, such as cardiac pacemakers, has been described by U.S. Pat. Nos. 4,424,551, 5,333,095 and 5,905,627 the contents of which are incorporated herein with these references. In this regard, the shielded three-terminal flat-through EMI/energy dissipating filter 190 of the present invention acts in equivalent way to prior art feedthrough capacitors in that the shielded three-terminal flat-through EMI/energy dissipating filter 190 is not only an effective filter and energy dissipation element, it's ground electrode plates 194 act as an effective part of the overall electromagnetic shield housing of the AIMD or other equivalent shielded electronic circuit.

One way to further increase the total amount of flat-through (parasitic) capacitance would be to increase the number of layers in FIG. 47. In a monolithic construction, repeating the number of redundant layers would increase the capacitance by the η−1 term of the capacitance equation. Additional ways to increase the amount of flat-through capacitance would be to further increase the effective capacitance overlap area ECA, increase the dielectric constant or decrease the dielectric thickness (d).

Prior art feedthrough capacitors typically are very low inductance broadband low-pass filters. In addition, prior art feedthrough capacitors tend to be quite low in capacitance value (primarily in the range from 400 to 4000 picofarads). This means that prior art feedthrough capacitors make very effective high frequency filters above 25 MHz, but off little attenuation at low frequencies (below 5 MHz). Hence, the present invention resolves prior art cross-coupling issues across the flat-through capacitor because it is contained or sandwiched within an entirely shielded structure. It becomes impossible for high frequency EMI to couple across the novel shielded three-terminal flat-through EMI/energy dissipating filter 190 of the present invention. In addition, flex cables for circuit boards are already commonly used in prior art electronic devices including AIMDs. In other words, by not adding any additional structures, one can embed a flat-through capacitance and then combine it with an MLCC capacitor 142 (or additional components) as shown in FIG. 47. The MLCC capacitor 142 is effective for low frequency attenuation and the parasitic flat-through capacitance $C_P$ works to attenuate high frequencies. The parasitic capacitance or flat-through capacitance works in parallel with the capacitance of the discrete MLCC capacitor 142 which results in a very effective broadband low-pass filter from kilohertz (kHz) frequencies all the way to 10 gigahertz (GHz) or higher. This is all summarized by the schematic diagram shown in FIG. 48. Shields 194-194 are illustrative to indicate that the entire flat-through filter is sandwiched between RF shield plates in such a way that high frequency EMI signals cannot re-radiate from the active electrode plate(s) 176. This is a very important concept. Until the undesirable EMI energy is decoupled to ground, it cannot be left unshielded inside the overall electromagnetically shielded housing of the electronic device or AIMD. If left unshielded, such high frequency noise could cross-couple into sensitive AIMD sense circuits. For example, if a cardiac pacemaker senses such high frequency noise as a heartbeat, the pacemaker could inhibit which could be life-threatening for a pacemaker-dependent patient.

Figure 49:
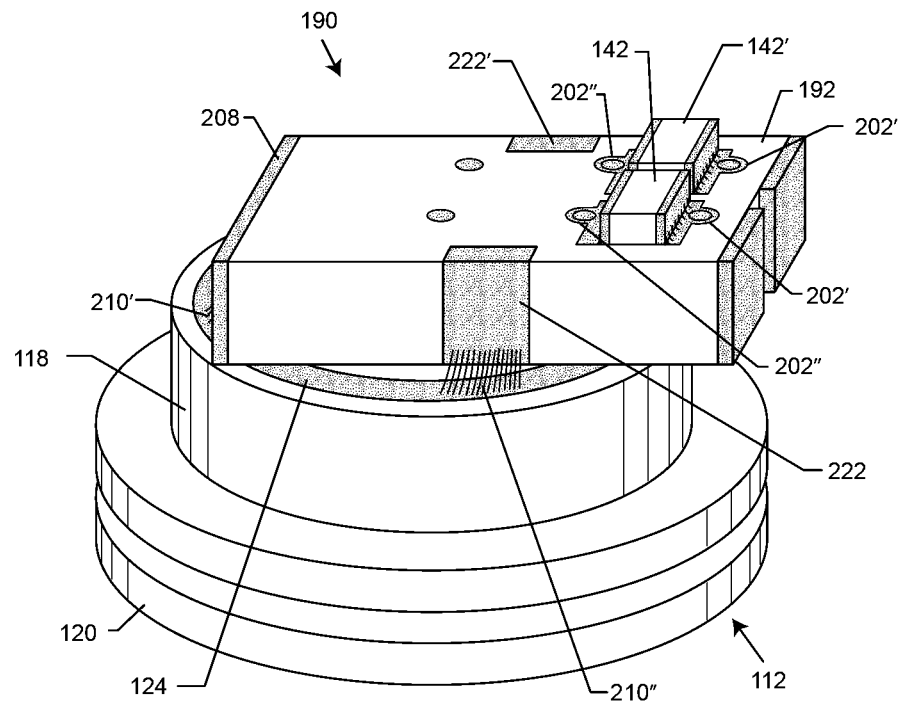
FIG. 49 is an oblique view of a bipolar hermetically sealed filter embodying the shielded three-terminal flat-through EMI/energy dissipating filter present invention.

FIG. 49 illustrates a bipolar hermetically sealed hybrid substrate filter 190 of the present invention.

Figure 50:
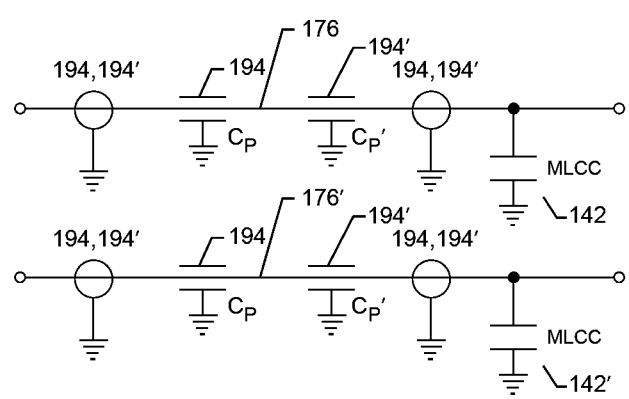
FIG. 50 is an electrical schematic for the bipolar structure of FIG. 49.

FIG. 50 is the schematic for the bipolar hermetically sealed filter illustrated in FIG. 49.

Figure 51:
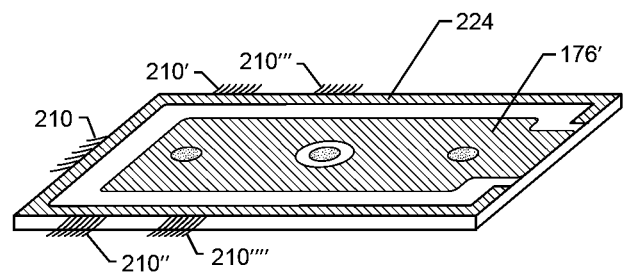
FIG. 51 is an oblique view showing modification of an active electrode plate layer shown in FIG. 47.

FIG. 51 illustrates an alternative active electrode layer to that which was previously described as 176 in FIG. 47. Referring to FIG. 51, one has to imagine removing the exploded active electrode view layer 176 in FIG. 47 and replacing it with the active electrode 176'. The active electrode plate 176' itself is not much different from that previously illustrated in FIG. 47 (its surface area is slightly smaller). What is different is that a grounded or third shield trace 224 has been deposited around the active electrode 176' on the same co-planar surface. The purpose of the surrounding grounded shield trace 224 on the same plane as active electrode 176' is to further aid in the coaxial shielding of the active electrode plate 176'. When one considers that the active electrode 176' is already sandwiched between grounded shield plates 194 and 194', this means that it is now shielded top, bottom and on both sides. The addition of the optional edge shield 224 prevents edge radiation of high frequency from the shielded three-terminal flat-through EMI/energy dissipating filter 190.

Figure 52:
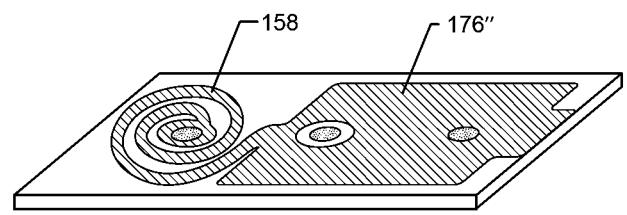
FIG. 52 is a view similar to FIG. 51, wherein the active electrode plate has been modified by adding a spiral inductor element.

The filter performance of the flat-through capacitor can be further improved by additional low-pass circuit elements. Referring to FIG. 52, one can see that the active electrode plate 176" has been modified by adding a Wheeler spiral inductor element 158. Wheeler spiral inductors are well known in the prior art for a variety of other applications. Wheeler spiral design equations are also readily available. The spiral inductor circuit trace 158 adds substantial series inductance to the active electrode plate 176" and also increases the flat-through capacitance overlap area (ECA) as well. In FIG. 52, by also having a wide active electrode plate area 176", one also maximizes the parasitic flat-through capacitance as previously described. In other words, the increased total effective overlap area (ECA) between the inductor circuit trace of 158 and the active electrode plate 176" as they are sandwiched between the two ground shield plates 194 and 194' greatly increases the flat-through capacitance $C_P$ and $C_P{'}$. In the art of EMI filter design, when one places an inductor in series with the circuit along with a capacitance to ground, this is known as an L-section low-pass filter. The schematic for the L-section filter of FIG. 52 is shown in FIG. 53.

Figure 53:
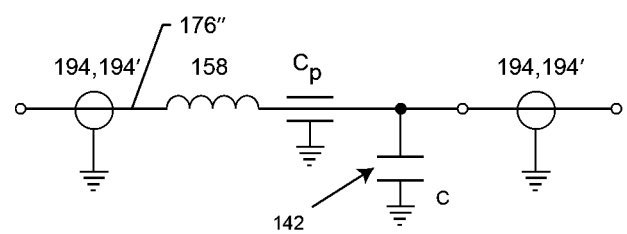
FIG. 53 is an electrical schematic for the inductor-capacitor filter formed by the substrate of FIG. 52.

Referring to FIG. 53, one can see the Wheeler inductor spiral 158 is in series with the active electrode 176" which has in parallel to ground both the flat-through parasitic capacitance $C_P$, and the MLCC capacitor 142 to form an L-filter. Not shown in FIG. 53 is the fact that the parasitic capacitance $C_P$ is really a distributive element and should be shown throughout the circuit. Accordingly, FIG. 53 should be considered a relatively low frequency model wherein a high frequency model would be of a distributed transmission line.

Figure 54:
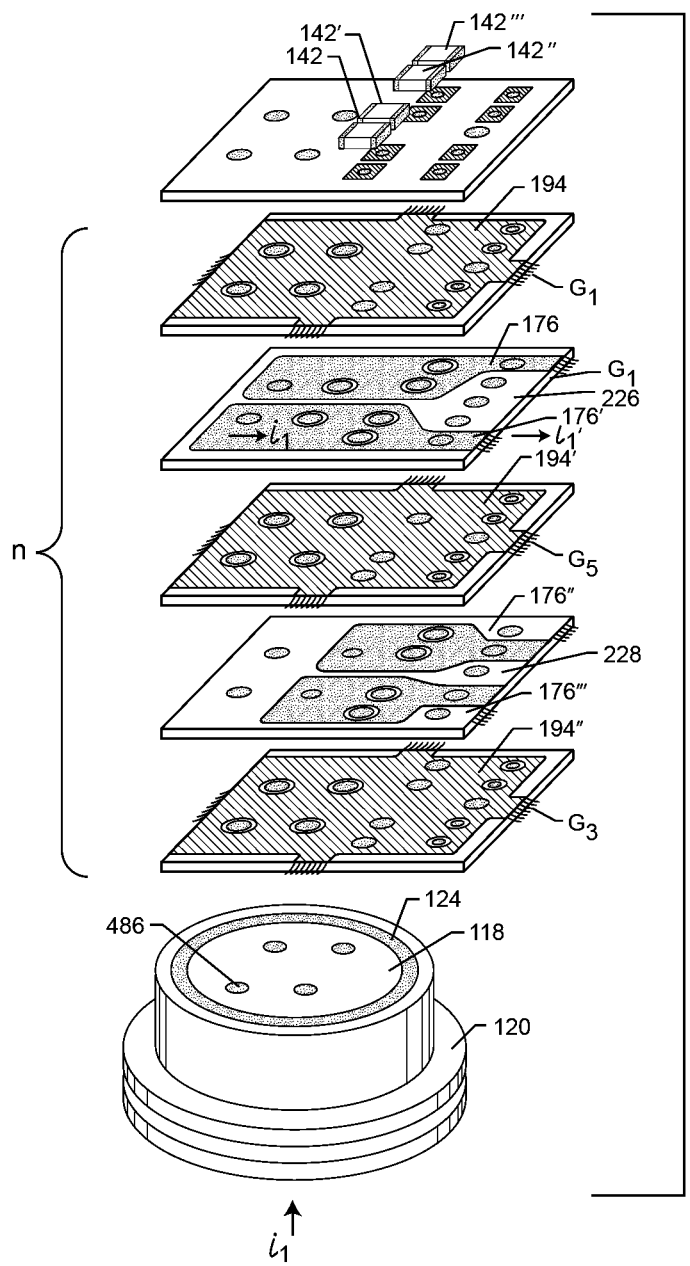
FIG. 54 is an exploded oblique view of a quadpolar filter assembly incorporating a shielded three-terminal flat-through EMI/energy dissipating filter in accordance with the present invention.

FIG. 54 illustrates a quadpolar filtered feedthrough assembly in accordance with the present invention. It is very similar in construction as previously described for the unipolar device of FIGS. 43, 45 and 47. In FIG. 54, one can see that there are multiple ground electrode shield plates 194, 194' and 194". Sandwiched between these ground electrode shield plates are active circuit electrode layers 226 and 228. Flat-through electrode circuits 176 and 176' are contained on electrode circuit trace layer 226. As previously described, parasitic capacitances or flat-through capacitances are formed due to the ECA overlap area on both sides. The spacing of the ground shields 194 and 194' are quite important in that they should not be spaced too far apart or high frequency RF leakage could occur due to the electromagnetic interference signals re-radiating from the flat-through electrode plates 176 and 176' out through the outside edge. This RF leakage was prevented in the unipolar design of FIG. 43 by wrapping the metallization surface 208 around the outside. This can also be accomplished by stitching through a number of conductive filled via holes 230 as shown in FIG. 55.

Figure 55:
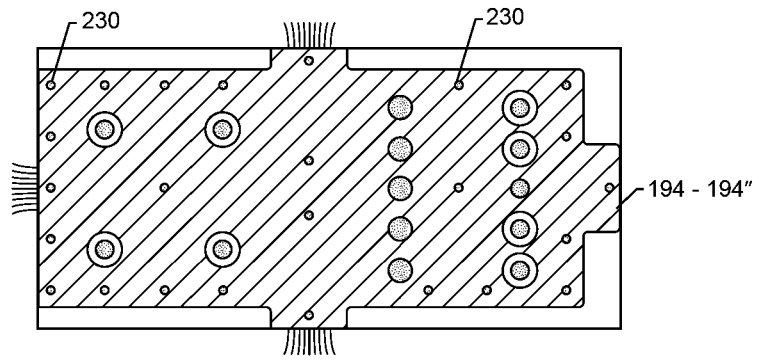
FIG. 55 is a top/plan view showing a modification of the grounded shield plates of FIG. 54.

FIG. 55 is a modification of the ground shields 194-194" of FIG. 54. One can see that there are a plurality of these stitching vias 230 or grounding vias all around the perimeter and even inside. The purpose of these stitching vias 230 is to electrically connect the three (or n) ground shield layers 194-194" together in a multi-point low inductance configuration. These stitching vias form another very important purpose in that they decrease the effective length when one looks at the side view of this laminated sandwiched structure. It is a common principle in waveguide engineering that the cutoff frequency of a waveguide is dependent upon its geometry. For rectangular waveguides, the length-to-width ratios are very important. By shortening the length, one greatly increases the frequency at which the waveguide could start to pass electromagnetic signals through it. Accordingly, by including many stitching vias 230, one is guaranteed that the sandwiched construction maintains RF shielding as to edge re-radiation integrity up into the 5 to 10 GHz region. This is well above the effective filtering frequency required for AIMDs. The upper frequency for AIMDs is defined by experts in the art as 3 GHz. The reason that attenuation above 3 GHz is not required for AIMD EMI filters has to do with the reflection and absorption of body tissues at very short wavelengths. Accordingly, it is generally accepted by the implantable medical device EMC community that electromagnetic filters need to be very effective up to 3 GHz, but not beyond. References for this is made to published ANSI/AAMI standard PC69.

Referring once again to FIG. 54, it will be understood to those skilled in the art that multiple layers n could be stacked up. The reason for this would be two fold. That is, to increase effective capacitance area (ECA) for the flat-through capacitances formed between the active electrode plates 176" and the surrounding ground shields 194" and also to increase the current handling capability of the active circuit electrode plates by putting additional redundant electrodes in parallel. This would tend to decrease the series resistance of said active circuit electrodes and, at the same time, increase their current and power handling capabilities.

Referring once again to FIG. 55, another purpose for the multiple vias 230 is to increase the mechanical integrity of a flexible hybrid substrate 192. By having multiple vias 230 stitching through, it becomes much more unlikely that said structure could delaminate. Another way to accomplish this is shown in FIG. 56, by the use of slot patterns 232.

Figure 56:
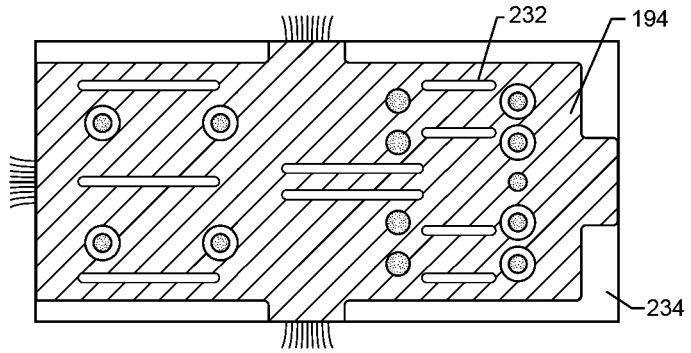
FIG. 56 is a view similar to FIG. 55 of the grounded shield plates, showing additional modifications.

In FIG. 56, there are multiple slots 232 as shown. These slots can be placed in a number of areas. The slots 232 are generally not filled in the same way that a via hole is filled. However, it does allow the adhesive binder layers to contact through the metalized electrode shield. For example, in a typical polyimide flex cable arrangement, multiple layers of polyimide are laid up with an acrylic binder. In this way, by providing for the slots 232, the acrylic binder can contact the underlying substrate material 234.

Referring back to FIG. 56, in the present invention it is preferable to align the slots 232 in the direction of active electrode circuit current flow such that torturous paths are not created for current flow. This also tends to maintain the inductive integrity of the ground plate. By way of example, if the shielded three-terminal flat-through EMI/energy dissipating filter 190 of the present invention were used at the point of lead wire ingress of a cardiac pacemaker, then the active electrodes must be low loss in order to conduct both the pacemaker pacing pulses and also conduct the biologic sensing signals. In other words, a modern cardiac pacemaker actively detects and monitors the electrical activity of the heart. One purpose for low loss active electrodes is as an AIMD battery saving purpose. Some patients are not pacemaker dependent, meaning that they only need to be paced at certain critical times when their heart rate drops too low. Therefore the pacemaker electronic circuits constantly monitor the heart. When a pacing pulse is needed, the pacemaker activates and delivers the pacing pulse through implanted leads to the appropriate cardiac tissue. The stimulation pulse then restores the heart to its natural sinus rhythm. Accordingly, it is very important that the active electrodes, such as those shown in layers 226 and 228 of FIG. 54, be relatively low loss. That is, the resistivity of the active electrodes should not be so high that pacing pulses or sensing signals are significantly attenuated.

Figure 57:
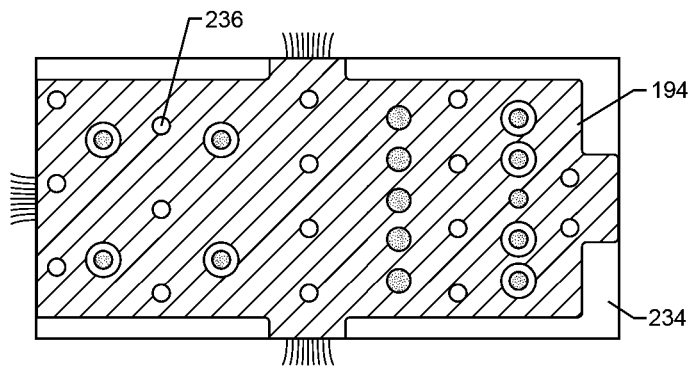
FIG. 57 is similar to FIGS. 55 and 56, showing an alternative configuration of the grounded shield plates.

FIG. 57 illustrates a methodology of putting multiple holes 236 in the metalized electrode shield. These multiple holes 236 serve the same purpose as the previously described slots 232 in FIG. 56.

Figure 58:
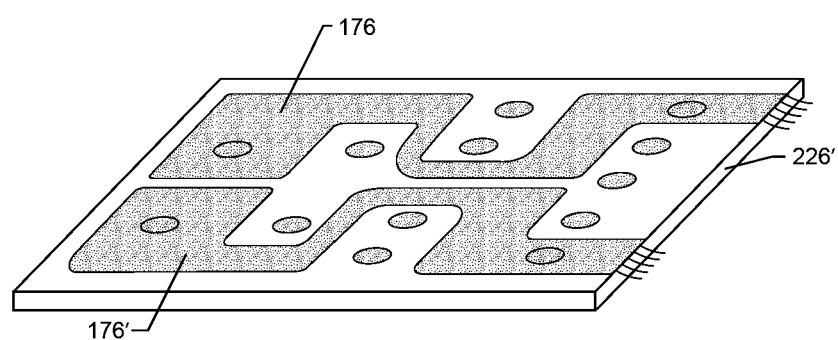
FIG. 58 is an oblique view of an alternative arrangement of the active electrode plate substrate of FIG. 54.

FIG. 58 shows an alternative arrangement for the active electrode layer 226 previously shown in FIG. 54. In FIG. 58, one could imagine that this layer 226' could replace layer 226 in FIG. 54.

Figure 59:
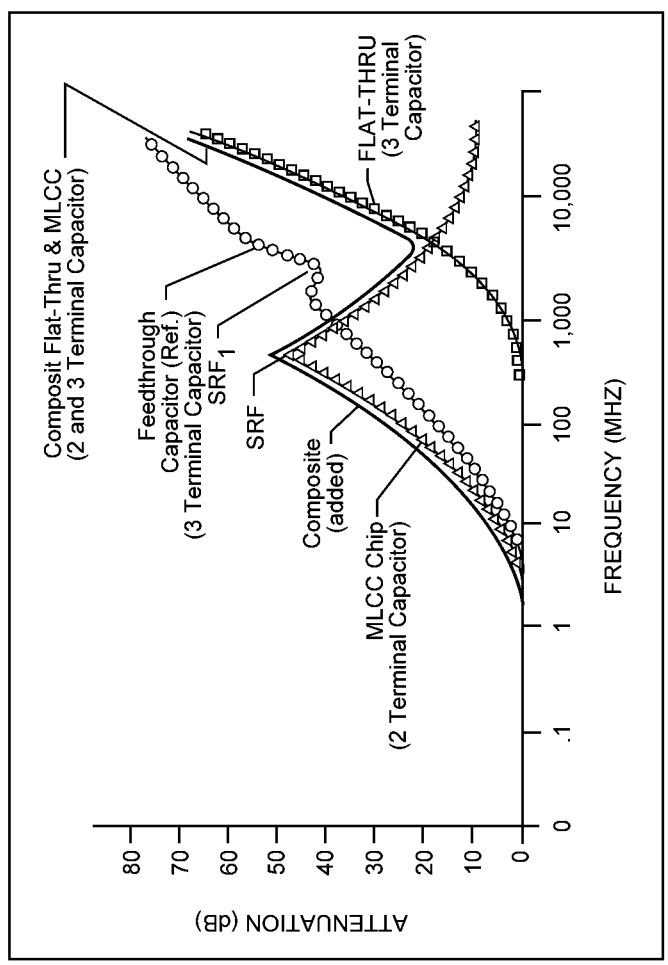
FIG. 59 is a graph illustrating attenuation versus frequency comparing the performance of the shielded three-terminal flat-through EMI/energy dissipating filter of FIG. 54 with other technologies.

FIG. 59 is a graph illustrating attenuation versus frequency comparing the performance of the shielded three-terminal flat-through EMI/energy dissipating filter 190 of FIG. 54 with a prior art feedthrough capacitor and a prior art MLCC. One can see significant differences in the comparison of a conventional feedthrough capacitor with that of an MLCC capacitor and the shielded three-terminal flat-through EMI/energy dissipating filter of the present invention. In FIG. 59, the feedthrough capacitor and the MLCC are of equal capacitance value. The capacitance value of the shielded three-terminal flat-through EMI/energy dissipating filter is significantly less. The feedthrough capacitor exhibits a small self-resonant dip shown as SRFi. Feedthrough capacitors are unique in that after they go through this type of transmission line self-resonance, they continue to function as a very effective broadband filter. The opposite is true for a prior art MLCC capacitor. The MLCC capacitor actually outperforms at its self-resonant frequency (SRF) other capacitor technologies, however, at frequencies above its self-resonant frequency, it very rapidly becomes inductive at which point the attenuation decreases versus frequency. This is highly undesirable, as high frequency emitters, such as cell phones, would not be properly attenuated. The flat-through capacitance in the present invention is a parasitic capacitance and it tends to be a relatively low capacitance value. That means that its effective 3 dB point (or point where it starts to become an effective filter) is relatively high in frequency. In this case, the 3 dB point is approximately 1000 MHz. In accordance with the design of FIG. 54, when one combines the MLCC capacitor response curve with the flat-through parasitic curves (these two capacitances are added in parallel). FIG. 48, illustrates the composite or added response attenuation curve (which for active electrode 176 is the addition of all of the capacitive elements in parallel) illustrated in FIG. 48 (parasitic inductances $L_p$ are so small in value that they can be ignored). When one compares this solid composite curve with that of a prior art feedthrough capacitor, one sees that the prior art feedthrough capacitor outperforms the composite curve at frequencies above 1000 MHz. It will be understood to those skilled in the art that one way around this would be to increase the capacitance value of the flat-through parasitic capacitor so that it could start performing at a lower frequency. An effective way to increase the capacitance value of the parasitic capacitor is to increase the dielectric constant of the surrounding dielectric materials. Referring back to dielectric substrate layers 226 and 228 of FIG. 54 that would mean, for example, using a high dielectric constant (k) dielectric, such as barium titanate or strontium titanate for the insulative substrate material 234. This would raise the dielectric constant (k) up into the area above 2000. Accordingly, the value of the flat-through capacitance would go up so high that one would not even need to include the MLCC capacitance. Another way to accomplish the same thing and to use lower cost materials would be to use flex cable technology, such as polyimide or Kapton flex as previously described. The problem with this is that the dielectric constant of these materials is relatively low (typically below 10). However, one way to make up for this would be to increase the effective capacitance area in the overlap area of the active electrode plates 176 and their surrounding sandwiched ground shields 194 and 194' (and/or reduce the dielectric thickness, d).

Figure 60:
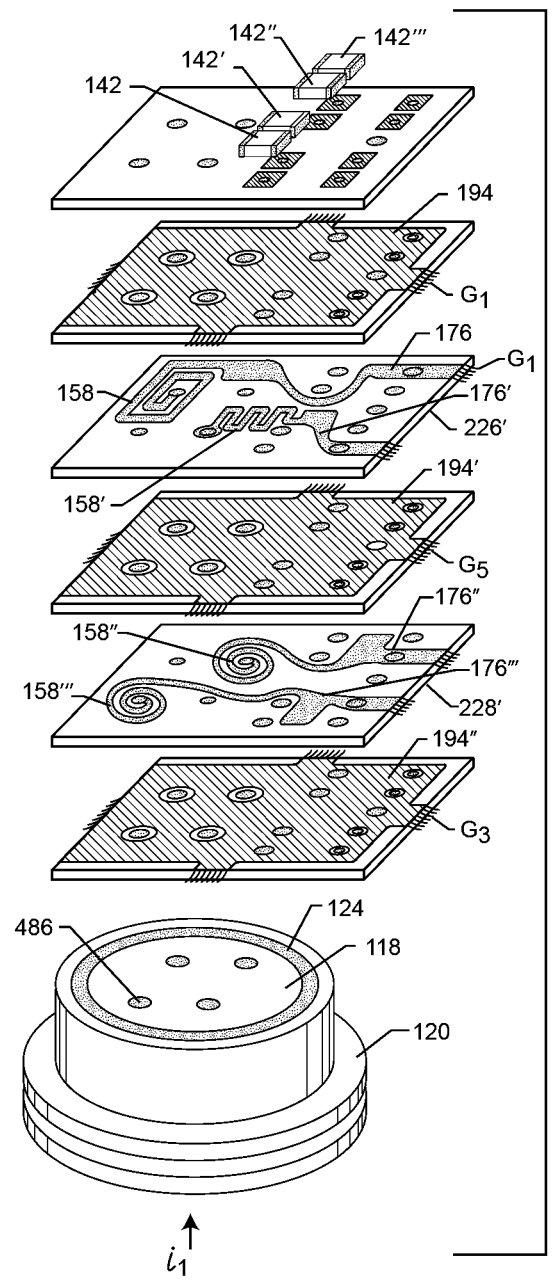
FIG. 60 is an exploded oblique view that is similar to FIG. 54 wherein the active electrodes have been modified to include inductors.

FIG. 60 is an exploded view of the quadpolar hybrid EMI filter of the present invention that is similar to that previously shown in FIG. 54. In FIG. 60, the circuit layers 226' and 228' of FIG. 54 have been modified to add inductor traces 158-158'''. These inductor traces are included as part of and are in series with active electrodes 176-176'''. It will be understood to those skilled in the art that one would most likely select one inductor pattern and stay with that. For example, in electrode plate 176, there is a rectangular Wheeler spiral inductor 158. In electrode plate 176', we have by way of example, an inductor meander 158' which can be one of many patterns, including those illustrated in FIG. 65. In electrode plates 176'' and 176''', we have round Wheeler spiral inductors 158'' and 158''' as shown. Embedding co-planar inductors in series with the active electrodes is virtually a no-cost addition. The reason for this has to do with the manufacturing methods typically employed to produce flex cables or even solid substrates. That is, a solid metal layer is laid over the entire surface by plating or other metal-deposition processes and then resistive materials are laid down by silk-screening or similar processes. Then chemical etchings are used to remove all of the metal except for the desired electrode patterns. Accordingly, once a setup is made, adding inductor elements 158-158''' as shown in FIG. 60 becomes very inexpensive and easy to do. Advantages of adding the inductors as shown in FIG. 60 include making the low-pass EMI filter from a single element into what is known as a dual element L-section low-pass filter. A dual element filter has a steeper attenuation slope and is therefore more efficient. There is another advantage from adding the inductor shapes as shown in FIG. 60. By doing this, one increases the ECA and therefore the parasitic flat-through capacitance at the same time. Therefore one ends up with a very efficient distributive filter consisting of the inductance in series with the active electrode(s) and parasitic capacitances in parallel to ground.

Figure 61:
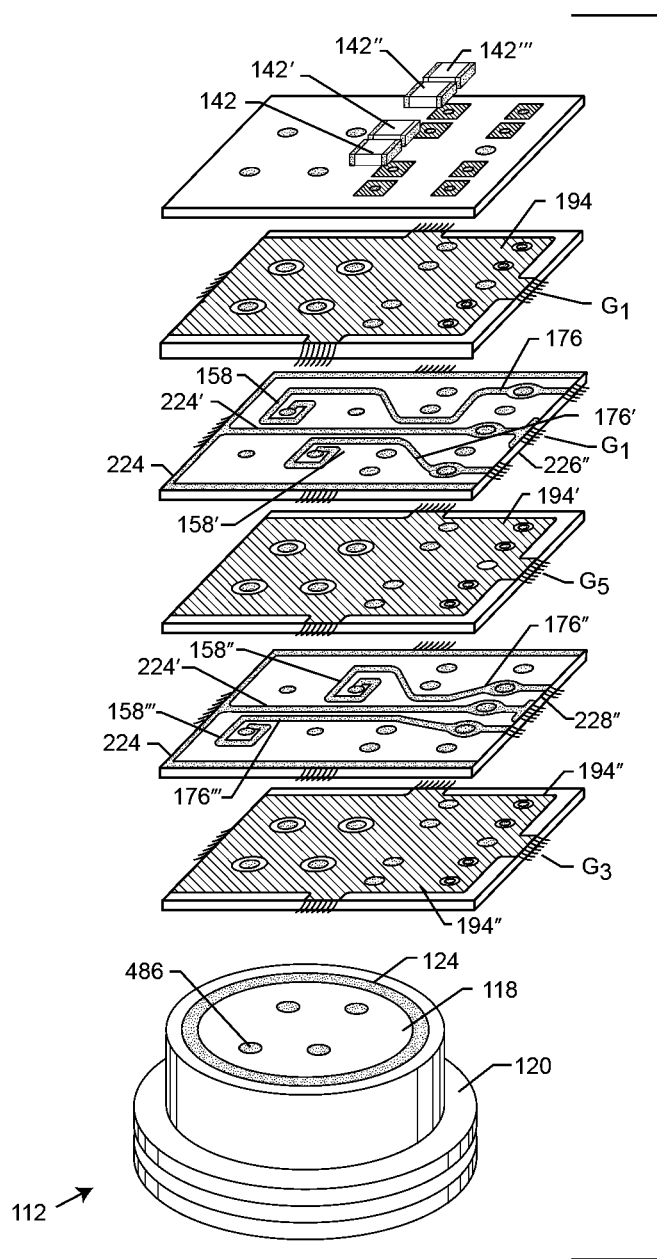
FIG. 61 is an exploded oblique view very similar to FIGS. 54 and 60 except that edge shields and optional separating shields have been placed to prevent EMI radiation from the active electrode plates or optionally between co-planar electrode plates.

FIG. 61 is very similar to FIG. 60 except that the active electrode trace layers 226'' and 228'' have been modified by adding an optional surrounding co-planar ground shield 224. This surrounding ground shield concept to prevent substrate edge re-radiation was previously described in relation to FIG. 51. However, the difference in FIG. 61 is that an optional co-planar ground shield 224' has also been disposed on layers 226'' and 228'' between each of the active electrode traces 176 and 176' and also 176'' and 176'''. For example, with reference to layer 226'' of FIG. 70, one can see a co-planar ground shield 224' that is disposed between circuit traces 176 and 176'. This would be used in the case where it was important to prevent cross-talk between adjacent circuit traces 176 and 176'. For example, this might be important in a cochlear implant to keep each digital or analog voice channel that stimulates the auditory nerve free of distorting noise from an adjacent channel. This becomes particularly important when the dielectric layer 226'' on which the circuit electrodes 176 and 176' are deposited, are of high k dielectric materials. The use of high k dielectric materials increases the parasitic capacitance that would occur between circuit electrode layers 176 and 176'. The presence of a co-planar grounded shield trace 224' prevents the cross-talk between the adjacent circuit traces. This cross-talk shield 224' can be used in conjunction with, as shown in FIG. 61, or without (not shown) with the surrounding edge shield 224. The cross-talk shield 224' also need not be used on all active electrode layers in a particular shielded three-terminal flat-through EMI/energy dissipating filter 190, but only in those layers where cross-talk is a concern between adjacent circuits. In other words, the cross-talk shield 224' may be used on layer 226'' but not be needed on layer 228''. It will be understood to those skilled in the art that on a particular substrate layer, that the number of circuit active electrodes (and optional cross-talk shields) is not limited to two (such as 176 and 176' as shown in FIG. 61), but can be of any number, n.

Figure 62:
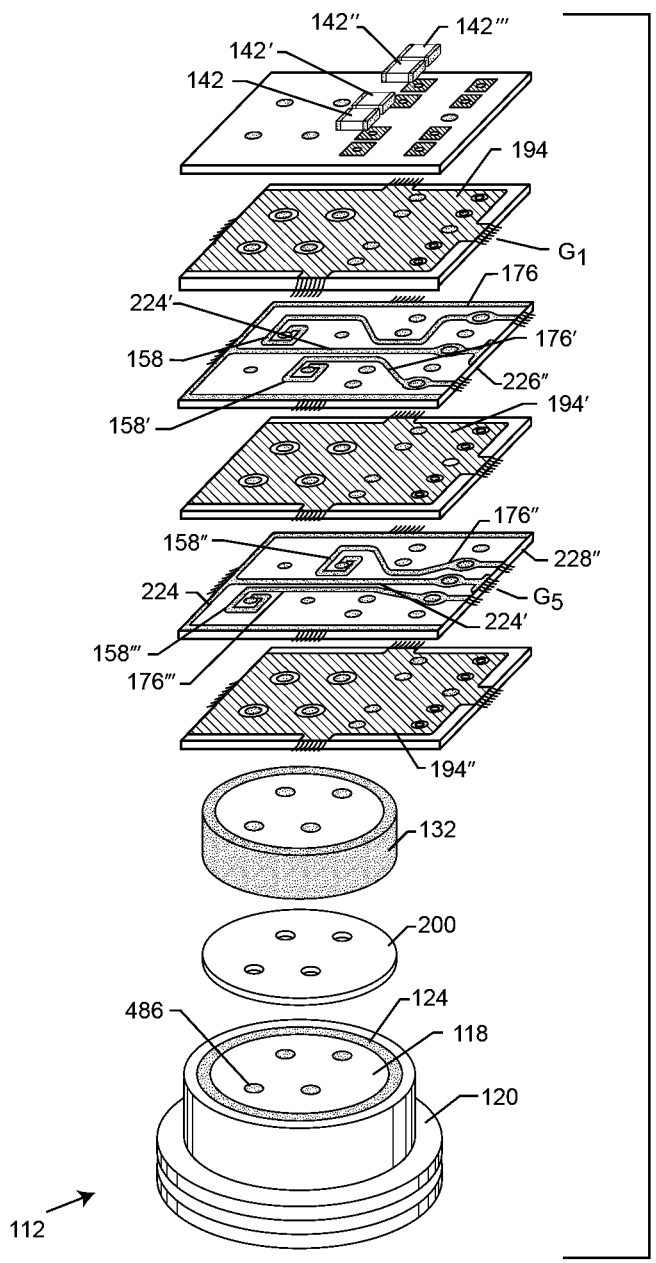
FIG. 62 is an exploded oblique view of an alternative form of the shielded three-terminal flat-through EMI/energy dissipating filter similar to FIG. 54.

FIG. 62 is yet another alternative to the quadpolar shielded three-terminal flat-through EMI/energy dissipating filter 190 as previously described in relation to FIG. 61. The difference between FIG. 61 and FIG. 62 is the addition of a feedthrough capacitor 132 which is bonded to the hermetic terminal 112 by way of an insulative adhesive washer 200. Feedthrough capacitors 132 are well known in the prior art and provide very effective high frequency filtering. FIG. 62 illustrates that these prior art feedthrough capacitors can be used in combination with the novel shielded three-terminal flat-through EMI/energy dissipating filter technology of the present invention. In a preferred embodiment, the structure as illustrated in FIG. 62 would allow for the elimination of the MLCC capacitors 142-142''' as illustrated (or they could be replaced by higher value MLCCs, film chip capacitors, tantalum technology or the like). In other words, there would be sufficient capacitance from the feedthrough capacitor 132 in combination with the flat-through capacitances of the hybrid substrate electrodes such that it is unlikely that additional filtering would be required for high frequency (above 100 MHz) attenuation. However, if one were to desire extremely low frequency filtering, one could use a monolithic ceramic feedthrough capacitor as illustrated in FIG. 62 along with the shielded three-terminal flat-through EMI/energy dissipating filter technology and surface mounted very high capacitance value tantalum capacitors. This would yield a filter that would be effective from all the way down in the kHz frequency range all the way up through 10 GHz. For AIMD applications, this would be very important for filtering for low frequency emitters such as those created from electronic article surveillance (EAS) gates or low frequency RFID readers (in the 125 to 132 kHz or 13.56 MHz range). These EAS gates are the pedestals that a person, including a pacemaker patient, typically encounters when exiting a retail store. These detect tags on articles and goods such as to prevent theft. One common system is manufactured by Sensormatic which operates at 58 kHz. It has been demonstrated through numerous publications that these EAS gates can interfere with pacemakers and ICDs. The present invention as illustrated in FIG. 62 would be effective in attenuating signals at 58 kHz all the way up through cell phone frequencies in the GHz range.

Figure 63:
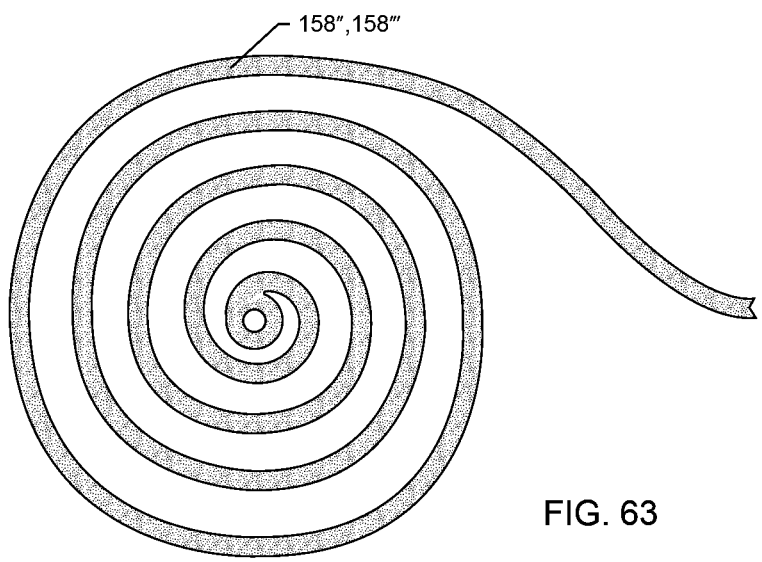
FIG. 63 is an enlarged view of a round Wheeler spiral shown forming a portion of an active electrode plate in FIG. 60.

FIG. 63 is a blown up view of the round Wheeler spirals 158'' and 158''' of FIG. 60.

Figure 64:
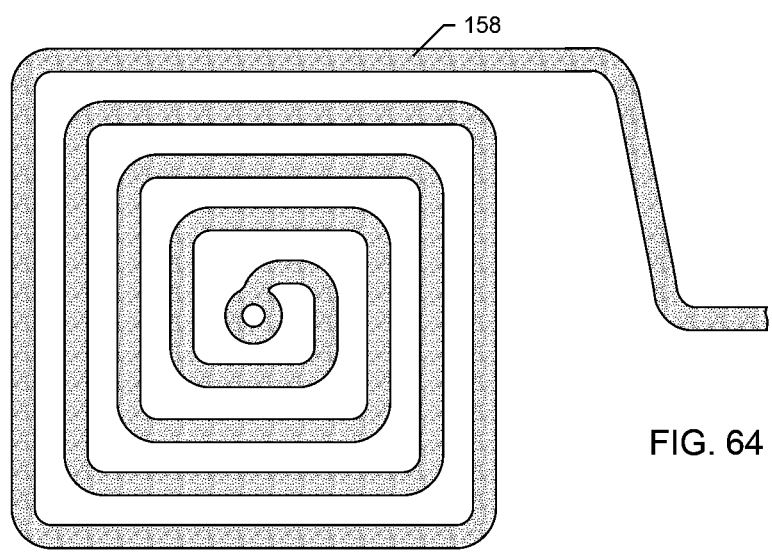
FIG. 64 is similar to FIG. 63, showing a square Wheeler spiral such as those shown forming portions of the active electrode plates in FIGS. 60, 61 and 62.

FIG. 64 is a square Wheeler spiral which is very similar to the rectangular Wheeler spiral 158 previously shown in FIG. 60.

Figure 65:
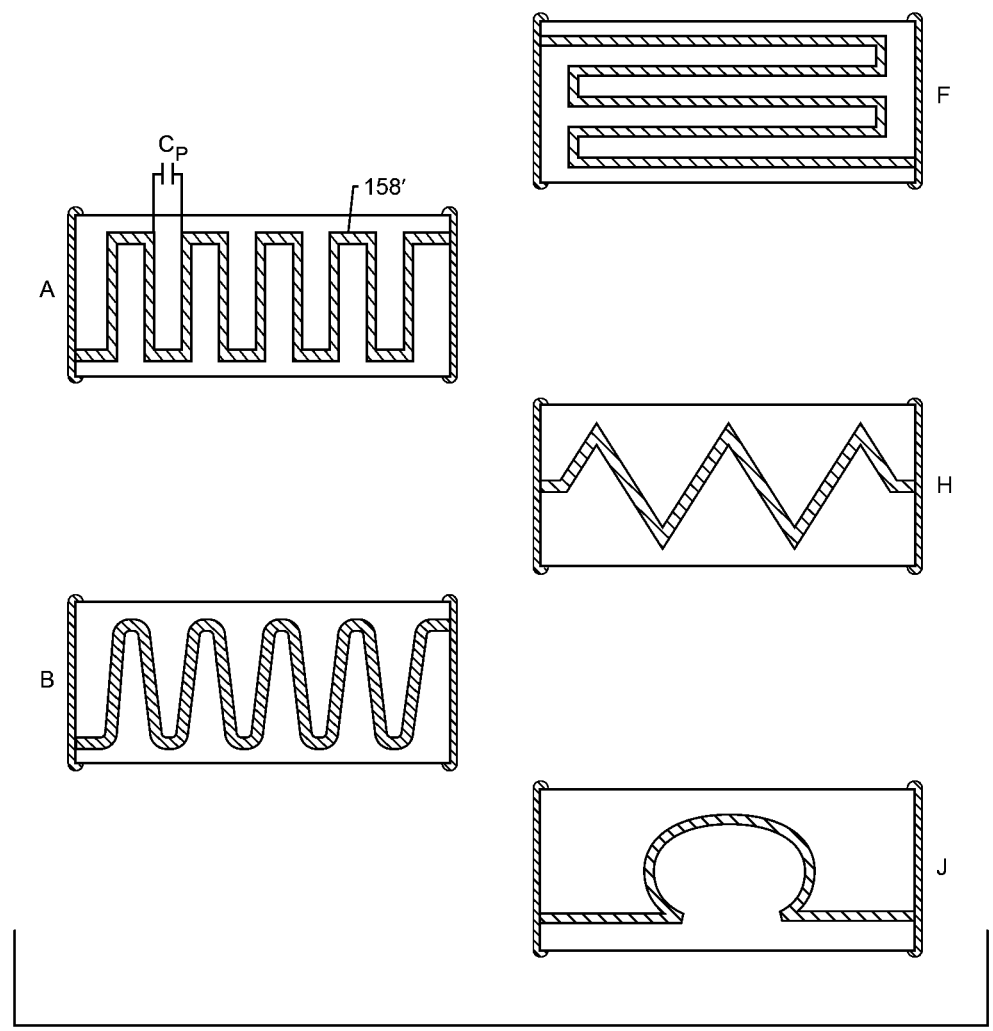
FIG. 65 illustrates several typical inductor meander shapes.

FIG. 65 shows some typical inductor meander shapes 158'. It will be understood to those skilled in the art that any number of different inductor shapes can be easily deposited on the same co-planar substrate layer in series and an integral part of the active electrode plate(s) 176 of the shielded three-terminal flat-through EMI/energy dissipating filter 190 technology of the present invention.

Figure 66:
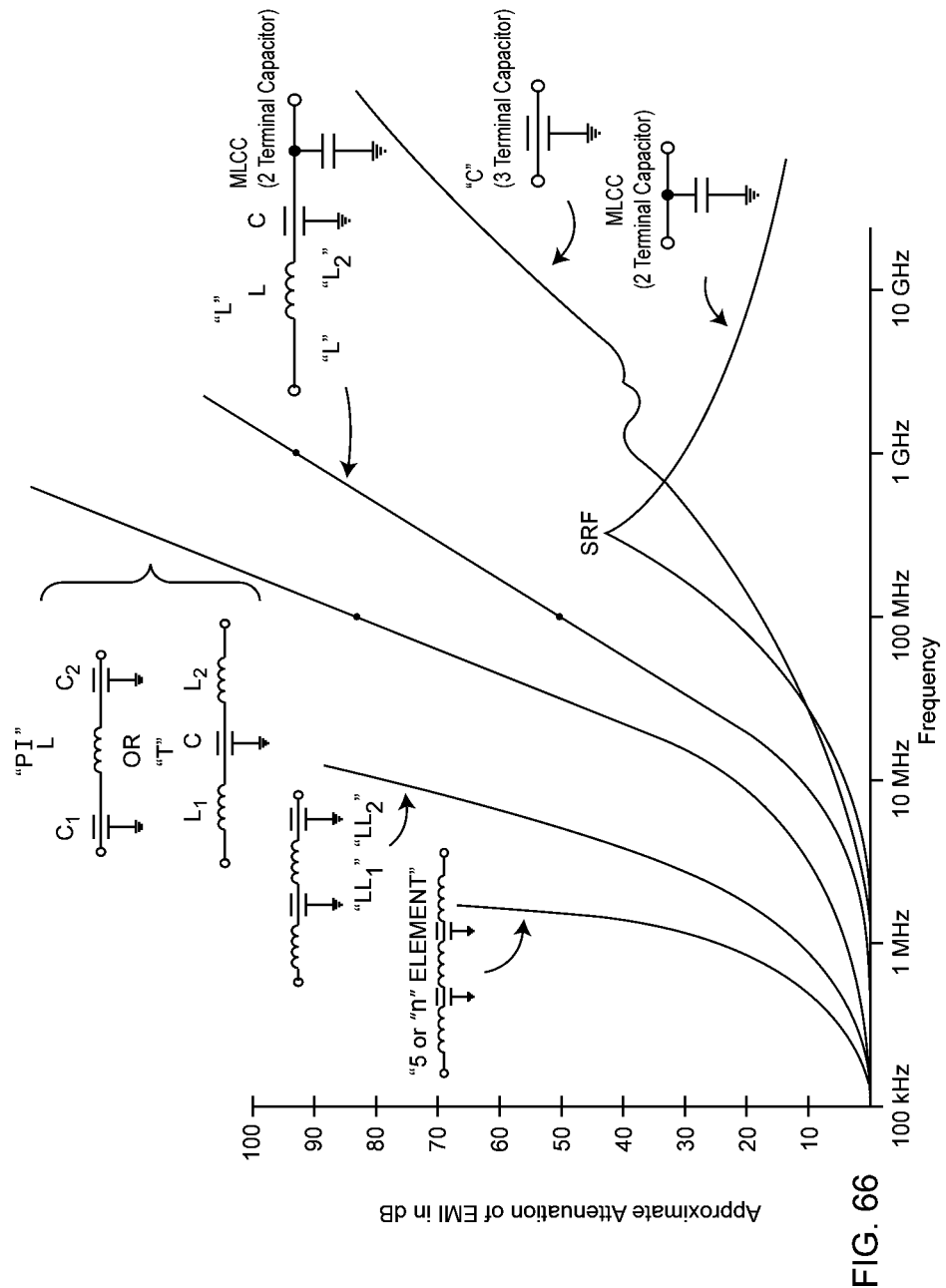
FIG. 66 illustrates the attenuation curves for various types of low-pass filters.

The advantage of adding additional elements to a low-pass filter is dramatically illustrated by FIG. 66, which illustrates the attenuation curves for various types of low-pass filters. By way of reference, a typical MLCC capacitor curve is shown. As one can see, the MLCC undesirably goes through a self-resonant frequency SRF after which its attenuation declines versus frequency (the MLCC undesirably becomes increasingly inductive). However, for shielded three-terminal flat-through EMI/energy dissipating filters of the present invention, one achieves broadband filter performance all the way up to and including 10 GHz. As one can see, a single element or C section filter has an attenuation slope of 20 dB per decade. When one adds a series inductor to this, as shown in the L section filter, the attenuation slope increases to 40 dB per decade. The addition of a third element, which makes the filter into either a π or T section, increases the attenuation slope to 60 dB per decade. Going further, one could have a double L, which is shown as a $LL_1$ or an $LL_2$, meaning that the inductor can point either towards the body fluid side or to the device side, has an attenuation slope of 80 dB per decade. One can add any number of elements in this way. For example, a 5-element filter will have 100 dB per decade attenuation slope. It will be understood to those skilled in the art that any number of elements could be used.

Referring once again to FIG. 60, the structure shown has an electrical schematic as shown in on FIG. 53 as an L section circuit. The capacitance of this L section consists of the sum of the parasitic flat-through capacitance $C_P$ which is formed between the active electrode plate 176 including the ECA formed from the inductors 158, and the opposing grounded shields 194 and 194'. The MLCC capacitor 142 in FIG. 53 represents the capacitors 142-142''' surface mounted onto the hybrid substrate 192. The MLCC capacitor is effective up to its resonant frequency. However, that is where the flat-through capacitance takes over yielding the relatively smooth curve shown in FIG. 66 for the L section filter. It is understood to those skilled in the art that the L section could be reversed. In other words, the inductor spiral could be designed and put on the other side of the capacitor as opposed to towards the body fluid side as presently shown in FIGS. 52 and 53. In addition, it will be understood to those skilled in the art that multiple inductors could be placed inside of the novel hybrid substrate 192 in order to form a "π", "T", "LL" or even a "5" or "n" element device. Accordingly, the present invention includes a new method of constructing prior art low-pass EMI filter circuits that are already well known in the art. In other words, the feedthrough capacitor, the L, the π, the T and LL filters are already well known. However, this is the first time, to the knowledge of the inventors, that a flat-through capacitance has been embedded within grounded shields 194 and 194'.

Figure 67:
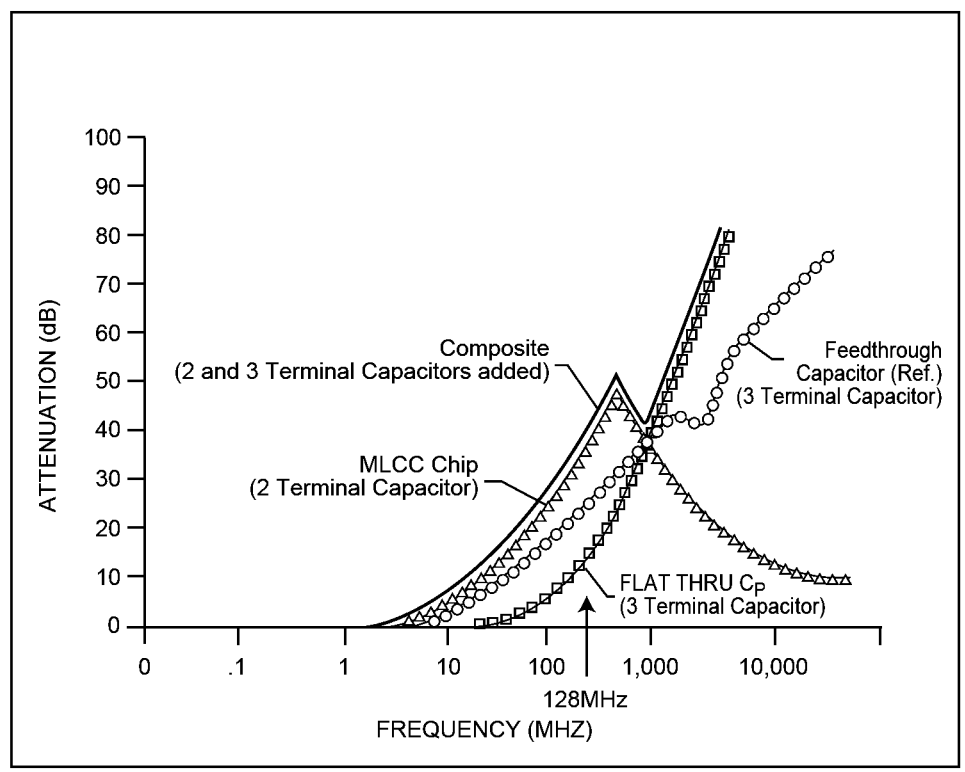
FIG. 67 is a family of filter attenuation curves similar to that shown in FIG. 59.

FIG. 67 is a family of filter attenuation curves similar to that previously shown in FIG. 59. In FIG. 66, one can see that the 3 dB cutoff point, or the point at which the flat-through ($C_P$) curve of the shielded three-terminal flat-through EMI/energy dissipating filter starts to become effective, has been moved substantially downward in frequency (to the left). In this case, its 3 dB point is approximately 40 MHz. In addition, since it is now part of an L section filter, its attenuation slope rate has been increased from 20 to 40 dB per decade. In FIG. 67, the referenced feedthrough capacitor curve is unchanged as well as the MLCC curve (these are discrete component comparison curves only). However, the composite curve, which is the addition of the MLCC curve, which is surface mounted to the shielded three-terminal flat-through EMI/energy dissipating filter substrate to the shielded three-terminal flat-through EMI/energy dissipating filter active electrode flat-through curve, is now substantially improved. At all points, the composite curve of the shielded three-terminal flat-through EMI/energy dissipating filter with the surface mounted MLCC(s) outperforms (has higher attenuation than) the referenced prior art feedthrough capacitor. In many cases, the amount of improvement is very substantial. For example, at MRI frequencies which are 64 MHz for 1.5 Tesla machines and 128 MHz for 3 Tesla machines, there is an improvement anywhere from 10 to over 20 dB. This is very significant and very important to protect an active implantable medical device from interference during MRI scans.

Figure 68:
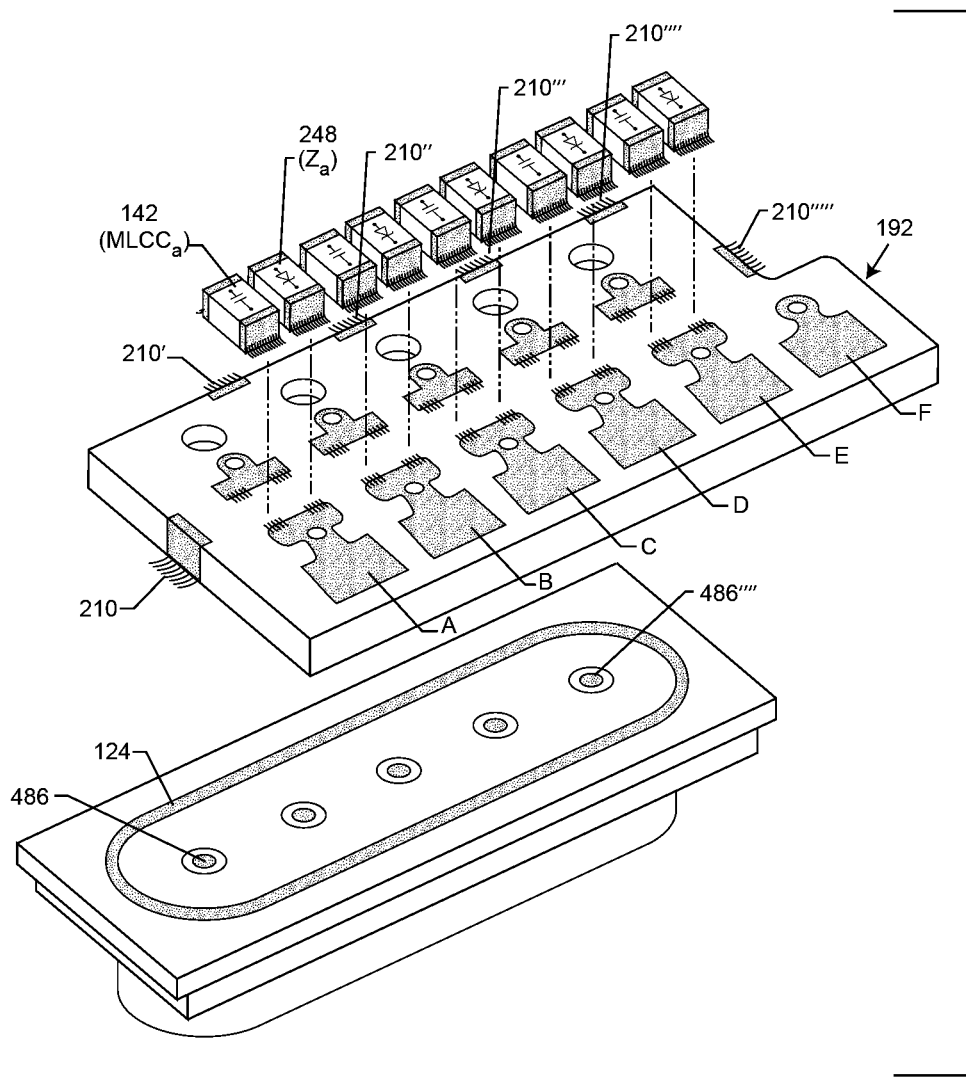
FIG. 68 is an exploded isometric view of an inline hybrid substrate embodying the shielded three-terminal flat-through EMI/energy dissipating filter of the present invention.

FIG. 68 illustrates an inline hybrid substrate 192 of the present invention. In this case, there are internal grounded shield plates (not shown) that have already been well described. There are multiple electrical connection points to the gold braze 124 consisting of 210-210''''. In this case, back-to-back MLCC capacitors 142 and voltage suppression diodes 248 (also known as zener diodes) have been incorporated in parallel. This is best understood by referring to the electrical schematic diagram of the structure shown in FIG. 69. Starting from the outside of an electronics module of the body fluid side of an AIMD (on the left), one can see that as EMI enters, it first encounters a flat-through capacitance $C_P$ in accordance with the novel through electrodes of the shielded three-terminal flat-through EMI/energy dissipating filter of the present invention. Then, moving to the right in FIG. 69, the EMI encounters an inductance $L_1$ which is typically from an embedded co-planar Wheeler spiral inductor (not shown) contained within the active electrode plates of the hybrid substrate 192. Then the EMI encounters the parallel combination of the MLCC capacitor 142 and the high voltage suppression diode 248. Then there can be another inductor (optional) $L_2$ that would be embedded within the hybrid substrate 192 and an additional flat-through capacitance $C_P'$ before one reaches the electrical connection pads A through F as illustrated.

Figure 69:
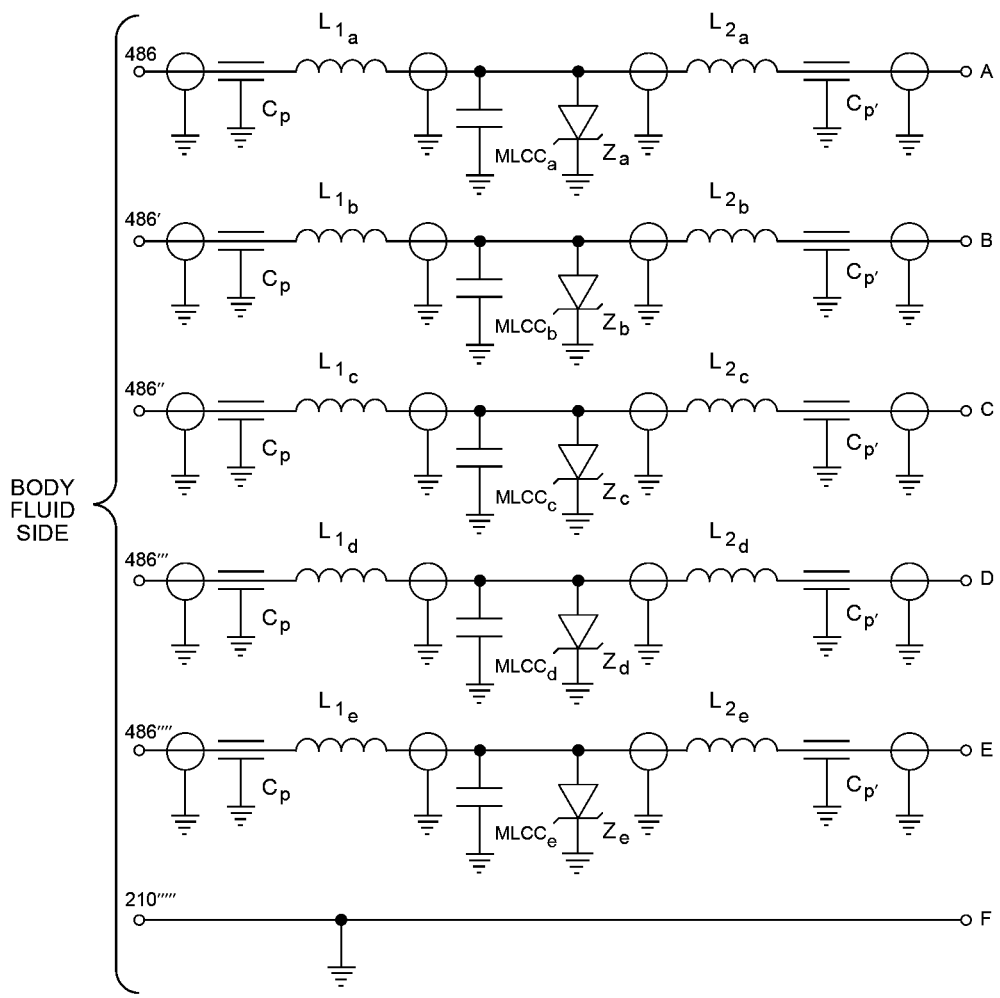
FIG. 69 is an electrical schematic diagram of the structure shown in FIG. 68.

Referring once again to FIGS. 68 and 69, the inductors, for example inductor $L_{1a}$ and $L_{2a}$, could be constructed of square, rectangular or a round Wheeler spirals or any of the other meander shapes previously described. FIG. 69 illustrates a very efficient five element low-pass filter.

Figure 70:
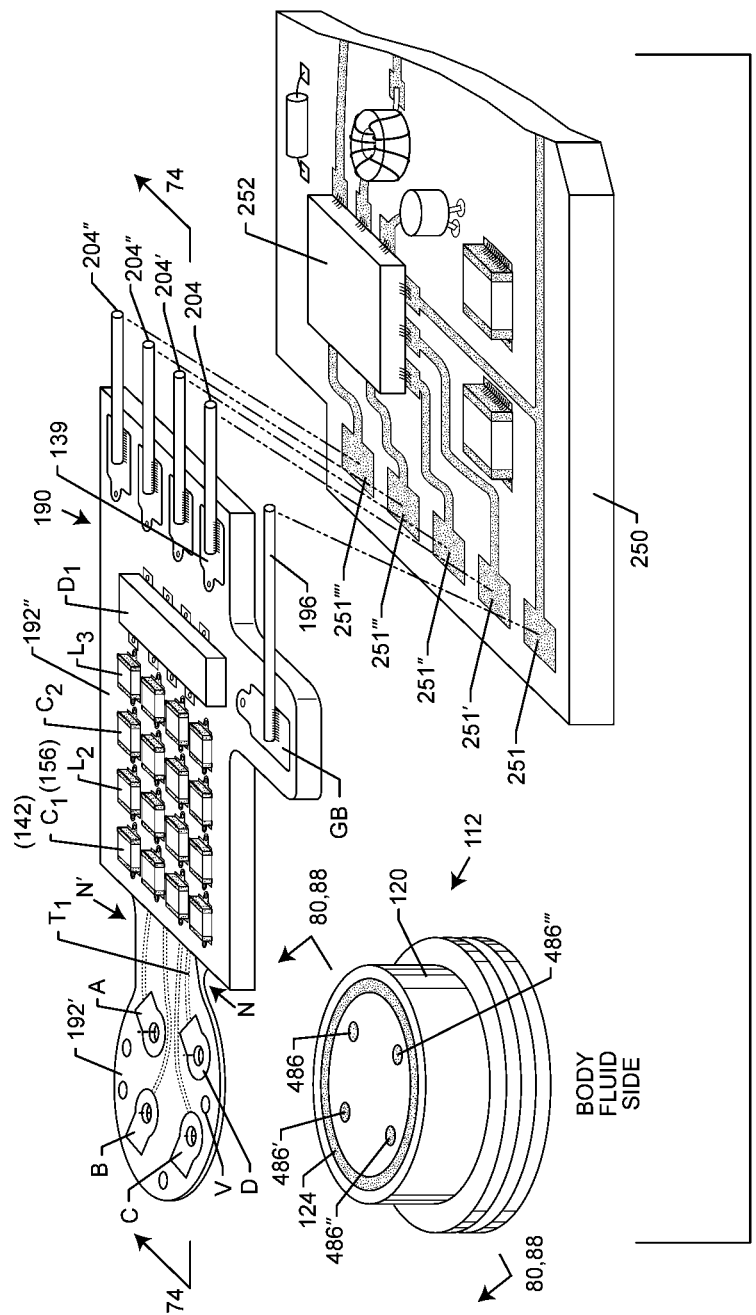
FIG. 70 is an exploded oblique view of another form of a shielded three-terminal flat-through EMI/energy dissipating filter embodying the present invention.

FIG. 70 illustrates another form of the novel hybrid substrate 192 of the present invention. The shielded three-terminal flat-through EMI/energy dissipating filter includes a hybrid substrate 192 is divided into two sections: 192' and 192". Section 192' is a relatively thin area of flex cable and is therefore very flexible. Section 192" can be made of similar or same materials as section 192' (or it can be a rigid board or substrate to which flexible section 192' is connected), but its thickness is built up until it forms what is known in the art as a section of "rigid" cable. This rigid section 192" could be of polyimide, Kapton or other typical flex cable construction. It will also be understood to those skilled in the art that this could also be a piece of rigid multilayer substrate or circuit board, including any of the ceramics or FR4 board or the like. The flex cable section 192' at terminal A-D are designed to slip down and connect to 486-486''' of the platinum filled vias of a hermetic seal 112 of an AIMD or any other electronic device (hermetic or not), such as those typically used in telecommunications, consumer electronics, military or even space applications). The hermetic seal 112 can be any type of terminal, including non-hermetic terminals or even plastic terminals. The present invention is applicable to any electronic assembly or a point at which any lead wires ingress and egress an electronic assembly, subassembly or housing. The methods of attachment to the platinum filled vias 486-486''' of the hermetic seal 112 and to the gold braze 124 will be described in connection with subsequent drawings.

Referring now to the rigid section 192'', one sees that a number of passive or active surface mounted electronic components can be mounted (they can also be embedded which is also well known in the prior art of multilayer substrate design). In this particular case, the hybrid substrate 192 of FIGS. 73-74 has been designed with convenient lead wires 204-204''' and 196 for easy connection to lands of a circuit board 250 perhaps with an integrated circuit or microchip 252 within the active implantable medical device. The circuit board 250 is not part of the present invention, but is important in that the present invention be capable of connecting and interfacing with it.

Figure 71:
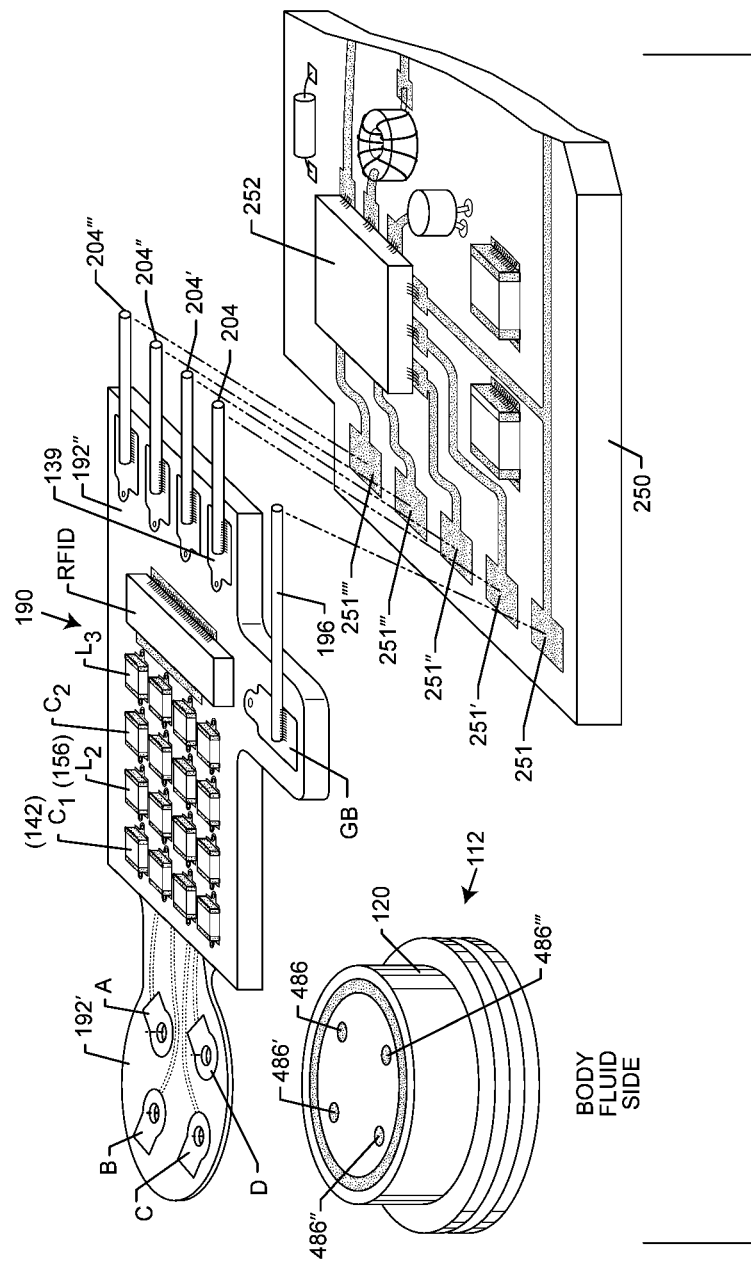
FIG. 71 is similar to FIG. 70 except that the diode array has been replaced with an RFID chip.

FIG. 71 is very similar to FIG. 70 except the diode array $D_1$ has been replaced with either a passive or an active RFID chip (RFID). In the preferred embodiment, this would be a low frequency passive RFID chip meaning that it would operate at a frequency that could easily penetrate the titanium electromagnetic shield of a typical AIMD or other EMI shielded electronic device. In a preferred embodiment, the RFID chip would operate in the International Standards Organization (ISO) band of 125 to 135 kHz. The RFID chip could be used for a number of different purposes, including identification of the model number, serial number of the AIMD, important patient or implanting physician information and the like. See U.S. Patent Application Publication No. US 2006-0212096 A1, the contents of which are incorporated herein by reference.

The RFID chip as illustrated in FIG. 71 could be simply mounted but not electrically connected to the active electrodes of the shielded three-terminal flat-through EMI/energy dissipating filter. No electrical connections are required for a passive RFID chip. In other words, when an external interrogator/reader was used, a powerful electromagnetic field would activate an antenna within RFID chip and it would automatically use the received power to turn on its microchip and transmit a return pulse. However, in another embodiment, the RFID chip, as shown in FIG. 71 could be electrically connected to power circuits embedded within the shielded three-terminal flat-through EMI/energy dissipating filter such that it received power from the internal battery of the AIMD. In this case, it would be known as an active RFID chip. With an active (powered) RFID chip, it could embody a much more sensitive receiving circuit and also transmit a much more powerful return pulse. In another embodiment, the RFID chip as shown in FIG. 71 could be used as a wake-up feature for AIMD RF telemetry circuits.

In the past, pacemaker and ICD and neurostimulator telemetry was done by close-coupled magnetic coils. In this older art, it was typical that the AIMD would have a multiple turn wire antenna within the titanium housing of the AIMD. There were even AIMDs that use an external loop antenna of this type. To interrogate or reprogram the AIMD, the physician or other medical practitioners would bring a wand, with a similar antenna embedded in it, very close to the AIMD. For example, for a typical pacemaker application, the telemetry wand would be placed directly over the implant with a wire connected to an external programmer. The medical practitioner would move the wand around until the "sweet-spot" was located. At this time, the external programmer would become active and electrograms and other important information would be displayed. Typically, the wand would be right against the patient's skin surface or at most a couple of centimeters away. In the last few years, distance RF telemetry is becoming increasingly common. In this case, for example for a cardiac pacemaker, there would be a high frequency antenna that would be embedded within the plastic header block of the AIMD (outside the EMI shielded titanium housing). This would communicate with an external RF receiver-transmitter programmer. A typical band for such communication would be in the 402 to 405 MHz (known as the MICS band). Other devices use even higher frequencies for distance RF telemetry. A problem with such distance telemetry circuits is the energy consumption of the receiver circuitry which must be on all the time. There is one methodology which is known in the art as the Zarlink chip. The Zarlink chip uses a higher frequency (in the GHz range) to wake-up the lower frequency RF telemetry circuit. The higher frequency is more efficient. However, the device or chip still consumes an amount of idling energy from the AIMD battery to always be alert for its wake-up call. An alternative of this resides in the present invention where a passive RFID chip is used as a wake-up feature. This RFID can be integrated into the hybrid substrate 192 of the present invention (or mounted anywhere else inside or outside the housing of the AIMD). In a preferred embodiment, the external RF programmer can incorporate a low frequency RFID reader which would transmit a signal which would penetrate right through the titanium housing of the AIMD and activate the embedded passive RFID chip. The circuitry of the RFID chip would be connected to the telemetry circuits contained within the AIMD. For an example, in the case of a pacemaker, the external programmer would send the RFID signal as a wake-up call to turn on the telemetry receiving circuits so that the pacemaker could communicate with the external programmer.

Figure 72:
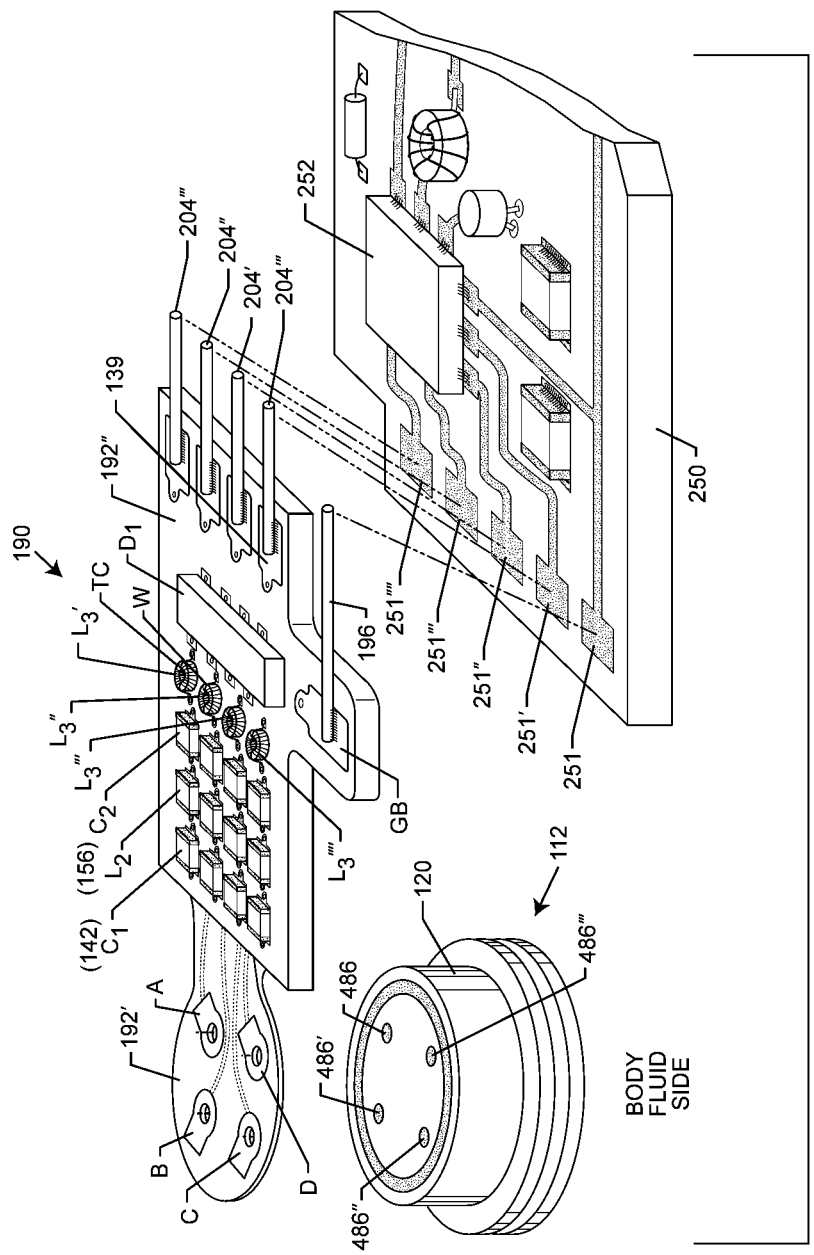
FIG. 72 is similar to FIG. 70, wherein toroidal inductors have been used to replace a series of surface mount chip inductors.

FIG. 72 is very similar to FIG. 70. In this case, toroidal inductors L3-L3''' have been used to replace the surface mount chip inductors. Chip inductors are low in both their inductance value and their current rating. Chip inductors can be acquired in two main forms: a) with a ferrite core and; b) without a ferrite core. For exposure in MRI applications, it is usually desirable to eliminate ferrite material as it will saturate due to the main static field of the MR scanner. See U.S. Patent Application Publication No. US 2007-0112398 A1 and U.S. Pat. No. 7,363,090, the contents of which are incorporated herein with these references. In FIG. 72, one can see that the toroidal inductor $L_3'$ does have a ferrite core TC with many turns of wire W wrapped around it. This makes for a very large inductor value. However, as mentioned, in an MRI environment, the inductance would drop to a very low value due to the saturation of the ferrite element TC itself. It is a feature of the present invention that the ferrite element would be selected so that it would not exhibit permanent remnants. That is, once the device was removed from the magnetic resonance (MR) scanner, the magnetic dipoles would return to their scattered state and the inductor would continue to operate as previously intended. The purpose of the toroidal inductors L3-L3''' would be to provide a very high inductance value for a low-pass filter so that its 3 dB cutoff frequency would be very low in frequency (for example, below 1 MHz or even down to 58 kHz for EAS gates). In fact, it will be understood to those skilled in the art that inductor chips could also be large value wound inductors with powdered iron or ferrite toroidal cores. In an MR scanner, the electromagnetic field environments are quite harsh, but are also well known. For example, for a 1.5 Tesla scanner, the pulsed RF field is at 64 MHz. Accordingly, the shielded three-terminal flat-through EMI/energy dissipating filter could be designed such that its parasitic flat-through capacitance along with MLCC capacitors $C_2$ would provide sufficient attenuation at 64 MHz so that the AIMD could be free from EMI and be operated safely in an MR scanner. Accordingly, it would not matter that the cores of the toroidal inductors 156 saturated and that low frequency filtering is thereby not available during the time of the MR scans. Obviously, a person in an MR scanner is not likely to encounter an EAS gate or RFID reader typically found when exiting retail stores. What is important is that after the patient is removed from the MR scanner is that the toroidal inductors (or chip inductors with ferrite cores or layers) not exhibit permanent remnance and return to their original state so that they will continue to provide effective low frequency filtering against emitters that the patient may find in their everyday environment.

Figure 73:
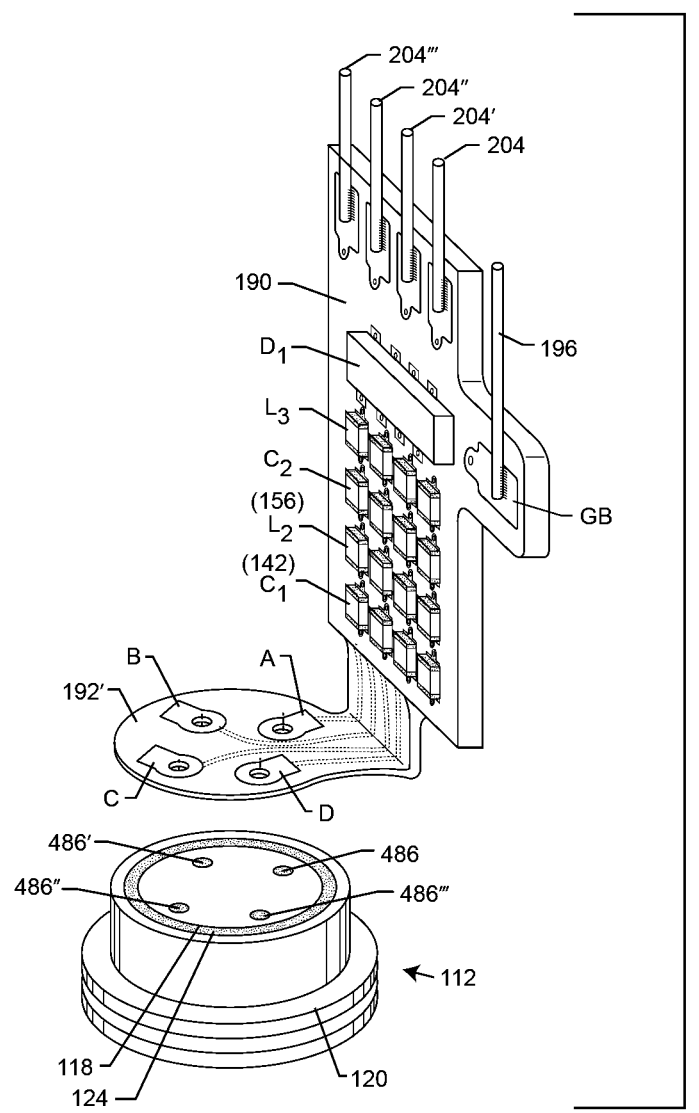
FIG. 73 is a view similar to FIG. 70, illustrating the flexibility of a portion of a hybrid substrate.

FIG. 73 illustrates the flexibility of section 192'. As one can see, it is very easy to bend the entire flex section 192' into a right angle. This is important so that the entire assembly can easily fit inside the typical spaces and geometries of active implantable medical devices, including cardiac pacemakers and the like.

Figure 74:
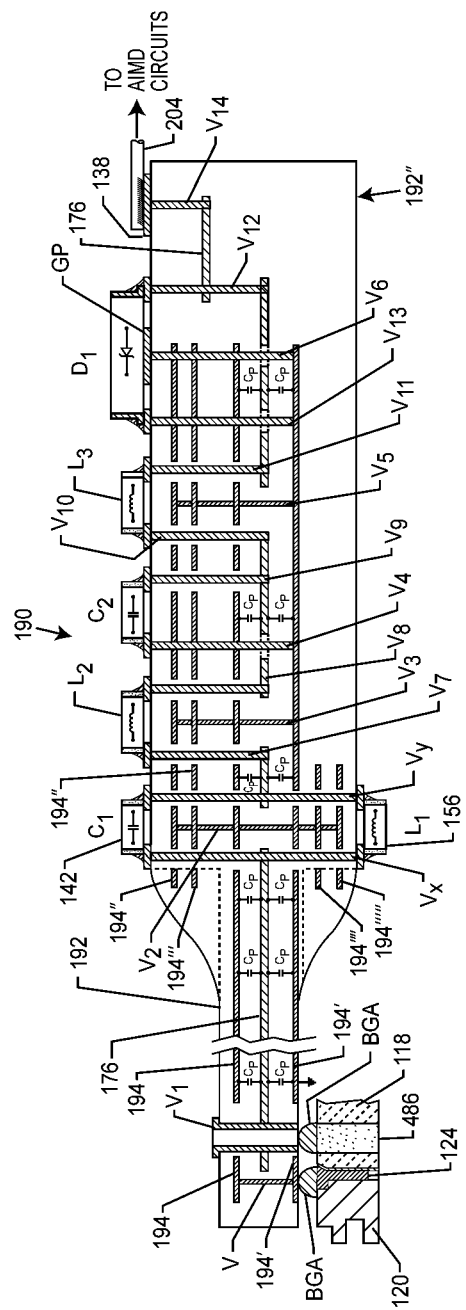
FIG. 74 is a sectional view of the novel hybrid substrate taken along lines 74-74 of the structure of FIG. 70.

FIG. 74 is a sectional view taken along lines 74-74 of the structure of FIG. 70. In FIG. 74, one can see that the gold braze 124 of the hermetic seal 112 is shown on the left. An electrical connection BGA is made between internal ground via V to shield plates 194 and 194' and the gold braze material 124. These electrodes/RF shield plates 194 and 194' extend full width throughout the flexible portion 192' and the rigid portion 192" as illustrated in accordance with the present invention. Other circumferential via holes V (not shown) are used to provide a low impedance attachment to additional points between ground shield plates 194 and 194' to the gold braze 124 of the hermetic seal as shown. There are also additional ground shields connected by via hole $V_2$ to optional/additional RF shields plates 194"-194"" as shown. As previously mentioned, it is very important that the electrical connection BGA to the gold braze 124 be multi-point connections in such that a very low impedance is achieved so that the ground shields can properly function as a faraday cage shield at high frequencies.

Starting from the left and moving along to the right on FIG. 74, we will now follow flat-through capacitor active electrode plate 176. On the left side, active electrode plate 176 is electrically connected to platinum filled via 486 from the hermetic terminal by means of via hole and eyelet $V_1$. For simplicity, we are only going to trace one of the quadpolar circuits 176, although it will be understood to those skilled in the art that the other three are of similar or identical flat-through capacitor construction techniques described herein. Parasitic flat-through capacitances $C_P$ are formed due to the ECA that is formed along the length of active electrode plate 176 which is sandwiched between the opposed grounded shield plates 194 and 194'. Via holes $V_2$, $V_3$, $V_4$, $V_5$ $V_6$, and $V_{13}$ (and others not shown) are part of a multipoint ground system so that the ground plates 194 and 194' are kept at the same low impedance shield potential. Going further to the right, one encounters via hole $V_x$ and $V_y$ which connect MLCC 142 in parallel with inductor chip 156 forming a novel resonant tank filter for attenuating MRI RF signals and the like as previously described in U.S. Pat. No. 7,363,090, and U.S. Patent Application Publication Nos. U.S. 2007-0288058 A1, U.S. 2008-0071313 A1, U.S. 2008-0049376 A1, U.S. 2008-0161886 A1, U.S. 2008-0132987 A1 and U.S. 2008-0116997 A1, the contents of which are incorporated herein by these references. As one can see, this parallel combination of inductor chip 156 and chip capacitor 142 form a parallel combination which is electrically in series with active electrode plate 176 in accordance with the referenced co-pending patent serial numbers. Having MLCC 142 and inductor chip 156 placed on opposite sides (top and bottom) of the hybrid substrate 192 is just one way to form the parallel resonant combination. For example, if one refers to FIG. 80, 85 or 87 of U.S. Patent Application Publication No. U.S. 2007-0112398A1, any of these novel integrated L-C chips could be used as a single element on top (or the bottom) of hybrid substrate 192 that would replace both MLCC 142 and inductor 156. It will be understood to those skilled in the art that the parallel bandstop filter formed by $C_1$ and $L_1$ can be placed anywhere in the active electrode circuit of the shielded three-terminal flat-through EMI/energy dissipating filter 190. In other words, it could be moved further to the right, for example, after $L_2$ or even after $L_3$. It will also be understood to those skilled in the art that any combination of circuit elements is possible, including placing circuit elements 142 and 156 in series as an inductor-capacitor (L-C) trap filter anywhere between the active electrode 176 and ground 194,194'.

Referring once again to FIG. 74, active electrode plate 176 is then routed through via hole $V_7$ through inductor $L_2$ and then back down through via hole $V_8$ back to active electrode plate 176. Active electrode plate 176 is then electrically continuous to another via hole $V_9$ which is connected to the right hand termination surface of MLCC capacitor $C_2$. The other termination end of the capacitor $C_2$ is connected through via hole $V_4$ to grounded shield substrates 194-194'''. This makes for a very low impedance RF ground connection for capacitor $C_2$. The active electrode plate 176 then continues to via hole $V_{10}$ and up and to the right through inductor $L_3$ whose other end termination returns through via hole $V_{11}$ putting $L_3$ in series with active electrode plate 176. As previously described, inductors $L_2$ and $L_3$ can be chip inductors, including ferrite chip inductors or they can be toroidal wound inductors or other types of inductors. Referring back to MLCC chip $C_1$ and $C_2$, it will be appreciated that these do not have to be monolithic ceramic. Literally any type of capacitor chip suitable for surface mounting is adaptable for the present invention. This includes stack film caps or even electrolytic capacitors. Active electrode plate 176 is then connected through via hole $V_{12}$ to the right hand side of the high voltage suppression diode array $D_1$. The left hand side of the diode array $D_1$ is connected through via hole $V_{13}$ such that it makes connection with grounded shield plates 194, 194''', 194 and then 194'. Active electrode plate 176 then exits to the right from via hole $V_{12}$ over to via hole $V_{14}$ and then up to wire bond pad 138 which is very convenient for connection of lead wire 204 as shown. A ground pad GP on top of the hybrid substrate 192 has been provided which connects by via hole $V_6$ to the embedded grounded shield plates 194", 194''', 194 and then 194'.

Referring now back to FIG. 70, one can see ground wire 196 which has been connected to the bond pad area GB. This is not required for all AIMDs, however, it is a very convenient point for connection of integrated circuit substrate 250 ground circuit trace or traces to the housing of the AIMD via lead 196 and then to the ground shield plates 194, 194' of the hybrid flex shielded three-terminal flat-through EMI/energy dissipating filter. As previously described, the ground shield plates are connected to the gold braze 124 of the hermetic seal 112 which is typically laser welded into the overall titanium housing/can of the AIMD. The housing can act as an EMI shield, an electrode or an energy dissipation surface. In all cases, a low impedance RF ground is required which is accomplished by the grounded shield plates of the shielded three-terminal flat-through EMI/energy dissipating filter 190 of the present invention. Referring back to FIG. 74, one can see that there are a number of parasitic flat-through capacitances $C_P$ that are formed in accordance with the present invention between shield plates 194 and 194' which surround active electrode plate 176 on top and bottom as shown.

Figure 75:
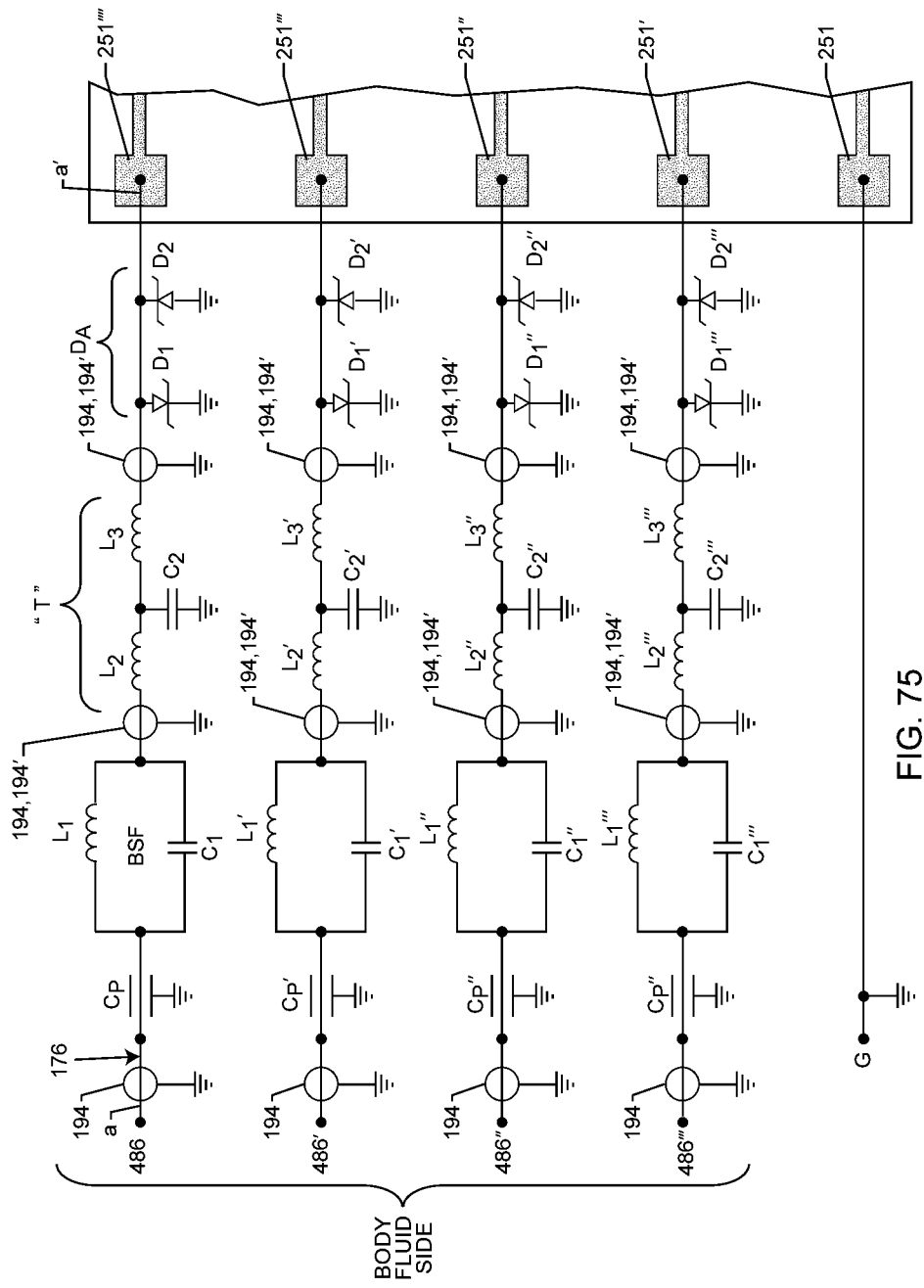
FIG. 75 is an electrical schematic diagram of the novel hybrid substrate of FIG. 70.

FIG. 75 is the schematic diagram of the shielded three terminal flat-through EMI/energy dissipating filter 190 of FIGS. 70, 72, 73 and 74. For example, tracing one of the quadpolar circuits through, for example the circuit labeled 176, point "a" is toward the body fluid side of the solid filled via 486 that connects from the hermetic seal 112 shown in FIG. 70. Typically, this would connect through a connector block or directly to a lead system where an electrode would come into contact with body tissue (in a unipolar pace or sense mode, the AIMD housing/can would serve as the return electrode). On the opposite side of the hermetic terminal, we have the same platinum filled via 486 which then connects to the via hole $V_1$ of the flexible hybrid substrate 192'. The active electrode plate 176 enters the bandstop filter BSF which consists of the parallel inductor $L_1$ and MLCC capacitor $C_1$, one sees that we have now entered the shielded part of the substrate meaning that the entire active electrode plate 176 is contained within grounded shield plates 194 and 194'. After exiting the bandstop filter BSF, we then go through inductor $L_2$, and then MLCC capacitor $C_2$ is connected to ground 194, 194'. MLCC $C_2$ is then connected with inductor $L_3$. After active electrode 176 exits inductor $L_3$, it is still shielded/sandwiched within the ground plates 194, 194' of the hybrid substrate 192. We then encounter the transient voltage suppression diode array DA. In this case, the diode array is shown connected to ground and acts as a high voltage suppression device. Diode arrays DA of this type are commonly used in AIMDs. The reason for this has to do with the use of either ICDs or automatic external defibrillators (AEDs). AEDs are now commonly deployed in government buildings, hotels, airplanes, and many other public places. These life saving devices are very important. If a person is unconscious, the AED electrodes are placed on the person's chest. The AED then automatically detects dangerous ventricular arrhythmias (such as ventricular fibrillation) and then an automated high voltage biphasic shock is applied to the electrodes. If the person has an implanted pacemaker (which is often the case) then the implanted leads pick up this high voltage shock that is being used to cardiovert the cardiac tissue. Since the implanted pacemaker is a low voltage device, this high voltage shock can damage sensitive internal circuits of the cardiac pacemaker. Accordingly, diode arrays, incorporating back to back diodes, zener diodes, transorbs or the like are commonly used to short the high voltage spike to ground before it can damage sensitive active electronic circuits (such as integrated circuits, hybrid chips and the like). Since the diode array that's typically used takes up a lot of space on the circuit board, it is a feature of the present invention that it could easily be integrated into the shielded three-terminal flat-through EMI/energy dissipating filter 190 of the present invention to save space by placing it on the interconnect circuit. We then exit the novel dissipating filter 190 of the present invention at point "a'" and make an electrical connection to the AIMD circuit board pad 251"" as shown. Another way to think of the schematic diagram shown in FIG. 75 is that what we have is a bandstop filter for suppression of MRI or other powerful single frequency emitters in series with a three element T section filter as previously described in connection with FIG. 64 in series with a high voltage suppression diode. It will be understood to those skilled in the art that the bandstop filter could be located to the right of the C, L, π, T or η element filter. It could also be placed in combination with L-C trap filter to ground. Accordingly, one can see that a number of components have been assembled into one convenient package.

Referring back to FIG. 70, there are a number of other features of the novel hybrid flex substrate 192 that need to be pointed out. One of the features is best described by referring back to FIG. 70 wherein the via holes have an enlarged rectangular portion A, B, C and D for suitable electrical probing or electrical testing. This section allows for a robot or a pogo spring connector to be placed on the pad to facilitate electrical testing, accelerated life testing, burn in, insulation test, dielectric withstanding voltage test or other suitable electrical tests as needed. These tests, often performed at elevated temperatures, are essential to assure the long term reliability of the novel shielded three-terminal flat-through EMI/energy dissipating filter of the present invention. In the opposite (right) end of the rigid part of the substrate 192", a similar enlarged pad area(s) 139 has been provided for similar electrical contact for test instruments as previously described. For ease of manufacturing, it is also convenient that the entire hybrid flex substrate 192 be laid flat as is shown. Being laid flat is particularly suitable to be placed into fixtures for modern robots. These robots are typically fed by tape and reel components or trays which house all of the electronic components. By having the basic hybrid substrate 192 lying flat, all of the components can be quickly placed by the robots. Assembly by hand is impractical due to the small size of the surface mounted components. For example, the MLCC chips can be 0201 or smaller which is the size of a grain of pepper that would come through a pepper shaker (0.020 inch by 0.010 inch). It is then a matter of prior art wave-soldering or equivalent techniques to make the electrical and mechanical connections to all of the components. This is followed up by automated optical inspection, electrical test and even X-ray if needed.

Again referring to FIG. 70, so that adequate electromagnetic interference protection will be provided to sensitive AIMD electronics and sense circuits, the inductor $L_2$ will preferably be of a non-ferrite core and the capacitor $C_2$ would be of sufficient value working in conjunction with flat-through capacitance $C_P$ such that those components alone would provide adequate protection at MRI pulsed frequencies. For example, for 1.5 Tesla MR scanner, the RF pulsed frequency is 64 MHz. It would be desirable for component $C_P$, $L_2$ and $C_2$ to have over 40 dB attenuation at 64 MHz to provide adequate protection to device electronics. With the use of a very high value inductor $L_3$, as illustrated in FIG. 72, one can provide a very high degree of (attenuation) immunity to low frequency emitters, such as 58 kHz electronic article surveillance (security) gates that are typically used in retail stores. In addition, one can provide a great deal of immunity to low frequency LF RFID readers. These are typically used for automotive keyless entry systems and the like. Since neither RFID readers nor store security gates are present in an MR scan room, it does not matter if inductor $L_3'$ does saturate in the MR environment. Accordingly, a novel methodology is provided in the hybrid substrate 192 such that certain filter components do not saturate during the MR scan and others do. It will be understood to those skilled in the art that capacitor elements $C_2$ could be a monolithic ceramic capacitor (MLCC), or a very high value aluminum electrolytic or tantalum capacitor. In other words, for very low frequency filtering, a capacitor of several microfarads could be used with a toroidal wound inductor of several hundred microhenries. This would provide attenuation down to very low frequencies.

In FIG. 75, one can see that $L_2$ working in combination with $C_2$ and $L_3$ form what is known in the art as a low-pass "T" filter. Any combination of active or passive circuit elements can be readily adapted to the shielded three-terminal flat-through EMI/energy dissipating filter of the present invention. This includes any of the low-pass filter circuits shown in FIG. 66, and any combinations of L-C traps and/or bandstop filters (BSFs). It is a feature of the present invention that the three terminal flat-through capacitance obtained by sandwiching large surface area through electrodes between surrounding ground plates result in a flat-through capacitance suitable to compensate for the self-resonance characteristic of prior art (and very low cost) MLCCs and allow them to be used in combination with the shielded three-terminal flat-through EMI/energy dissipating filter of the present invention to achieve a very broadband and effective EMI filter and highly effective energy dissipater.

Figure 76:
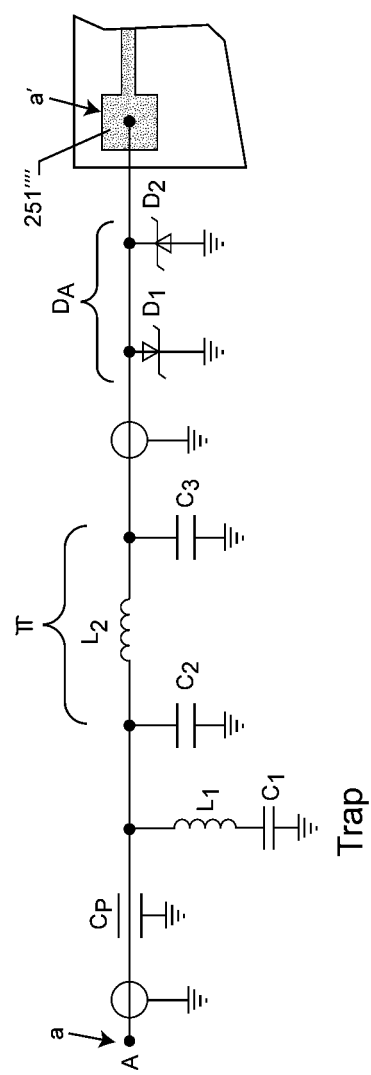
FIG. 76 is the same as one of the active circuits of FIG. 75 wherein the "T" circuit filter has been replaced with a π circuit filter.

FIG. 76 is an electrical schematic for one circuit A of FIG. 72. In this case, the T circuit low-pass filter has been replaced with a π circuit low-pass filter consisting of $C_2$, $L_2$ and $C_3$. In FIG. 76, the bandstop filter BSF consisting of components $L_1$ and $C_1$ acting in parallel, has been replaced by a L-C trap filter consisting of $L_1$ and $C_1$ that are wired in series to ground 194, 194'. It is well known that when L-C series components are in resonance, they ideally form a short circuit at the resonant frequency. This is more thoroughly described in U.S. Pat. No. 6,424,234 the contents of which are incorporated herein. Referring once again to FIG. 76, when one is designing the trap circuit, one has to be very careful of the parallel action of $C_P$ and $C_2$. One has to model the circuit very carefully to make sure that the trap filter functions properly in the presence of these parallel capacitances. It is often desirable, and well known in the art, to isolate the L-C trap filter with a series bandstop filter so that it will not interact with other parallel capacitances. It will be understood to those skilled in the art that a bandstop filter could be inserted on one or both sides of the trap filter or between multiple trap filters to increase its or their efficacy.

Referring once again to FIG. 72, the use of a trap filter would be particularly advantageous if the AIMD were to be exposed to an MRI environment. For example, if the system were designed to be used in a 1.5 Tesla scanner, the trap filter could be designed to be resonant at 64 MHz. This would short out 64 MHz signals to ground (the titanium housing of the AIMD). This would not only provide a great deal of immunity and protection to device electronics, it would also desirably short MR energy to the metallic housing of the AIMD such that it cannot reflect back and cause overheating of the distal electrode tip to tissue interface. Using the housing to dissipate energy is described in U.S. Provisional Patent Application No. 61/144,102, the contents of which are incorporated herein.

Referring once again to FIG. 76, the π circuit could consist of an MLCC capacitor $C_2$ which would be very effective at high frequencies. $L_2$ could be a toroidally wound inductor with a ferrite core as previously described as $L_3'$ from FIG. 72. $C_3$ could be a high value tantalum capacitor. It would not matter if the π circuit was effective while the AIMD was operating in a MR scanner. This is because the L-C trap would be made of components which do not saturate in a magnetic field environment. In other words, inductor $L_1$ would be non-ferromagnetic and capacitor $C_1$ would generally be of MLCC construction. Therefore, the EMI filtering immunity for the MR environments would consist entirely of the operation of the trap filter operating in combination with the parasitic capacitance (flat-through capacitance) of the novel hybrid substrate 192 of the present invention. Accordingly, the π section filter would be very effective when the patient is outside of MR environments for attenuating low frequency signals and signals throughout the frequency range. In other words, the structure as illustrated in FIG. 76 would perform effective filtering from approximately 30 kHz all the way to 10 GHz while outside of an MR environment. While in an MR environment, it would perform effective filtering at selected frequencies of one or more trap filters as shown. Only one trap filter is shown, but it will be understood to those skilled in the art that any number of trap filters could be placed in parallel in order to short circuit multiple RF frequencies. For example, if one were to want the AIMD to be compatible with both 1.5 and 3 Tesla scanners, then two trap filters would be required; one resonating at 64 MHz and the other one at 128 MHz. Again, as previously stated, the L-C trap filter can each be separated by a series bandstop filter consisting of a capacitor in parallel with an inductor so that the components of each individual trap filter do not interact with each other.

Reference is made to U.S. Provisional Patent Application Ser. No. 61/144,102, which describes a number of other frequency selective circuits that can be used to balance the energy during MRI scanning. The objective is to take as much energy off the implanted lead system and shunt it to the conductive housing of the AIMD which then becomes its own energy dissipating surface. It will be understood to those skilled in the art that any and all of the schematics that are disclosed in U.S. Provisional Patent Application Ser. No. 61/144,102 can be embodied in the novel hybrid substrate 192 of the present invention.

Figure 77:
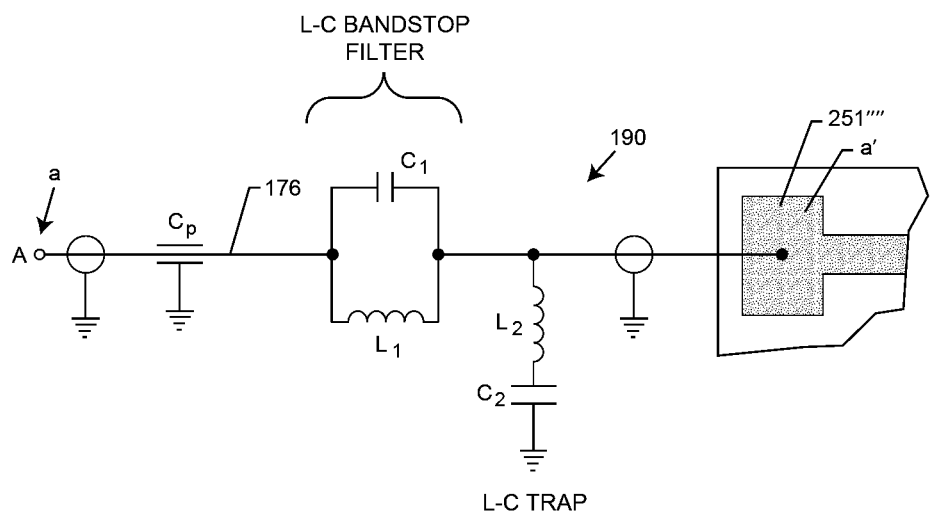
FIG. 77 is the same as one of the active circuits of FIG. 75 now showing a capacitor, bandstop filter and L-C trap filter.

FIG. 77 illustrates another alternative embodiment of the shielded flat-through 190 previously described in FIGS. 74 and 75. In this case, there is a capacitance $C_P$, which can be the parasitic capacitance of the flat-through filter or it can be the parasitic capacitance of the flat-through filter combined with a feedthrough filter (previously shown as element 132 in FIG. 62) or the MLCC chip. Referring once again to capacitance $C_P$, what is really important is that when looking at the AIMD from the point of view of an implantable lead, that a significant capacitance is seen first. This forms a capacitance from active circuit trace 176 to ground wherein, ground is the potential of the AIMD housing and then in series with the circuit trace 176 is an L-C bandstop filter consisting of capacitor $C_1$ in parallel with an inductor $L_1$ and then an L-C trap consisting of inductor $L_2$ in series with capacitor $C_2$ disposed from circuit trace 176 to ground, all of which is shielded in accordance with the present invention. Resistance elements can be added in series with $C_1$, $L_1$, $L_2$ or $C_2$ in order to control the Q and resultant 3 dB bandwidth of the L-C bandstop filter and/or the L-C trap filter. The circuit described in FIG. 77 provides a very high degree of immunity to AIMD sensitive electronic ports particularly in the presence of a high power emitter, such as an MRI scanner. The RF frequency of the MRI scanner has a very high amplitude and is not adequately attenuated by single element filters. The filter of FIG. 77 consists of a capacitance then a bandstop filter and then an L-C trap. For example, for a 1.5 Tesla MRI scanner, the RF-pulsed frequency is approximately 64 MHz. With the L-C bandstop filter tuned to be resonant at 64 MHz, this would present a very high impedance to the RF-pulsed frequency. For any RF signal that got past the L-C bandstop filter, the L-C trap filter would also be tuned to be resonant at 64 MHz. This means that at 64 MHz, it would tend to look like a short circuit. Accordingly, referring once again to FIG. 77, very little to no 64 MHz RF energy could penetrate such a three stage filter and enter at point a'.

Figure 78:
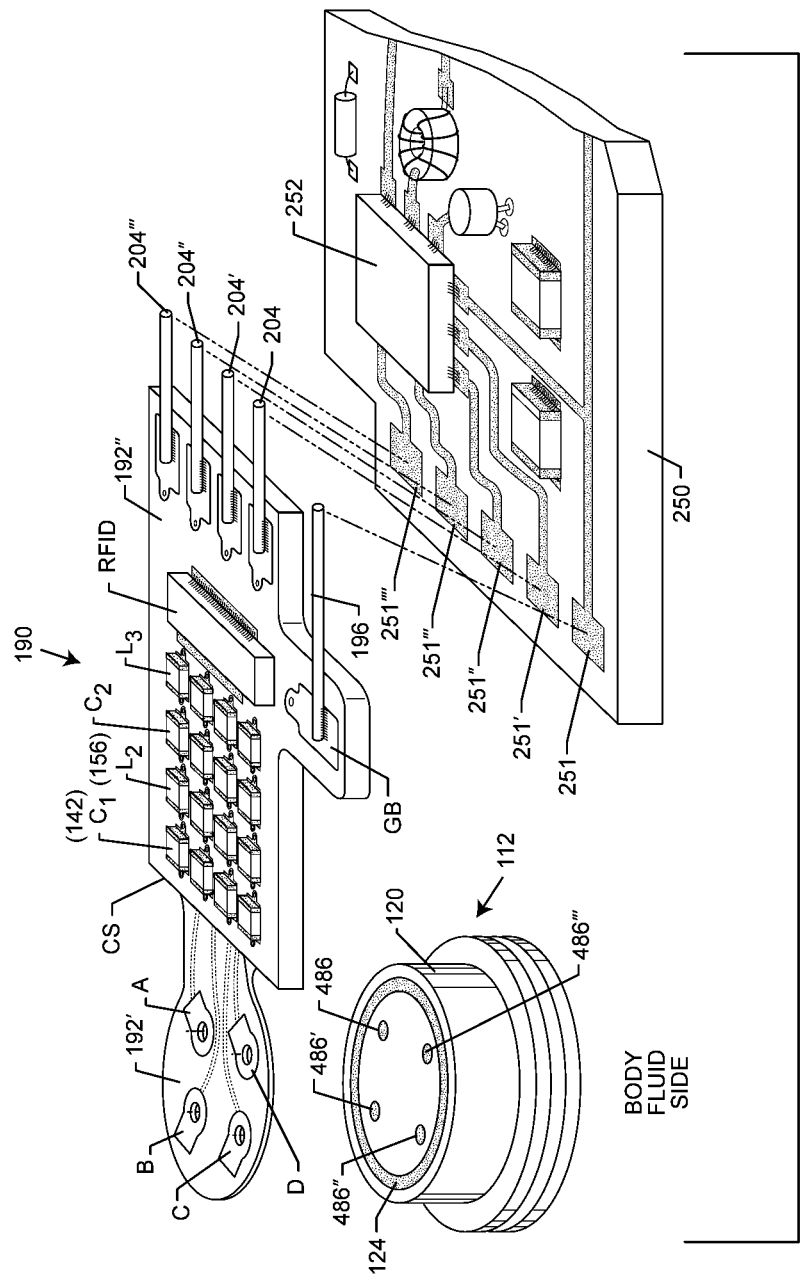
FIG. 78 is similar to FIG. 70, with the addition of a prior art quadpolar feedthrough capacitor.

FIG. 78 is very similar to FIGS. 70, 71 and FIG. 72. It is understood that a prior art feedthrough capacitor 132 (not shown) could be used in conjunction with the dissipating filter 190 of the present invention. Feedthrough capacitors are well known in the prior art, including U.S. Pat. Nos. 4,424,551; 5,333,095; 5,905,627; and 6,765,779, the contents all of which are incorporated. Referring once again to FIG. 78, one can see that the diode array has been replaced by an RFID chip. Of course, the RFID chip could be added in addition to a diode array (not shown). The addition of an RFID chip can be very important so that in an emergency room, an ambulance or other emergency personnel could rapidly determine what kind of an active implantable medical device a patient has implanted. Physician members of the Association for the Advancement of Medical Instrumentation—Cardiac Rhythm Management Device Committee (AAMI_CRMD) have reported a variety of conditions at which patients will show up at an emergency room. Sometimes these patients are comatose, having suffered a heart attack. This often happens at a place like South Florida, where they may be wearing a bathing suit and have no identification or pacemaker identification card on them. Other patients wander in a state of dementia and are unable to describe what kind of device they have. If the patient is in hemodynamic stress due to low cardiac output, ER physicians, by palpitation, rapidly determine that some sort of device is present, usually in a pectoral pocket. The problem is they do not know who the manufacturer is and worse yet, they do not even know if it is a pacemaker, an ICD or even a neurostimulator, like a deep brain stimulator. What often happens is they panic as people run all around the hospital trying to find and locate manufacturer's device programmers. For example, they may attempt to see if a Medtronic programmer will communicate with the implanted device and failing that, they will go find a St. Jude programmer and so on. Accordingly, there is a need in the industry to rapidly determine what type of device and model numbers are implanted within a patient. The RFID chip, shown in FIG. 78, can be pre-programmed with the device model number, serial number, date of implant and with informed patient consent, even information about the patient or the implanting physician. In this way, all the emergency room needs is one universal RFID reader and they could rapidly scan any active implanted device and rapidly determine what is in there. This would greatly assist in reducing time, which can be critically important in an emergency room situation. Referring once again to FIG. 78, the feedthrough capacitor 132 would provide high frequency filtering generally in the frequency range from 100-10,000 MHz. As described for FIG. 72, the other board mounted components could then all involve very high capacitance tantalum or aluminum electrolytic capacitors, or toroidal inductors using high permeability ferrite cores. For example, feedthrough capacitor 132 would provide sufficient immunity during an MRI scan such that the other components could all saturate. This would provide a very effective broadband filter operating generally in the frequency range from 10 MHz all the way to 10 GHz.

Figure 79:
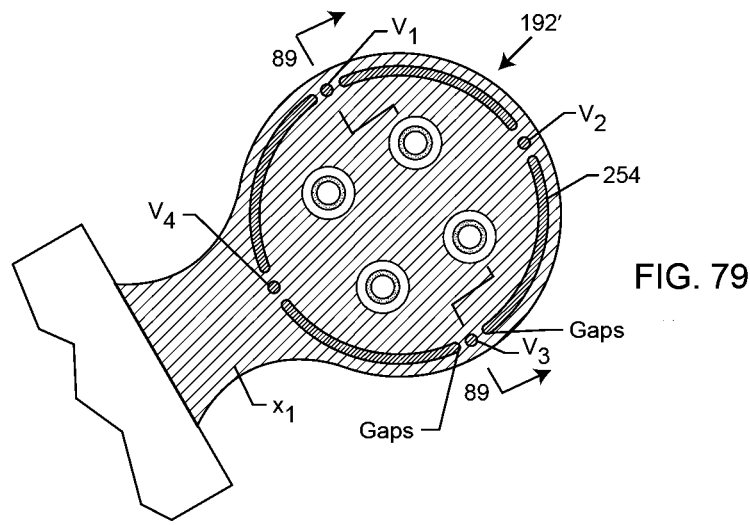
FIG. 79 is a top plan view of the reverse side of the flexible portion of the hybrid substrate of FIGS. 70 and 74.

FIG. 79 illustrates the reverse side of the flexible portion 192' of the hybrid flex from FIG. 74. One can see that a robot has dispensed a circular portion of thermal-setting conductive thermal setting adhesive 254. This is designed to align precisely with the gold braze 124 of the hermetic terminal 112 of FIG. 70. Accordingly, the entire substrate can be laid down over the hermetic terminal assembly 112 and then the thermal-setting conductive material 254 can be cured in an oven, furnace or other equivalent process. This makes a suitable electrical and mechanical connection to the exposed ground shield electrode plate 194'. Referring back to FIG. 79, one will see that there are gaps left in the circumferential thermal-setting conductive polymer 254. These gaps are present to allow for a free flow of helium during fine leak detection as previously described. There are also via holes $V_1$, $V_2$, $V_3$ and $V_4$ which are used to connect to the other internal ground shield plates, including plate 194.

Figure 80:
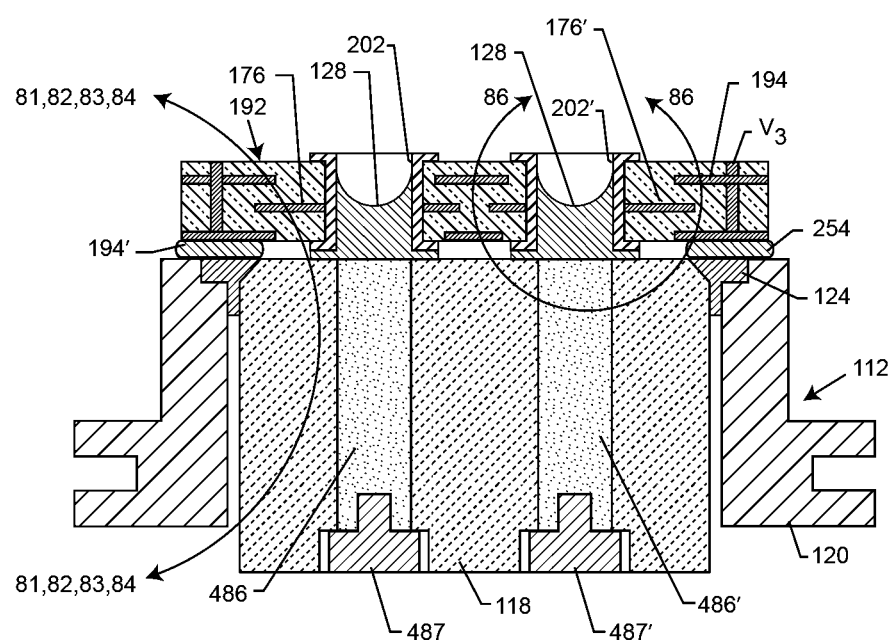
FIG. 80 is a sectional view taken generally along the line 80-80 of FIG. 79.

FIG. 80 is a sectional view taken along line 80-80 from FIG. 79. One can see the electrical connection formed by thermal-setting conductive adhesive 254 between via hole $V_3$ and the gold braze 124, for example. Referring once again to FIG. 80, one can see the platinum filled vias in the alumina hermetic insulator 486 and 486'. An electrical connection material 128 is used in via hole 202 to make an electrical connection between the platinum filled via 486, the via hole 202 and active electrode 176. Electrical attachment material 128 is also used to make a second electrical connection between via hole 202' and platinum filled via 486' and circuit trace 176'. It will be appreciated that this a quad polar device and these represent two of the circuit attachments. There will be active circuits 176, 176', 176" and 176'" in accordance with the present invention. It will be understood to those skilled in the art that any number of circuits 176 varying from 1 all the way to "n" could be embodied. Electrical attachment material 128 could be a reflow ball grid array (solder), a thermal-setting conductive adhesive, a weld, a braze and the like. Alternative methods of performing this low impedance RF electrical ground connection to the grounded shield plates 194, 194' of the shielded three-terminal flat-through EMI/energy dissipating filter 190 of the present invention are illustrated in FIGS. 81 through 84. Referring once again to FIG. 80, one can see that there are two wire bond pads 47 and 47' disposed on the body fluid side. These are generally platinum or similar biocompatible material that are co-fired along with the solid platinum filled vias 486. These make a highly conductive and mechanically strong mounting pad for laser welding, thermal sonic, ultrasonic or other types of biocompatible attachment of leadwires inside of an AIMD header or connector block or the like.

Figure 81:
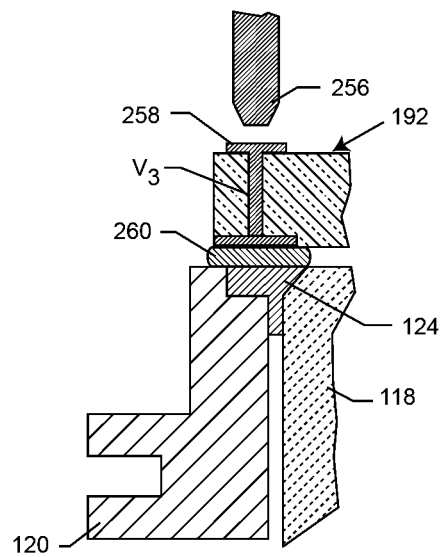
FIGS. 81-84 are fragmented sectional views taken generally of the area indicated by the line 81, 82, 83 and 84 in FIG. 80, showing alternative methods of making an electrical connection.

FIG. 81 illustrates a methodology of pushing a resistance welding electrode pad 256 onto a flex cable rivet eyelet 258 thereby creating a current flow in which an elevated temperature results sufficient to reflow a low temperature braze 260 solder or the like to the gold braze material 124.

Figure 82:
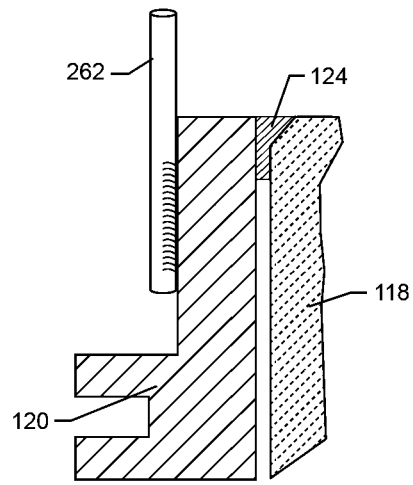

FIG. 82 illustrates an outer pin 262 which has been laser welded to the ferrule 120. The minimum number of pins is one, but an optimal number would be four to six to provide suitable RF connection to the internal grounded shield plates 194 and 194' of the present invention.

Figure 83:
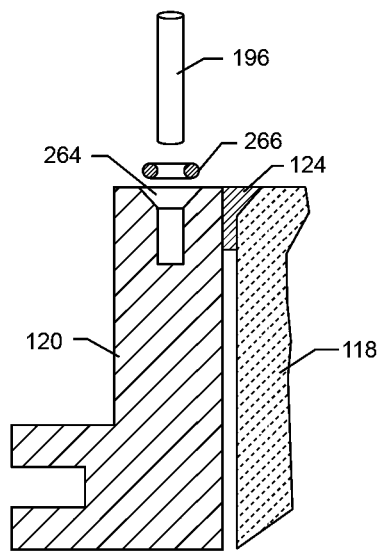

An alternative method is shown in FIG. 83 wherein a series of counterbores or countersinks 264 have been provided in the top of the flange 120 such that multiple lead wires 196 could be placed along with gold braze rings 266. A high temperature brazing furnace is used to reflow the gold preforms 266 and electrically and mechanically attach the pins/leads 196 to the ferrule 120. In this way, a number of ground pins 196 would be sticking up such that open via holes of the flexible portion 192' of hybrid substrate 192 of the present invention could be laid down and electrically attached to the grounded shield plates 194, 194'.

Figure 84:
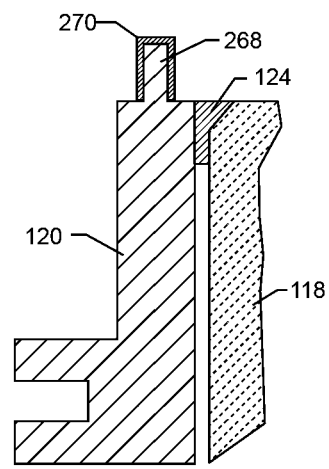

Another RF ground attach methodology is shown in FIG. 84 wherein the ferrule 120 is of a pressed powder metallurgy. In this case, a pedestal pin 268 (4 to 6 or more is the ideal number of pedestals) is formed as part of the powder metallurgy process. In this case, all the materials would be typically of titanium which is ideal for this purpose. Because of the problems with titanium oxide formation, a gold sputtering 270, plating or brazing is placed over the terminal pedestal 268 such that a proper oxide-free electrical connection can be made to the hybrid substrate 192 of the present invention.

Figure 85:
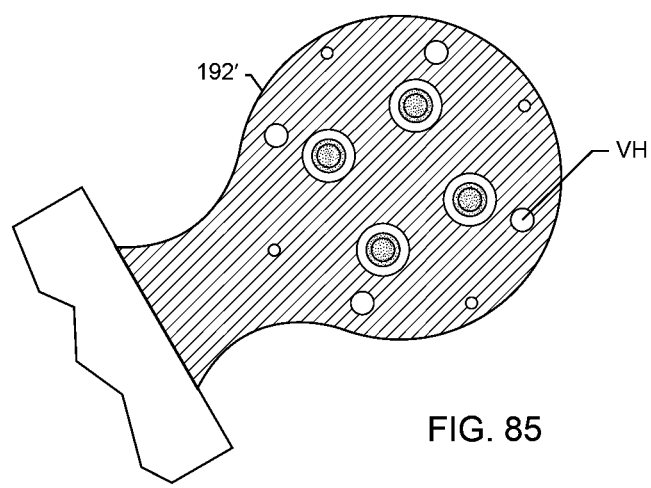
FIG. 85 is a top/plan view similar to FIG. 79 showing a modified version of flex cable assembly with four via holes.

FIG. 85 shows a modified version of the flexible portion 192' of the flex cable assembly of FIG. 70 with four (or more) via holes VH suitable for placement over any of the embodiments described in FIGS. 82 through 84 for electrical attachments to its grounded shield plates 194 and 194'.

Figure 86:
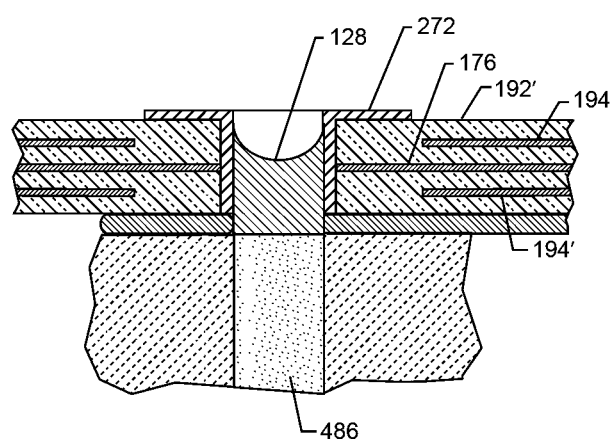
FIG. 86 is an enlarged sectional view of the area indicated by line 86-86 of the structure of FIG. 80, showing type of yet another embodiment illustrating attachment of the substrate over a terminal pin utilizing a weld ring or a braze ring.

FIG. 86 illustrates a cross-section 86-86 adapted from FIG. 80 of yet another embodiment illustrating attachment of the active electrodes 176 of substrate 192' over a platinum filled via 486 along with some sort of external metallization 272 that extends on top of the substrate 192'.

Figure 87:
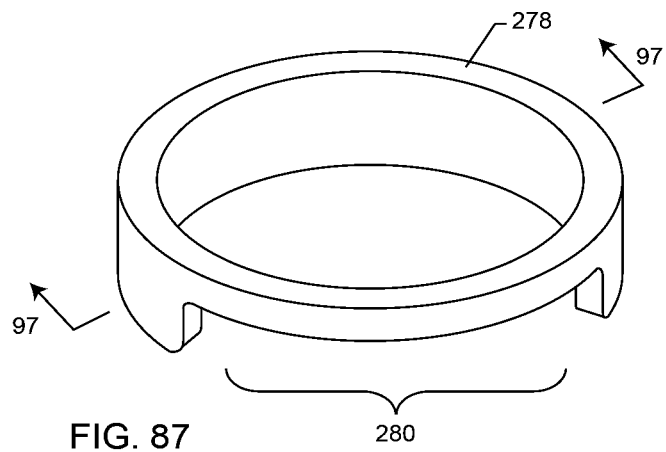
FIG. 87 is a perspective view of a novel attachment cap used to connect the shielded three-terminal flat-through EMI/energy dissipating filter to various types of hermetic or non-hermetic seals.

FIG. 87 illustrates a novel laser weld cap 278 with a cut out section 280. The cut out area 280 is formed or cut so the metal cap 278 can slip down over the narrow section 192' of the flexible portion of the shielded three-terminal flat-through EMI/energy dissipating filter 190. The laser weld cap 278 can be a stamped titanium, machined titanium, injection molded titanium or a number of other metals.

Figure 88:
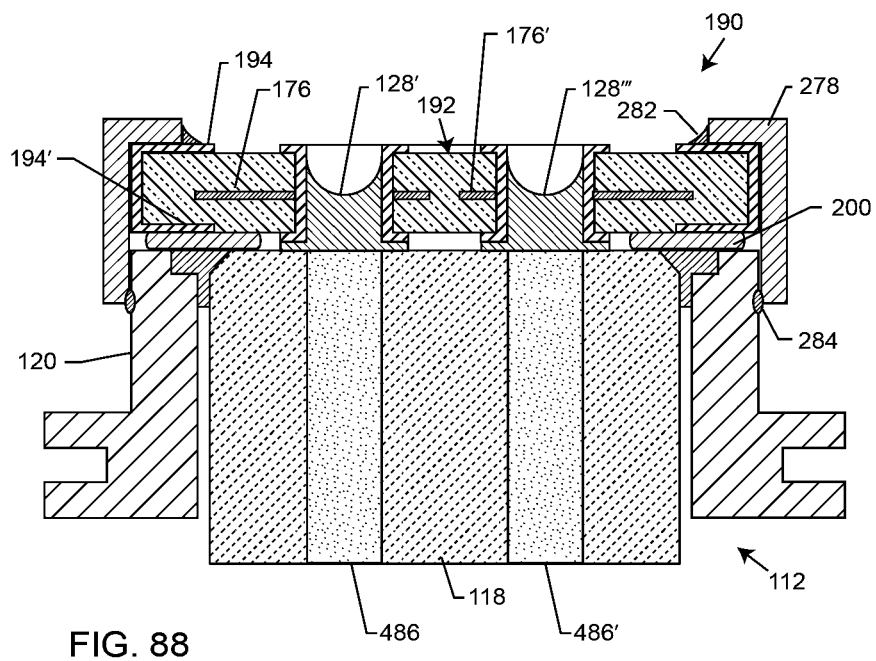
FIG. 88 is a sectional view of a prior art hermetic seal embodying the novel cap from FIG. 87.

FIG. 88 is a combined cross-section taken generally from 88-88 from FIG. 87 and also from section 88-88 from FIG. 70. However, the hybrid substrate 192 has been modified to accommodate the novel laser weld cap 278. In FIG. 88 one can see that the laser weld cap 278 is slipped down such that it comes into close contact with the flange 120 of the hermetic terminal 112. A continuous or discontinuous laser weld or braze 284 is formed as shown. This makes a solid metallurgical and low impedance ground contact to the hermetic flange 120 and to the laser weld cap 278. An electrical connection 282 is then made to the ground metallization 194 of the shielded three-terminal flat-through EMI/energy dissipating filter 190 thereby providing a very low impedance RF ground. One can see in FIG. 88 that ground shield plates 194 and 194' are external for the purposes of this illustration. However, they could be internal plates as previously illustrated.

Figure 89:
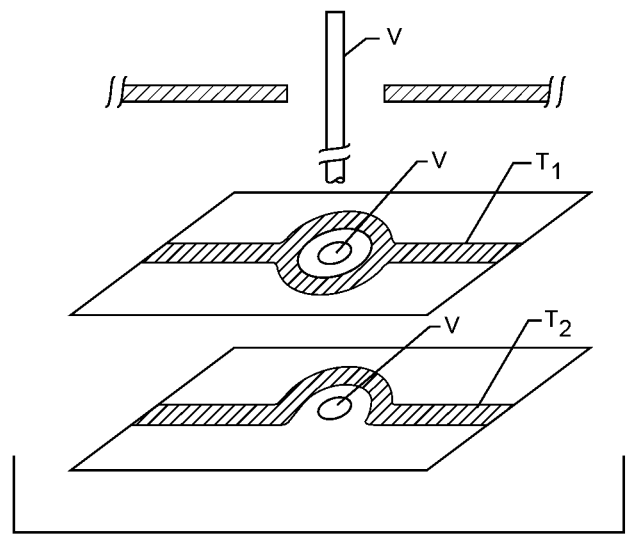
FIG. 89 is an oblique view illustrating a methodology of having a circuit trace or a portion of an electrode plate dodge around a via hole.

FIG. 89 is applicable to many of the illustrated embodiments of the present invention and simply illustrates a methodology of having a circuit trace $T_1$ or $T_2$ dodge around a via hole V such that it maintains a high surface area (to maximize ECA) and remains in electrical isolation. As one can see in the upper view circuit trace $T_1$ can be routed in a circular manner all around the via hole or it can simply be routed around the via hole. To maximize flat-through capacitance ECA, the upper trace is the preferred embodiment.

Figure 90:
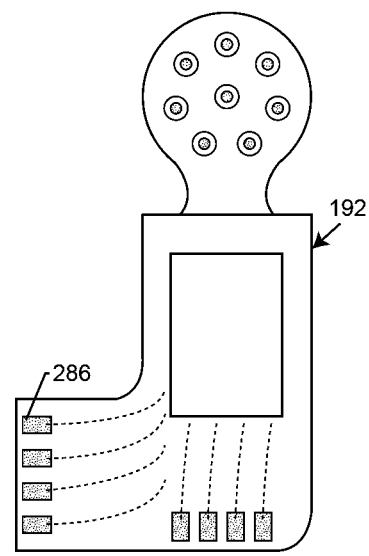
FIG. 90 is a top/plan view illustration of an alternative embodiment to FIG. 70.

FIG. 90 illustrates an alternative embodiment to FIG. 68 in that it is an octapolar design instead of a quadpolar design. Also, instead of having lead wires for transition to integrated circuit boards, it has wire bond pads 286 for convenient connection of jumper wires to other circuits.

Figure 91:
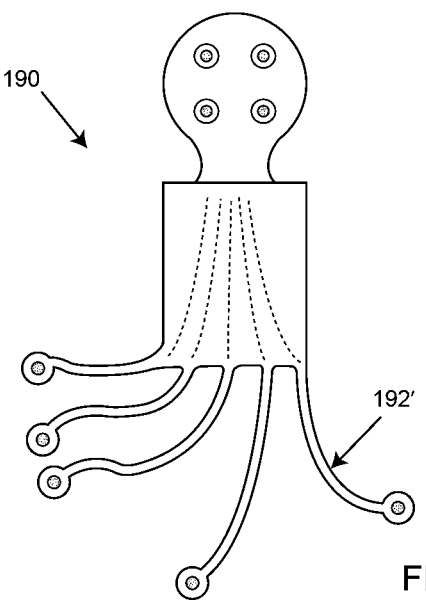
FIG. 91 is similar to FIG. 90, except that it illustrates the methodology of breaking up flex cable section of the hybrid substrate into flexible sections.

FIG. 91 is very similar to FIG. 90 except that it illustrates the methodology of breaking up the flex cable portion 192' of the hybrid substrate 192 into individual arms/traces for direct electrical connection to other locations, for example to an IC board, within a general electronics module or an AIMD.

Figure 92:
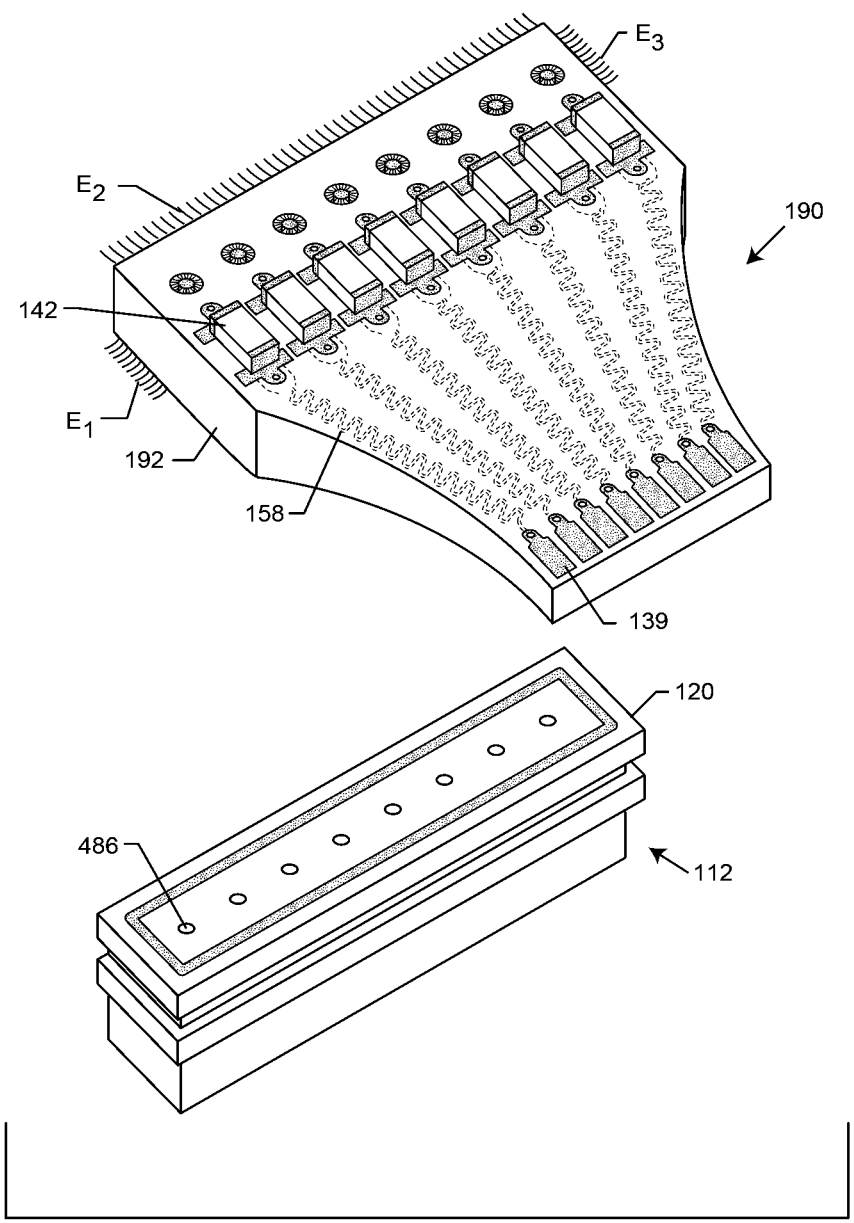
FIG. 92 is an exploded isometric view of an in-line octapolar hermetic terminal with a shielded three-terminal flat-through EMI/energy dissipating filter hybrid flat-through substrate embodying the present invention.

FIG. 92 illustrates an in-line octapolar hermetic or non-hermetic terminal 112 with a hybrid substrate 192 of the present invention exploded away from it, but designed to be mounted to it. One can see that there are a number of MLCC capacitors 142 that are in series with an embedded inductor meander 158. Wire bond pads 139 are provided at the end for convenient connection of jumper wires to AIMD or other electronic device electrical circuits.

The present invention may be manufactured in accordance with the manufacturing production flow chart provided in U.S. patent application Ser. No. 13/873,832.

Figure 93:
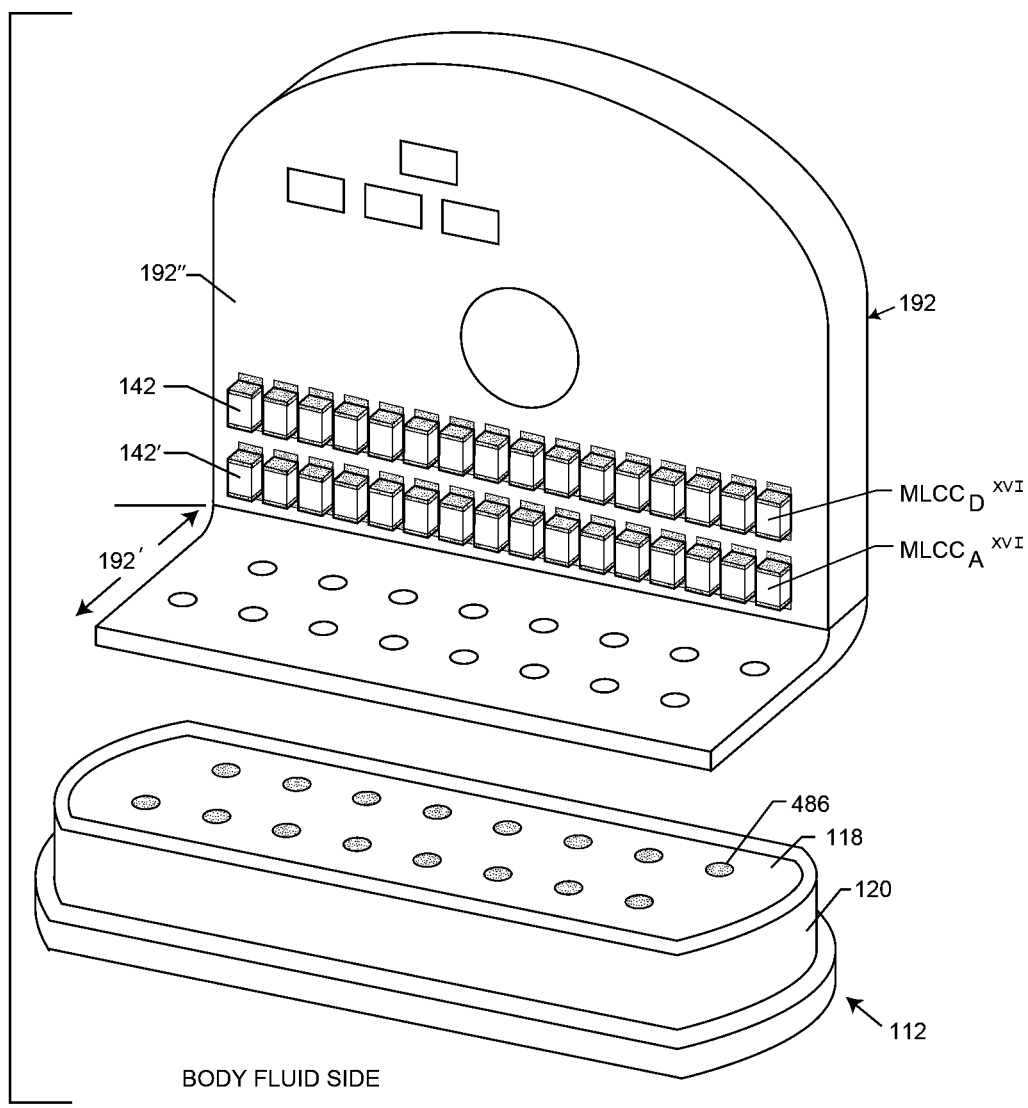
FIG. 93 is an exploded oblique view of a typical sixteen lead hermetic seal utilizing a novel hybrid shielded three-terminal flat-through EMI/energy dissipating filter embodying the present invention.

FIG. 93 illustrates a 16-via hermetic seal 112 for use in a cochlear implant. Shown is a novel hybrid substrate 192 of the present invention which consists of a rigid section 192" and a thin flexible section 192'. A number of MLCC capacitors 142 are shown mounted. Not shown are internal ground shield plates of the present invention. With this embodiment, mounted MLCC's D can be used to provide DC blocking while MLCC's $_A$ can be combined with the flat-through filters to provide EMI filtering.

Figure 94:
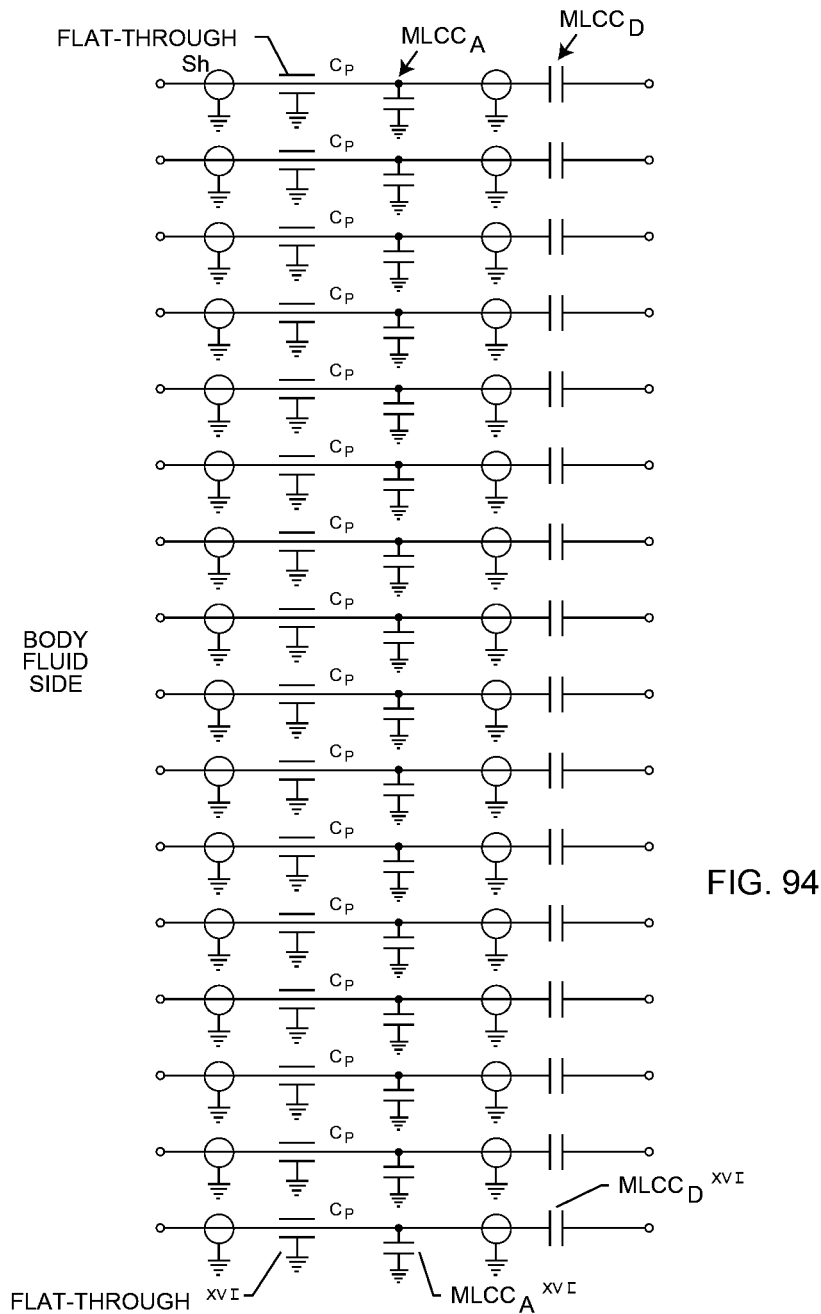
FIG. 94 is an electrical schematic diagram of the structure of FIG. 93.

Referring to the body fluid side of FIG. 94, starting with the top schematic, as we enter into the shielded area Sh, the flat-through parasitic capacitances $C_p$ that are formed in the present invention between embedded ground shields (not shown) and the particular circuit electrode is encountered. Next an $MLCC_A$ is encountered which provides additional low frequency EMI filtering in accordance with the present invention. Then an $MLCC_D$ is entered in series which is a DC blocking capacitor which is placed in series with the circuit trace. Note that since they are both shielded, the order of $MLCC_A$ and $MLCC_D$ can be reversed without loss of EMI attenuation or body tissue protection. The purpose of series DC blocking capacitor $MLCC_D$ is to prevent DC bias from reaching body tissue and possibly causing damage or necrosis. In fact, these DC blocking capacitors are well known in the art and are generally required by regulatory agencies, such as the Federal Food and Drug Administration (FDA).

Figure 95:
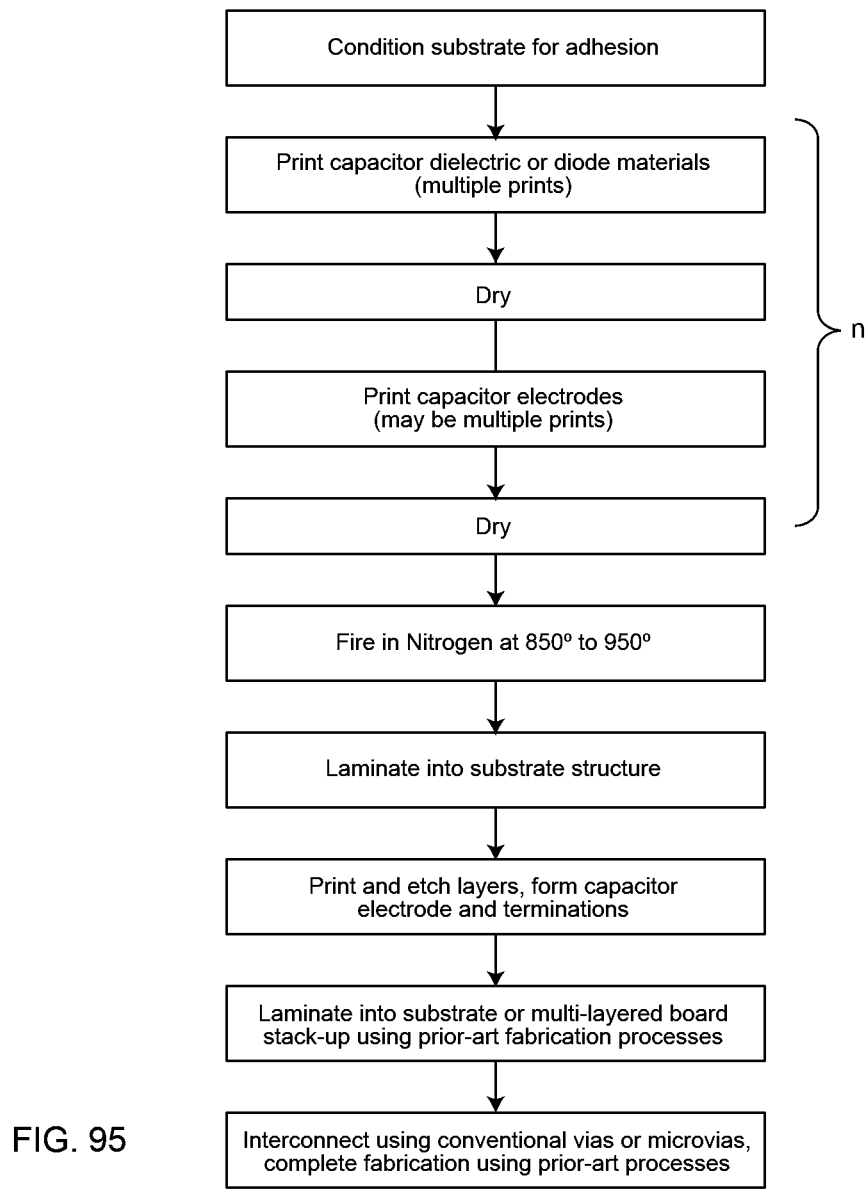
FIG. 95 is a flow chart illustrating an exemplary manufacturing process of the electronic components of the present invention.

FIG. 95 is a manufacturing flow chart that describes an alternative method of manufacturing any of the electronic components of the present invention. Monolithic ceramic capacitor manufacturing is well known in the art. However, a more efficient and cost effective way to do this would be to use thick film technology and lay down the components of the shielded three-terminal flat-through EMI/energy dissipating filter 190 all at one time all on one hybrid substrate 192. Referring to FIG. 95, you would first condition the substrate for adhesion of the various dielectric and electrode materials. Then you would print the capacitor dielectric or diode materials through multiple print operations. There is typically a drying operation between each multiple printing operation. This can be done literally in as many times (end times) as required until one reaches the desired capacitance value, inductance value or the like. The thick film component is then typically fired in nitrogen at temperatures ranging from 850 to 950 degrees C. This is then laminated into a substrate structure. The layers are printed and etched to form capacitor electrodes and terminations and this is laminated into a substrate or multi-layer board and stacked up using prior art application processes. There are then interconnects using conventional vias or micro-vias to complete the fabrication again using all prior art processes.

The novel hybrid substrate 192 of the shielded three-terminal flat-through EMI/energy dissipating filter 190 of the present invention can also be used to mount a variety of sensing circuits to be used in conjunction with external or lead-based sensors. For example, for a cardiac pacemaker application, a number of physiologic sensors could be mounted on the novel substrate, including respiration rate sensors, blood pH sensors, ventricular gradient sensors, cardiac output sensors, pre/post cardiac load sensors, contractility sensors, hemodynamics and pressure monitoring sensors. Such components could also be used in conjunction with blood gas or oxygen sensors.

Figure 96:
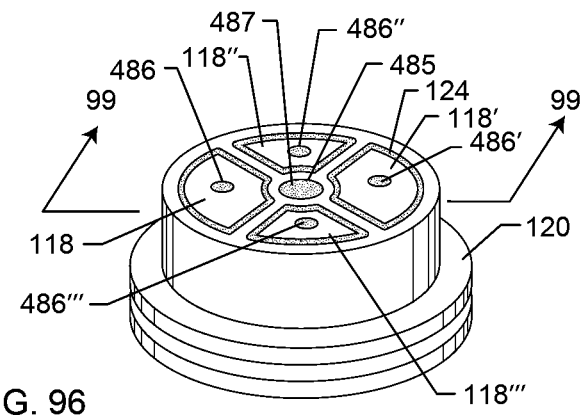
FIG. 96 is an oblique view of a quadpolar hermetic seal similar to that shown in FIG. 30, now embodying a novel pocket formed in the ferrule for an internal ground connection for connection to an internally grounded platinum fill in a filter capacitor.
Figure 99:
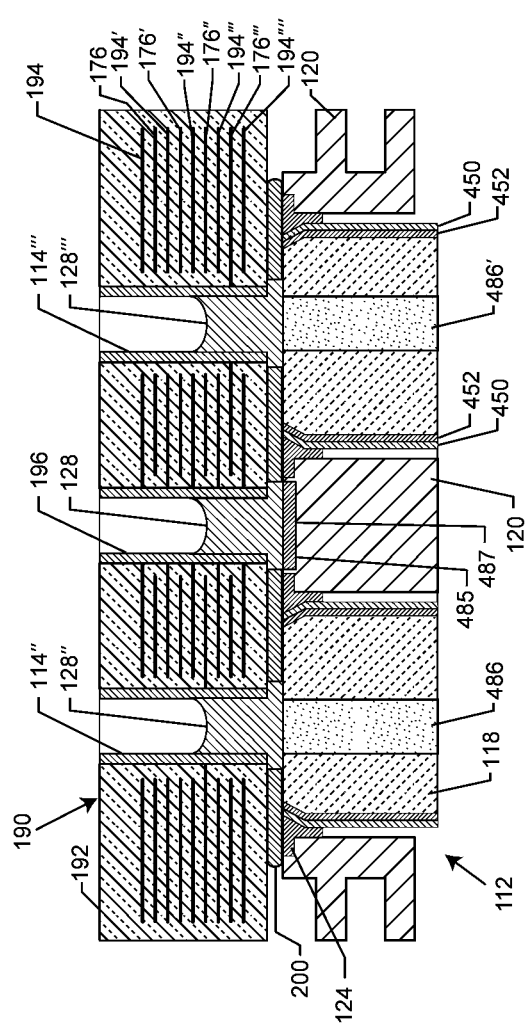
FIG. 99 is a sectional view taken along lines 99-99 from FIGS. 96-98 now with a filter and showing the internal connection between the platinum fill in the filter capacitor to the ferrule.
Figure 11:
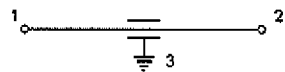
Figure 12:
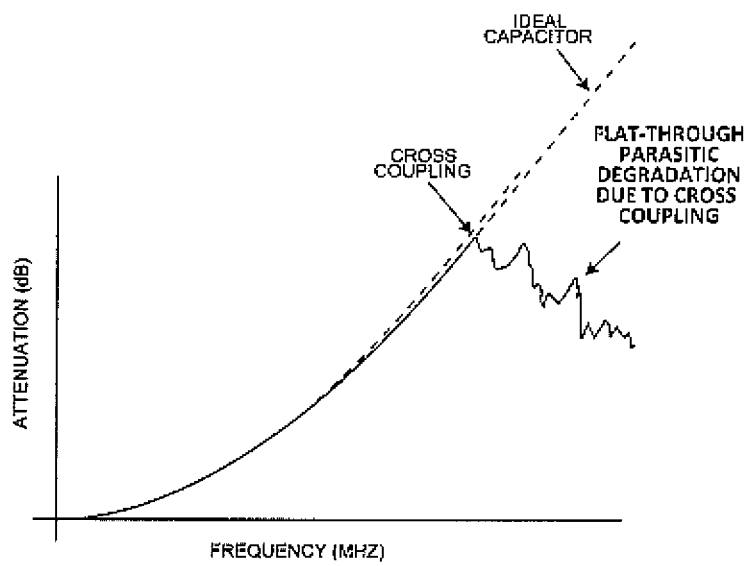
Figure 20:
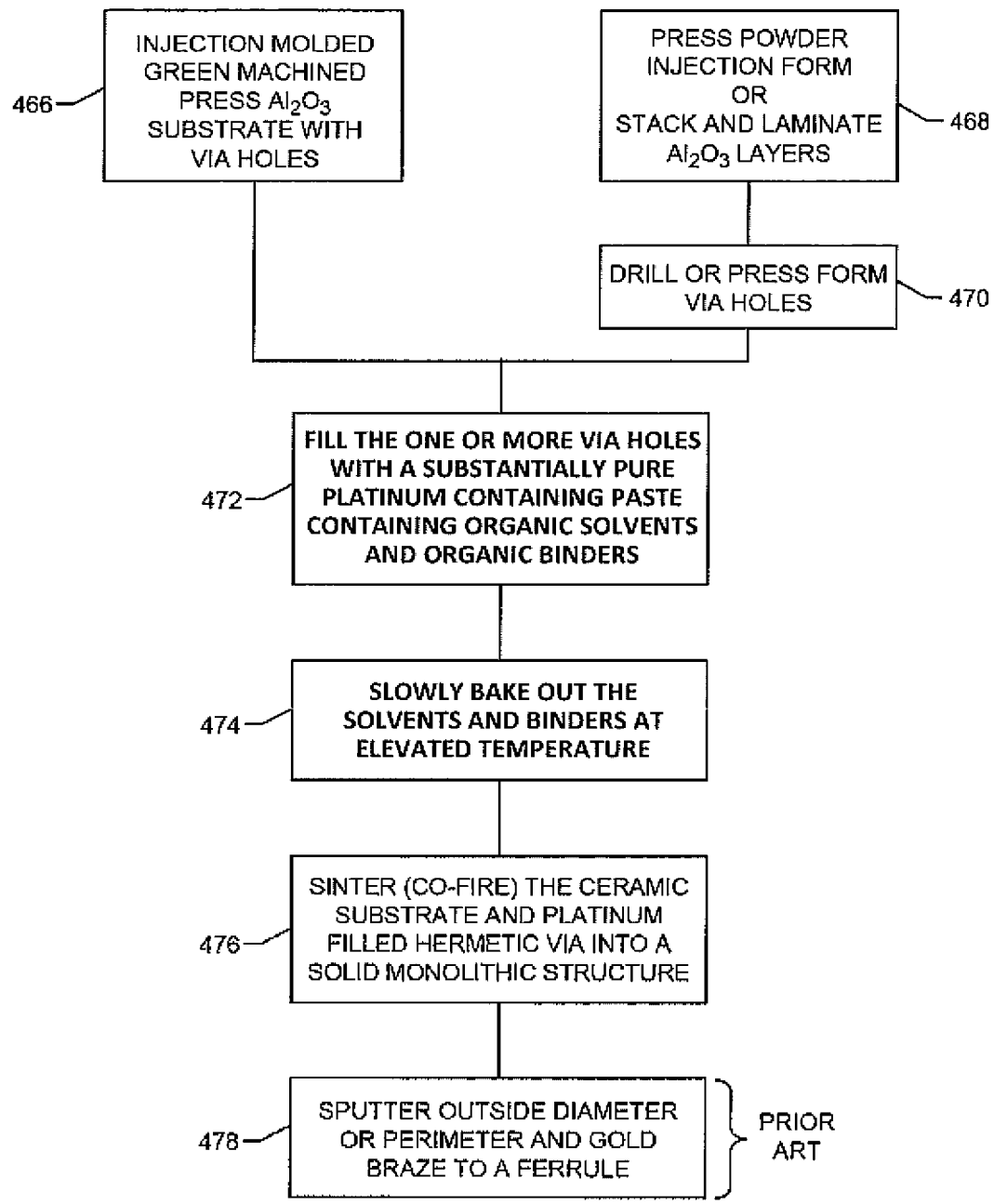
Figure 48:
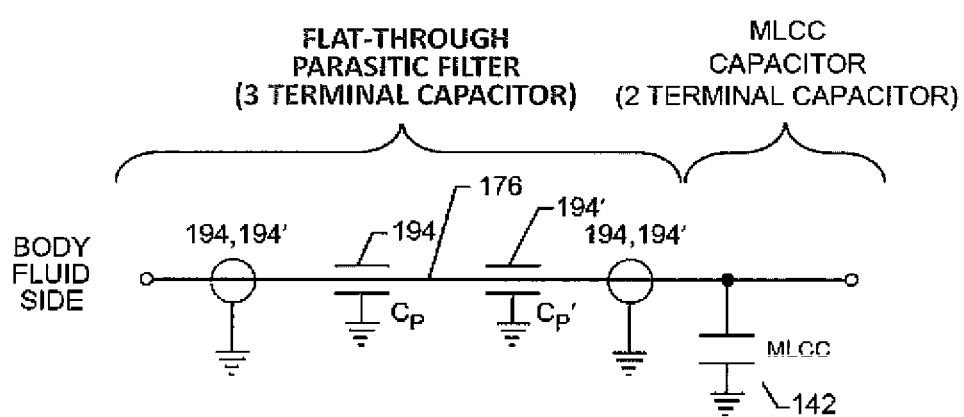
Figure 59:
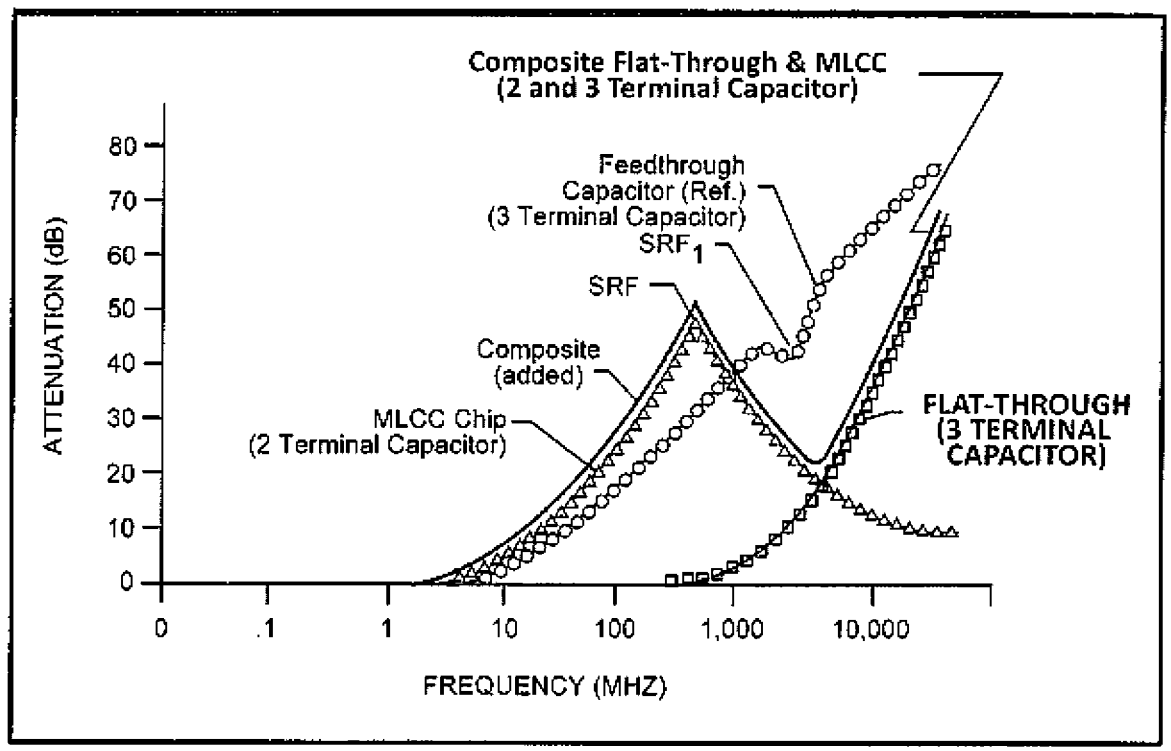
Figure 67:
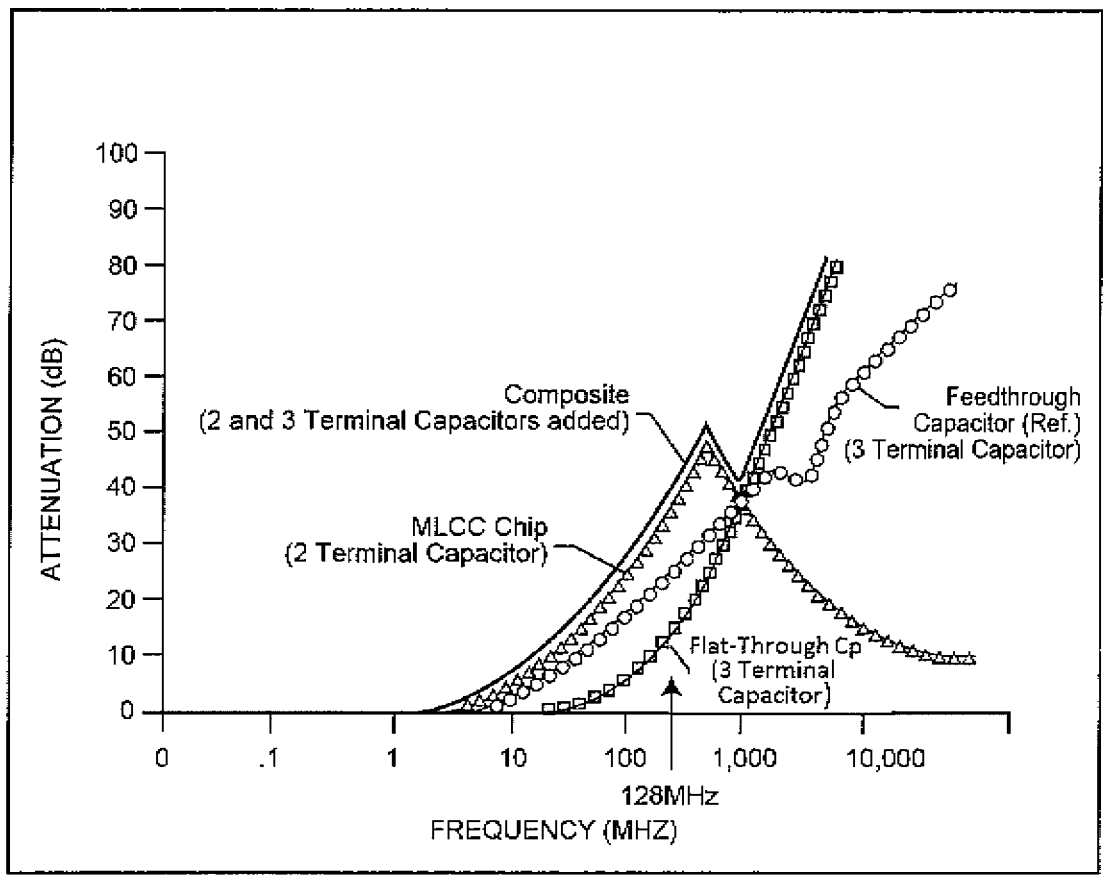

FIG. 96 is an oblique view of a quadpolar hermetic seal similar to that shown in FIG. 30 but now embodying a novel pocket 485 formed in the ferrule 120. The filter capacitor 190 is not shown in this view so that one can see the ferrule 120 having a centered and internally ground connection point with the novel pocket 485 formed therein. As best shown in FIG. 99, a gold braze preform 487 may be placed within the pocket 485 for capturing the preform 487 so that it facilitates the electrical connection to an internally grounded filter via 196 with connection material 128. FIG. 96 shows that each via 486, 486', 486" and 486'" has its own discrete insulator portion 118, 118', 118" and 118'" that is formed within the four through sections of the ferrule 120. The preform 487 is brazed to the ferrule at the same time the hermetic seal 124 is brazed to the ferrule 120 as this simplifies manufacturing of the sealed feedthrough assembly.

Figure 97:
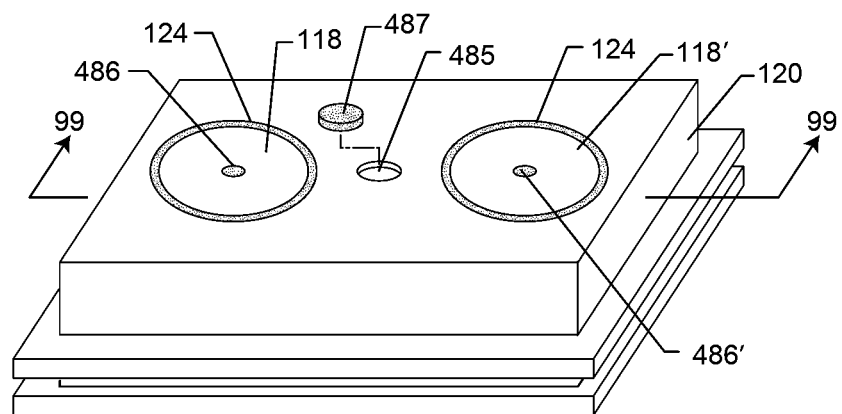
FIG. 97 is an oblique view of another embodiment of a rectangular-shaped bipolar hermetic seal similar in function to FIG. 96.

FIG. 97 is an oblique view of another embodiment of a rectangular-shaped bipolar hermetic seal similar in function to FIG. 96. Here, a rectangular-shaped ferrule 120 has two through holes which surround the insulators 118 and 118' and the platinum filled vias 486 and 486'. A novel pocket 485 is formed in the ferrule 120 to facilitate attachment to a filter capacitor 190. Here, the gold preform 487 is shown above the pocket 485 such that one can see the pocket 485 formed in the ferrule 120.

Figure 98:
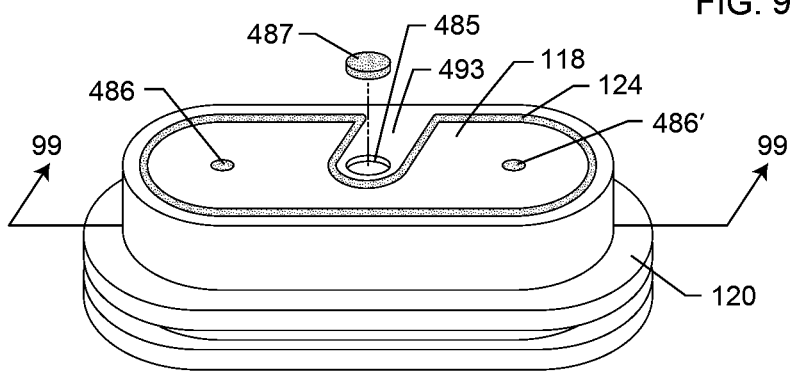
FIG. 98 is an oblique view of another embodiment of an oval-shaped bipolar hermetic seal similar in function to FIG. 96.

FIG. 98 is an oblique view of yet another embodiment of a bipolar hermetic seal similar in function to FIGS. 96 and 97. Here, an oval-shaped (slot-shaped) ferrule 120 has a peninsula structure 493 that incorporates the novel pocket 485. Again, the gold preform 487 is shown above the pocket 485 such that one can see the pocket 485. In actuality, the preform 487 is brazed to the ferrule 120 at the same time the braze 124 is made. As can be seen from FIGS. 96-98, it is understood that one skilled in the art can create a variety of novel ferrules 120 that may be constructed to attach to an internally grounded via 196,128 of a filter capacitor 190 which are consistent with the teachings of this disclosure.

FIG. 99 is a sectional view taken along lines 99-99 from FIGS. 96-98 now shown with a filter 190. FIG. 99 shows the connection between the platinum fill 486 and 486' in the insulator 118 to the active vias 114" and 114'" and the connections 128" and 128'" in the filter 190. One can see that the center portion of the ferrule 120 has a pocket 485 that captures a gold preform 487. One can see that the ground electrode plates 194 of the capacitor 190 are electrically connected to the ferrule 120 through the ground via 196, connection material 128 and brazed preform 487. Also shown are adhesion layers 452 and wetting layers 450 that facilitate a hermetic and reliable seal.

From the foregoing, it will be appreciated that the shielded three-terminal flat-through EMI/energy dissipating filters 190 of the present invention have broad application and may be used with a wide range of connectors, terminals and/or hermetic seals that support lead wires as they ingress/egress into electronic modules or shielded housings. The flat-through EMI/energy dissipating filters 190 of the present invention provide three-terminal capacitive filtering while simultaneously providing shielding of circuits and signals passing through the robust high current capability electrodes of the flat-through capacitor. The hybrid substrate 192 forming a major component of the energy-dissipating filter 190 of the present invention, functions in a very equivalent manner to prior art feedthrough capacitors in that: its internal ground plates act as a continuous part of the overall electromagnetic shield housing of the electronic device or module to physically block direct entry of high frequency RF energy through the hermetic seal or the equivalent opening for lead wire ingress and egress; and, the flat-through EMI/energy dissipating filter effective shunts undesired high frequency EMI signals away from the lead wire (electrodes) to the overall shield housing where such energy is dissipated in eddy currents resulting in a very small temperature rise.

In its most basic form, the shielded three-terminal flat-through EMI/energy dissipating filter comprises an active electrode plate through which a circuit current passes between a first terminal and a second terminal, and a plurality of shield plates substantially enveloping the active electrode plate, wherein the shield plates are collectively coupled to a grounded third terminal. More particularly, the plurality of shield plates include a first shield plate on a first side of the active electrode plate, and a second shield plate on a second side of the active electrode plate opposite the first shield plate.

Although several embodiments of the invention have been described in detail for purposes of illustration, various modifications of each may be made without departing from the spirit and scope of the invention. Accordingly, the invention is not to be limited, except as by the appended claims.

What is claimed is:

1. A hermetic terminal assembly for an active implantable medical device (AIMD), the hermetic terminal assembly comprising:
   a) a hermetically sealed feedthrough configured to be attachable to a ferrule or an AIMD housing, the feedthrough comprising:
      i) an alumina substrate comprised of at least 96 percent alumina and having a thickness extending from a first substrate side to a second substrate side;
      ii) a via hole disposed through the alumina substrate from the first substrate side to the second substrate side;
      iii) a substantially closed pore and substantially pure platinum fill disposed within the via hole and extending between the first substrate side and the second substrate side of the alumina substrate; and
      iv) a hermetic seal between the platinum fill and the alumina substrate, wherein the platinum fill forms a tortuous and mutually conformal knitline or interface between the alumina substrate and the platinum fill; and
   b) a shielded three-terminal flat-through EMI energy dissipating filter comprising:
      i) at least one active electrode plate through which a circuit current is configured to pass between a first terminal and a second terminal;
      ii) at least one first shield plate disposed on a first side of the at least one active electrode plate; and
      iii) at least one second shield plate disposed on a second side of the at least one active electrode plate, where the at least one second shield plate is disposed opposite the at least one first shield plate;

iv) wherein the at least one first and second shield plates are both electrically coupled to a third terminal, where the third terminal is configured to be electrically coupled directly or indirectly to the ferrule or the AIMD housing;

v) wherein the platinum fill is electrically coupled directly or indirectly to the at least one active electrode plate and where the platinum fill is in non-conductive relationship to the at least one first and second shield plates, the ferrule and the AIMD housing.

2. The hermetic terminal assembly of claim 1, including an insulative washer disposed between the shielded three-terminal flat-through EMI energy dissipating filter and the alumina substrate.

3. The hermetic terminal assembly of claim 2, wherein the insulative washer comprises an adhesive insulative washer.

4. The hermetic terminal assembly of claim 1, wherein the shielded three-terminal flat-through EMI energy dissipating filter is mounted directly onto at least a portion of the alumina substrate.

5. The hermetic terminal assembly of claim 1, wherein the at least one active electrode plate is insulated from both the at least one first and second shield plates by a monolithic dielectric substrate.

6. The hermetic terminal assembly of claim 1, wherein the at least one active electrode plate comprises a plurality of active electrode plates.

7. The hermetic terminal assembly of claim 6, wherein the at least one first and second shield plates comprise a plurality of shield plates in non-conductive relationship to the plurality of active electrode plates.

8. The hermetic terminal assembly of claim 1, including a conductive pad electrically coupled to the at least one active electrode plate and forming the second terminal, wherein the conductive pad comprises a wire bond pad disposed on an exterior surface of the shielded three-terminal flat-through EMI energy dissipating filter.

9. The hermetic terminal assembly of claim 1, wherein the third terminal comprises a metallization, the metallization configured to be electrically coupled to the ferrule or the AIMD housing.

10. The hermetic terminal assembly of claim 1, wherein the hermetically sealed feedthrough comprises a second via hole disposed through the alumina substrate from the first substrate side to the second substrate side, a second substantially closed pore and substantially pure platinum fill disposed within the second via hole and extending between the first substrate side and the second substrate side of the alumina substrate, and a second hermetic seal between the second platinum fill and the alumina substrate, wherein the second platinum fill forms a second tortuous and mutually conformal knitline or interface between the alumina substrate and the second platinum fill, and including at least one ground electrode plate disposed within the alumina substrate, wherein the at least one ground electrode plate is configured to electrically couple the second platinum fill to the ferrule or the AIMD housing, and where the second platinum fill is electrically coupled to the third terminal.

11. The hermetic terminal assembly of claim 1, wherein the at least one active electrode plate at least partially comprises an inductor.

12. The hermetic terminal assembly of claim 1, including a first monolithic chip capacitor electrically coupled between the at least one active electrode plate and the at least one first or second shield plates.

13. The hermetic terminal assembly of claim 12, including a second monolithic chip capacitor electrically coupled in series with the at least one active electrode plate.

14. The hermetic terminal assembly of claim 1, wherein the at least one active electrode plate is configured to form at least a component of a capacitor, a bandstop filter, an LC trap filter, an "L", a "π", a "T", a "LL", a "5 element" or an "n" element passive electronic low-pass filter, wherein the "n" element passive electronic low-pass filter is optimized for use at MRI frequencies.

15. The hermetic terminal assembly of claim 1, wherein the at least one active electrode plate is electrically connected to a passive or active electronic component within the AIMD.

16. The hermetic terminal assembly of claim 1, wherein the shielded three-terminal flat-through EMI energy dissipating filter is disposed on the second substrate side of the alumina substrate.

17. The hermetic terminal assembly of claim 1, wherein the shielded three-terminal flat-through EMI energy dissipating filter is biocompatible and disposed on a first substrate side of the alumina substrate.

18. The hermetic terminal assembly of claim 1, wherein the alumina dielectric substrate comprises at least 99 percent alumina, and wherein the platinum fill is substantially free of oxides, sintering additives and glasses, and wherein the alumina dielectric substrate is substantially free of sintering additives and glasses.

19. The hermetic terminal assembly of claim 1, wherein the hermetic seal comprises a leak rate no greater than $1 \times 10^{-7}$ atmospheres cubic centimeters per second of helium.

20. The hermetic terminal assembly of claim 1, wherein an inherent shrink rate during an elevated temperature sintering of the alumina substrate in a green state is greater than the platinum fill in the green state.

21. The hermetic terminal assembly of claim 1, wherein the platinum fill comprises a larger cross sectional area at either a first via end exposed to the first substrate side or a second via end exposed to the second substrate side as compared to a smaller cross sectional area of the platinum fill between the first and second via ends.

22. The hermetic terminal assembly of claim 1, including an electrically conductive cap or protrusion co-fired to the platinum fill on the first substrate side or the second substrate side.

23. The hermetic terminal assembly of claim 22, wherein the cap or protrusion comprises a biocompatible material, platinum or titanium.

24. The hermetic terminal assembly of claim 1, including an adhesion metallization disposed on an outside circumferential surface of the alumina substrate, and including a wetting metallization disposed on the adhesion metallization.

25. The hermetic terminal assembly of claim 24, including the ferrule disposed around the alumina substrate, and including a braze electrically coupled to the adhesion metallization hermetically sealing the alumina substrate to the ferrule, wherein the braze comprises gold and the ferrule comprises titanium.

26. The hermetic terminal assembly of claim 25, wherein the hermetic seal braze between the alumina substrate and the ferrule comprises a leak rate no greater than $1 \times 10^{-7}$ atmospheres cubic centimeters per second of helium.

27. The hermetic terminal assembly of claim 25, wherein the adhesion metallization comprises titanium, and wherein the wetting metallization comprises niobium or molybdenum.

28. The hermetic terminal assembly of claim 1, wherein the first terminal comprises a first terminal via hole with a conductive metallization electrically coupled to the at least one active electrode plate, wherein the first terminal via hole is hollow, and including a ball grid solder joint or braze between the platinum fill and the conductive metallization.

29. A hermetic terminal assembly for an active implantable medical device (AIMD), comprising:
a) a shielded three-terminal flat-through EMI energy dissipating filter, comprising:
   i) at least one active electrode plate through which a circuit current is configured to pass between a first terminal and a second terminal;
   ii) at least one first shield plate disposed on a first side of the at least one active electrode plate; and
   iii) at least one second shield plate disposed on a second side of the at least one active electrode plate and disposed opposite the at least one first shield plate;
   iv) wherein the at least one first and second shield plates are both electrically coupled to a third terminal; and
b) a hermetically sealed feedthrough configured to be attachable to a ferrule or an AIMD housing, the feedthrough comprising:
   i) an alumina substrate comprised of at least 96% alumina and having a thickness extending from a first substrate side to a second substrate side;
   ii) a via hole disposed through the alumina substrate from the first substrate side to the second substrate side;
   iii) a first substantially closed pore and substantially pure platinum fill disposed within the via hole and extending between the first substrate side and the second substrate side of the alumina substrate, wherein the first platinum fill forms a tortuous and mutually conformal knitline or interface between the alumina substrate and the first platinum fill;
   iv) a hermetic seal between the first platinum fill and the alumina substrate;
   v) wherein the platinum fill is electrically coupled to the first terminal where the at least one active electrode plate is in non-conductive relationship to the at least one first and second shield plates, the ferrule and the AIMD housing;
   vi) a grounded via hole disposed through the alumina substrate from the first substrate side to the second substrate side;
   vii) a second substantially closed pore platinum fill disposed within the grounded via hole and extending between the first substrate side and the second substrate side of the alumina substrate; and
   viii) a second hermetic seal between the second platinum fill and the alumina substrate;
   ix) wherein the second platinum fill is electrically coupled to the third terminal and wherein the second platinum fill is configured to be electrically coupled directly or indirectly to the ferrule or AIMD housing.

30. The hermetic terminal assembly of claim 29, including at least one grounded electrode plate disposed in the alumina substrate electrically coupled to the second platinum fill and in non-conductive relation to the first platinum fill.

31. The hermetic terminal assembly of claim 30, including an outer metallization disposed on the alumina substrate and electrically connected to the at least one grounded electrode plate, where the outer metallization is configured to be electrically coupled to either the ferrule or the AIMD housing.

32. A hermetic terminal assembly for an active implantable medical device (AIMD), comprising:
a) a shielded three-terminal flat-through EMI energy dissipating filter comprising:
   i) at least one active electrode plate through which a circuit current is configured to pass between a first terminal and a second terminal;
   ii) at least one first shield plate disposed on a first side of the at least one active electrode plate; and
   iii) at least one second shield plate disposed on a second side of the at least one active electrode plate and disposed opposite the at least one first shield plate;
   iv) wherein the at least one first and second shield plates are both electrically coupled to a third terminal, where the third terminal is configured to be electrically coupled directly or indirectly to a ferrule or an AIMD housing;
   v) wherein the at least one active electrode plate, the at least one first shield plate and the at least one second shield plate are disposed within a monolithic dielectric substrate and wherein the at least one active electrode plate is insulated from both the at least one first and second shield plates by the monolithic dielectric substrate; and
b) a hermetically sealed feedthrough configured to be attachable to the ferrule or the AIMD housing, the feedthrough comprising:
   i) an alumina substrate comprised of at least 96 percent alumina and having a thickness extending from a first substrate side to a second substrate side;
   ii) a via hole disposed through the alumina substrate from the first substrate side to the second substrate side;
   iii) a substantially closed pore and substantially pure platinum fill disposed within the via hole and extending between the first substrate side and the second substrate side of the alumina substrate; and
   iv) a hermetic seal between the platinum fill and the alumina substrate, wherein the platinum fill forms a tortuous and mutually conformal knitline or interface between the alumina substrate and the platinum fill;
   v) wherein the platinum fill is electrically coupled directly or indirectly to the at least one active electrode plate where the platinum fill is in non-conductive relationship to the at least one first and second shield plates, the ferrule and the AIMD housing; and
c) a monolithic chip capacitor electrically coupled directly or indirectly between the at least one active electrode plate and the at least one first or second shield plates.

* * * * *

UNITED STATES PATENT AND TRADEMARK OFFICE
CERTIFICATE OF CORRECTION

PATENT NO. : 9,463,329 B2
APPLICATION NO. : 14/556239
DATED : October 11, 2016
INVENTOR(S) : Christine A. Frysz et al.

It is certified that error appears in the above-identified patent and that said Letters Patent is hereby corrected as shown below:

In the Drawings

Figure 12:
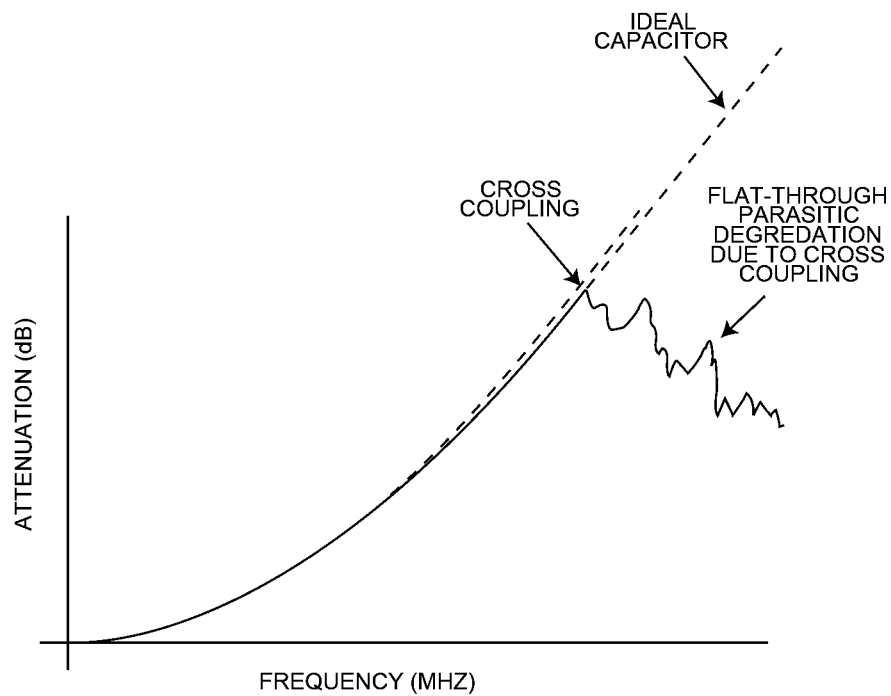
FIG. 12 illustrates the attenuation versus frequency response curve of the typical flat-through capacitor of FIGS. 9 and 10.

Sheet 7 of 60, FIG. 12, at the right side of the graph in the phrase description delete "DEGREDATION" and insert --DEGRADATION-- (See attached sheet)
Sheet 11 of 60, FIG. 20, in box 472 delete "SUBSTANCIALLY" and insert --SUBSTANTIALLY-- (See attached sheet)
Sheet 11 of 60, FIG. 20, in box 474 delete "TEMERATURE" and insert --TEMPERATURE-- (See attached sheet)
Sheet 25 of 60, FIG. 48, above the left bracket, Line 1, delete "THRU" and insert --THROUGH-- (See attached sheet)
Sheet 31 of 60, FIG. 59, in Line 1 of the first phrase at the top, delete "Composit" and insert --Composite-- (See attached sheet)
Sheet 31 of 60, FIG. 59, in Line 1 of the first phrase at the top, delete "Thru" and insert --Through-- (See attached sheet)
Sheet 31 of 60, FIG. 59, in Line 1 of the phrase at the far right, delete "THRU" and insert --THROUGH-- (See attached sheet)
Sheet 38 of 60, FIG. 67, in Line 1 of the phrase directly above the x-axis, delete "FLAT-THRU" and insert --Flat-Through-- (See attached sheet)

In the Claims

Column 46, Line 31 (Claim 19, Line 3) delete "atmospheres" and insert --standard--
Column 46, Line 63 (Claim 26, Line 4) delete "atmospheres" and insert --standard--

Signed and Sealed this
Eleventh Day of July, 2017

Joseph Matal
*Performing the Functions and Duties of the
Under Secretary of Commerce for Intellectual Property and
Director of the United States Patent and Trademark Office*

FILTER PERFORMANCE